US010563204B2

(12) United States Patent
Lu et al.

(10) Patent No.: US 10,563,204 B2
(45) Date of Patent: Feb. 18, 2020

(54) METHODS OF TREATING CANCER HARBORING HEMIZYGOUS LOSS OF TP53

(71) Applicant: Board of Regents, The University of Texas System, Austin, TX (US)

(72) Inventors: Xiongbin Lu, Houston, TX (US); Yunhua Liu, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/555,411

(22) PCT Filed: Mar. 3, 2016

(86) PCT No.: PCT/US2016/020687
§ 371 (c)(1),
(2) Date: Sep. 1, 2017

(87) PCT Pub. No.: WO2016/141185
PCT Pub. Date: Sep. 9, 2016

(65) Prior Publication Data
US 2018/0044681 A1 Feb. 15, 2018

Related U.S. Application Data

(60) Provisional application No. 62/128,480, filed on Mar. 4, 2015.

(51) Int. Cl.
| | | |
|---|---|---|
| *A61K 39/395* | (2006.01) | |
| *C12N 15/00* | (2006.01) | |
| *C12N 15/113* | (2010.01) | |
| *A61K 31/7088* | (2006.01) | |
| *A61K 45/06* | (2006.01) | |
| *C07K 16/30* | (2006.01) | |
| *A61K 47/68* | (2017.01) | |
| *A61K 31/7105* | (2006.01) | |
| *C12Q 1/6886* | (2018.01) | |
| *G01N 33/574* | (2006.01) | |

(52) U.S. Cl.
CPC ...... *C12N 15/1137* (2013.01); *A61K 31/7088* (2013.01); *A61K 31/7105* (2013.01); *A61K 45/06* (2013.01); *A61K 47/6831* (2017.08); *A61K 47/6849* (2017.08); *A61K 47/6851* (2017.08); *C07K 16/30* (2013.01); *C12N 15/113* (2013.01); *C12Q 1/6886* (2013.01); *G01N 33/57496* (2013.01); *C12N 2310/14* (2013.01); *C12N 2310/531* (2013.01); *C12N 2320/31* (2013.01); *C12Q 2600/106* (2013.01); *C12Q 2600/158* (2013.01); *G01N 2333/4748* (2013.01); *G01N 2333/912* (2013.01)

(58) Field of Classification Search
None
See application file for complete search history.

(56) References Cited

U.S. PATENT DOCUMENTS 9,938,323 B2 * 4/2018 Grunewald .............. C07K 7/64
2009/0304666 A1 12/2009 Harrison et al.

FOREIGN PATENT DOCUMENTS

| WO | WO 2010/115630 | 10/2010 |
|---|---|---|
| WO | WO 2012/119787 | 9/2012 |
| WO | WO 2014/135282 | 9/2014 |

OTHER PUBLICATIONS

Ikediobi et al. (Mol Cancer Ther 2006;5(11) Nov. 2006) (Year: 2006).*
Liu et al. (Nature Apr. 30, 2015;520(7549):697-701) (Year: 2015).*
Bensaude, "Inhibiting eukaryotic transcription: Which compound to choose? How to evaluate its activity?" *Transcription*, 2(3):103, 2011.
Chene, "Inhibiting the p53-MDM2 interaction: an important target for cancer therapy," *Nat. Rev. Cancer*, 3(2):102, 2003.
Cheok et al., "Translating p53 into the clinic," *Nat. Rev. Clin. Oncol.*, 8(1):25, 2011.
Derheimer et al., "RPA and ATR link transcriptional stress to p53," *Proc. Natl. Acad. Sci. USA*, 104(31):12778, 2007.
Faulstich and Fiume, "Protein conjugates of fungal toxins," *Methods Enzymol.*, 112:225-237, 1985.
Goldstein et al., "Understanding wild-type and mutant p53 activities in human cancer: new landmarks on the way to targeted therapies," *Cancer Gene Ther.*, 18(1):2, 2011.
Guschin et al., "A rapid and general assay for monitoring endogenous gene modification," *Methods Mol. Biol.*, 649:247-256, 2010.
Haupt and Haupt, "Manipulation of the tumor suppressor p53 for potentiating cancer therapy," *Semin. Cancer Biol.*, 14(4):244, 2004.
Lane et al., "P53-based cancer therapy," *Cold Spring Harb. Perspect. Biol.*, 2(9):a001222, 2010.
Letschert et al., "Molecular characterization and inhibition of amanitin uptake into human hepatocytes," *Toxicol. Sci.*, 91(1):140, 2006.
Lindell et al., "Specific inhibition of nuclear RNA polymerase II by alpha-amanitin," *Science*, 170(3956):447, 1970.
Liu et al., "Kaposi's sarcoma-associated herpesvirus-encoded microRNA miR-K12-11 attenuates transforming growth factor beta signaling through suppression of SMAD5," *Journal of Virology*, 86:1372-1381, 2012.

(Continued)

*Primary Examiner* — Meera Natarajan
(74) *Attorney, Agent, or Firm* — Parker Highlander PLLC

(57) ABSTRACT

Provided herein are methods of treating a patient having a cancer that exhibits (i) a hemizygous loss of the TP53 gene; (ii) a hemizygous loss of the POLR2A gene; and/or (iii) a decreased level of expression of a POLR2A gene product relative to a reference (i.e., control) expression level. The methods comprise administering a therapeutically effective amount of a POLR2A inhibitor (e.g., a nucleic acid that inhibits the expression of a POLR2A protein, an amatoxin, alpha-amanitin, or alpha-amanitin conjugated to a cell targeting moiety, such as an EpCAM antibody) to a patient having or determined to have (i) a hemizygous loss of the TP53 gene; (ii) a hemizygous loss of the POLR2A gene; and/or (iii) a decreased level of expression of a POLR2A gene product relative to a reference (i.e., control) level.

16 Claims, 42 Drawing Sheets

Specification includes a Sequence Listing.

(56) References Cited

OTHER PUBLICATIONS

Lu et al., "Endothelial cells promote the colorectal cancer stem cell phenotype through a soluble form of Jagged-1," *Cancer Cell*, 23(2):171, 2013.

Moldenhauer et al., "Therapeutic potential of amanitin-conjugated anti-epithelial cell adhesion molecule monoclonal antibody against pancreatic carcinoma," *J. Natl. Cancer Inst.*, 104(8):622, 2012.

Negrini et al., "Genomic instability—an evolving hallmark of cancer," *Nat. Rev. Mol. Cell Biol.*, 11(3):220, 2010.

Nijhawan et al., "Cancer vulnerabilities unveiled by genomic loss," *Cell*, 150(4):842-854, 2012.

Pecot et al., "Therapeutic Silencing of KRAS Using Systemically Delivered siRNAs," *Mol. Cancer Ther.*, 13(12):2876-2885, 2014.

Petitjean et al., "Impact of mutant p53 functional properties on TP53 mutation patterns and tumor phenotype: lessons from recent developments in the IARC TP53 database," *Hum. Mutat.*, 28(6):622, 2007.

Ran et al., "Genome engineering using the CRISPR-Cas9 system," *Nature Protocols*, 8:2281-2308, 2013.

Shalem et al., "Genome-scale CRISPR-Cas9 knockout screening in human cells," *Science*, 343(6166):84, 2014.

Toledo and Wahl, "Regulating the p53 pathway: in vitro hypotheses, in vivo veritas," *Nat. Rev. Cancer*, 6(12):909, 2006.

Vazquez et al., "The genetics of the p53 pathway, apoptosis and cancer therapy," *Nat. Rev. Drug Discov.*, 7(12):979, 2008.

Wade et al., "MDM2, MDMX and p53 in oncogenesis and cancer therapy," *Nat. Rev. Cancer*, 13(2):83, 2013.

Wang et al., "Genetic screens in human cells using the CRISPR-Cas9 system," *Science*, 343(6166):80, 2014.

Wang et al., "One-step generation of mice carrying mutations in multiple genes by CRISPR/Cas-mediated genome engineering," *Cell*, 153(4):910, 2013.

Went et al., "Frequent EpCam protein expression in human carcinomas," *Hum. Pathol.*, 35(1):122, 2004.

Adair et al., "Antibody-drug conjugates—a perfect synergy," *Expert Opinion on Biological Therapy*, 12(9):1191-1206, 2012.

Davis et al., "A conjugate of α-amanitin and monoclonal immunoglobulin G to Thy 1.2 antigen is selectively toxic to T lymphoma cells," *Science*, 213(4514):1385-1388, 1981.

Fluiter et al., "Killing cancer by targeting genes that cancer cells have lost: allele-specific inhibition, a novel approach to the treatment of genetic disorders," *Cellular and Molecular Life Sciences*, 60(5):834-843, 2003.

Fluiter et al., "Tumor genotype-specific growth inhibition in vivo by antisense oligonucleotides against a polymorphic site of the large subunit of human RNA polymerase II," *Cancer Research*, 62(7):2024-2028, 2002.

Liu et al., "A new way to target p53-defective colorectal cancer," *Future Oncology*, 11(23):3101-3104, 2015.

Liu et al., "TP53 loss creates therapeutic vulnerability colorectal cancer," *Nature*, 520(7549):697-701, 2015.

Mook et al., "Allele-specific cancer cell killing in vitro and in vivo targeting a single-nucleotide polymorphism in POLR2A," *Cancer Gene Therapy*, 16(6):532-538, 2009.

PCT International Preliminary Report on Patentability issued in International Application No. PCT/US2016/020687, dated Sep. 14, 2017.

PCT International Search Report and Written Opinion issued in International Application No. PCT/US2016/020687, dated May 23, 2016.

Seton-Rogers, "Colorectal cancer: a circuitous way to target p53," *Nature Reviews Cancer*, 15(6):318-319, 2015.

Rajpal et al., "Introduction: antibody structure and function," *Therapeutic Fc-Fusion Proteins*, First Edition, edited by Chamow, 1:1-43, 2014.

Simpson and Caballero, "Monoclonal antibodies for the therapy of cancer," *BMC Proceedings*, 8(Suppl 4):O6, 2014.

Vacchelli et al., "Trial watch: tumor-targeting monoclonal antibodies for oncological indications," *OncoImmunology*, 4:1, e985940, 2015.

\* cited by examiner

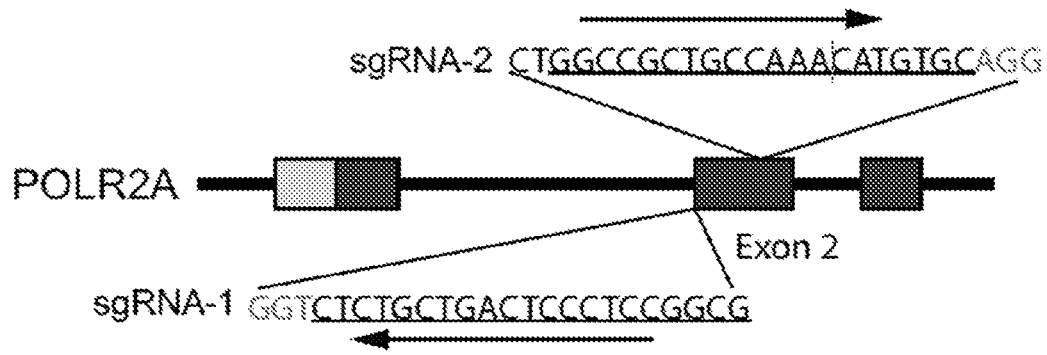
FIG. 9A
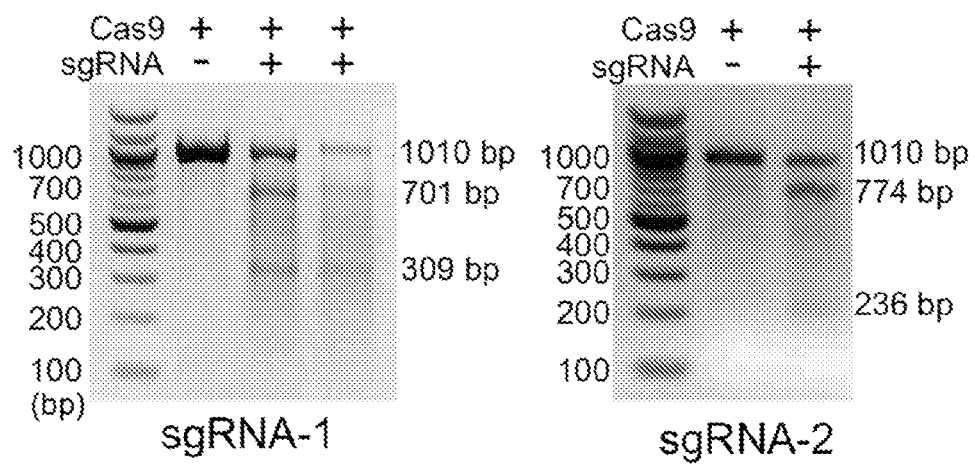
FIG. 9B
sgRNA-1 mutant #14
GGGGCGGCCTCCCTCAGTCGTCTCTGGGTATTTGATGCC  WT
GGGGCGGCCTCCCTCAGTC---CTCTGGGTATTTGATGCC  -2 bp
sgRNA-2 mutant #5
GGACTGGCCGCTGCCAAACATGTGCAGGTAAGTGCTGG  WT
GGACTGGCCGCTGCCAAAC---------------TGCTGG  -13 bp
FIG. 9C

METHODS OF TREATING CANCER HARBORING HEMIZYGOUS LOSS OF TP53

This application is a national phase application under 35 U.S.C. § 371 of International Application No. PCT/US2016/020687, filed Mar. 3, 2016, which claims benefit of priority to U.S. Provisional Application Ser. No. 62/128,480, filed Mar. 4, 2015, the entire contents of each of which are hereby incorporated by reference The invention was made with government support under Grant Nos. R01 CA136549 and U54 CA151668 awarded by the National Institutes of Health. The government has certain rights in the invention.

BACKGROUND OF THE INVENTION

1. Field of the Invention

The present invention relates generally to the fields of medicine and cancer biology. More particularly, it concerns methods of treating cancers harboring hemizygous loss of TP53.

2. Description of Related Art

TP53, a well-known tumor suppressor gene, is frequently inactivated by mutation or deletion in a majority of human tumors (Petitgean et al., 2007; Vazquez et al., 2008). A tremendous effort has been made to restore p53 activity in cancer therapies (Chene, 2003; Wade et al., 2013). Whereas gene therapy using adenoviral vectors expressing wildtype p53 has shown activity in several clinical trials, the variable and insufficient gene delivery to every tumor cell and the presence of a host antibody to adenovirus limited its clinical use (Lane et al., 2010; Haupt and Haupt, 2004). A number of small chemical compounds that boost p53 activity have also been developed. However, they can only be applied in human cancers possessing wildtype p53 (Cheok et al., 2011; Goldstein et al., 2011). However, no effective p53-based therapy has been successfully translated into clinical cancer treatment due to the complexity of p53 regulators and their poor drugability. As such, new strategies to treat p53-deficient cancers are needed.

SUMMARY OF THE INVENTION

In some embodiments, there are provided methods of treating a patient having cancer cells that exhibit (i) a hemizygous loss of the TP53 gene; (ii) a hemizygous loss of the POLR2A gene; and/or (iii) a decreased level of expression of a POLR2A gene product relative to a reference expression level (e.g., an expression level in a non-cancerous sample), the method comprising administering a therapeutically effective amount of a POLR2A inhibitor to such a patient. In certain aspects, the patient has cancer cells that exhibit a hemizygous loss of the TP53 gene. In certain aspects, the patient has cancer cells that exhibit a hemizygous loss of the POLR2A gene. In certain aspects, the patient has cancer cells that exhibit a decreased level of expression of a POLR2A gene product relative to a reference expression level.

In certain aspects, a POLR2A inhibitor comprises a nucleic acid that inhibits the expression of a POLR2A protein. In certain aspects, a POLR2A inhibitor comprises alpha-amanitin. In some aspects, the alpha-amanitin is conjugated to an antibody, such as an antibody that targets a cancer cells (e.g., a tumor-associated antigen antibody). In some aspects, the antibody may be an EpCAM-specific antibody.

In certain aspects, the POLR2A gene product is an mRNA. A level of expression of an mRNA may be determined by Northern blotting, reverse transcription-quantitative real-time PCR (RT-qPCR), nuclease protection, transcriptome analysis, a hybridization assay, a chip-based expression platform, or an invader RNA assay platform. In certain aspects, the POLR2A gene product is a protein. A level of expression of a protein may be determined by mass spectrometry, western blot, ELISA, immunoprecipitation, immunohistochemistry, or radioimmunoassay. In certain aspects, a genomic copy number is detected to determine the hemizygous loss of the TP53 gene or the hemizygous loss of the POLR2A gene. In some aspects, genomic copy number is determined by a genomic hybridization technique (e.g. FISH analysis), PCR analysis (e.g., real-time PCR), or restriction fragment analysis.

In certain aspects, the cancer is a lung cancer, brain cancer, breast cancer, liver cancer, ovarian cancer, colorectal cancer, prostate cancer, or pancreatic cancer. In certain aspects, the cancer is metastatic, recurrent, or multi-drug resistant.

In certain aspects, the methods further comprise administering at least a second anticancer therapy to the subject. In certain aspects, the second anticancer therapy is a surgical therapy, chemotherapy, radiation therapy, cryotherapy, hormonal therapy, toxin therapy, immunotherapy, or cytokine therapy. In certain aspects, the chemotherapy is 5-fluorouracil, oxaliplatin, or SN-38.

In certain aspects, the patient is a human. In certain aspects, the patient is a non-human mammal.

In certain aspects, the patient is treated at least a second time. In certain aspects, the patient is treated over a period of 1 week to 6 months. In certain aspects, the patient has previously undergone at least one round of anti-cancer therapy In some embodiments, there are provided methods of treating a patient having cancer comprising (a) selecting a patient determined to have cancer cells comprising (i) a hemizygous loss of the TP53 gene; (ii) a hemizygous loss of the POLR2A gene; and/or (iii) a decreased level of expression of a POLR2A gene product relative to a reference level; and (b) administering a therapeutically effective amount of a POLR2A inhibitor to the patient.

In certain aspects, selecting a patient comprises obtaining a sample of the cancer and determining whether cells of the cancer comprise (i) a hemizygous loss of the TP53 gene; (ii) a hemizygous loss of the POLR2A gene; and/or (iii) a decreased level of expression of a POLR2A gene product relative to a reference level. In certain aspects, the methods further comprise providing a report of the determining. In certain aspects, the report is a written or electronic report. In certain aspects, the report is provided to the patient, a health care payer, a physician, an insurance agent, or an electronic system.

In certain aspects, selecting a patient comprises obtaining results for a test that determines whether the cells of the cancer comprise (i) a hemizygous loss of the TP53 gene; (ii) a hemizygous loss of the POLR2A gene; and/or (iii) a decreased level of expression of a POLR2A gene product relative to a reference level.

In certain aspects, the cells of the cancer comprise a hemizygous loss of the TP53 gene. In certain aspects, the cells of the cancer comprise a hemizygous loss of the POLR2A gene. In certain aspects, the cells of the cancer comprise a decreased level of expression of a POLR2A gene product relative to a reference level (e.g., an expression level in a non-cancerous sample).

In some embodiments, there are provided methods of selecting a drug therapy for a cancer patient comprising (a) obtaining a sample of the cancer; (b) detecting the presence of (i) a hemizygous loss of the TP53 gene; (ii) a hemizygous loss of the POLR2A gene; and/or (iii) a decreased level of expression of a POLR2A gene product relative to a reference level in the cells of the cancer; and (c) selecting a POLR2A inhibitor if (i) a hemizygous loss of the TP53 gene is detected; (ii) a hemizygous loss of the POLR2A gene is detected; and/or (iii) a decreased level of expression of a POLR2A gene product relative to a reference level is detected in the cells of the cancer.

In certain aspects, the methods further comprise administering a therapeutically effective amount of a POLR2A inhibitor to the patient.

In certain aspects, the cells of the cancer comprise a hemizygous loss of the TP53 gene. In certain aspects, the cells of the cancer comprise a hemizygous loss of the POLR2A gene. In certain aspects, the cells of the cancer comprise a decreased level of expression of a POLR2A gene product relative to a reference level (e.g., an expression level in a non-cancerous sample).

In some embodiments, compositions are provided comprising a POLR2A inhibitor for use in the treatment of a cancer in a subject, wherein cells of the cancer have been determined to comprise (i) a hemizygous loss of the TP53 gene; (ii) a hemizygous loss of the POLR2A gene; or (iii) a decreased level of expression of a POLR2A gene product relative to a reference level (e.g., an expression level in cells of a non-cancerous sample).

In some embodiments, there is provided the use of a POLR2A inhibitor in the manufacture of a medicament for the treatment of a cancer, wherein cells of the cancer have been determined to comprise (i) a hemizygous loss of the TP53 gene; (ii) a hemizygous loss of the POLR2A gene; or (iii) a decreased level of expression of a POLR2A gene product relative to a reference level (e.g., an expression level in cells of a non-cancerous sample).

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Analysis of TCGA database shows the frequencies of hemizygous deletion of the TP53 locus in a variety of human cancers. (FIG. 1B) Schematic diagram of genes adjacent to TP53 in human genome. (FIG. 1C) Concomitant deletion of POLR2A in colorectal tumors harbouring hemizygous loss of TP53. (FIG. 1D) Scatterplots of POLR2A copy number versus mRNA expression for clinical colorectal tumors in TCGA and cancer cell lines in CCLE. A linear regression and the Pearson correlation coefficient (r) are displayed. (FIG. 1E) Quantification of POLR2A protein levels in matched normal and CRC tissue samples (neutral or hemizygous-loss POLR2A). (FIG. 1F) Copy number variations of POLR2A and TP53 in human CRC cell lines. Left columns are TP53; right columns are POLR2A. (FIG. 1G) Relative expression levels of POLR2A in CRC cell lines (normalized to HCT116). (FIG. 1H) Protein levels of POLR2A, p53 and β-Actin in CRC cell lines.

(FIG. 2A) POLR2A$^{loss}$ cells (SW837, SNU283) are significantly more sensitive to α-Amanitin treatment than POLR2A$^{neutral}$ cells (HCT116, SW480). Crystal violet staining of cells is shown. (FIG. 2B) Cell proliferation of POLR2A$^{neutral}$ and POLR2A$^{loss}$ cells with α-Amanitin treatment. (FIG. 2C) Dox-induced suppression of POLR2A inhibited the proliferation of SNU283 cells, but not of HCT116 cells. (FIG. 2D) Correlation between POLR2A mRNA expression and cell proliferation in HCT116 and SNU283 cells expressing Dox-inducible POLR2A shRNAs. Data represents mean±SD. Left columns are POLR2A mRNA; right columns are Proliferation. (FIGS. 2E and 2F) Survival curves of SUN283 and SW837 cells in response to increasing doses of α-Amanitin treatment after transfection with increasing amounts of PORL2A expression vector DNA. (FIG. 2G) POLR2A$^{loss}$ HCT116 cells are significantly more sensitive to α-Amanitin treatment than the parental POLR2A$^{neutral}$ HCT116 cells. Crystal violet staining of cells is shown. (FIG. 2H) Cell proliferation of POLR2A$^{neutral}$ and POLR2A$^{loss}$ HCT116 cells treated with α-Amanitin. (FIGS. 2I and 2J) Correlation between POLR2A mRNA expression and cell proliferation (FIG. 2I; left columns are POLR2A mRNA; right columns are Proliferation) or apoptosis (FIG. 2J; left columns are shCtrl; middle columns are shRNA-1; right columns are shRNA-2) in POLR2A$^{neutral}$ and POLR2A$^{loss}$ HCT116 cells. Data represents mean±SD.

(FIG. 3A) Protein levels of POLR2A, p53, EpCAM and β-Actin in a panel of isogenic human primary colorectal cancer xhCRC cell lines.

(FIG. 3B) Growth curve of POLR2A$^{neutral}$ and POLR2A$^{loss}$ xhCRC cells. (FIG. 3C) Cell proliferation of POLR2A$^{neutral}$ and POLR2A$^{loss}$ xhCRC cells treated with α-Amanitin. (FIG. 3D) Sensitivity of POLR2A$^{neutral}$ and POLR2A$^{loss}$ xhCRC cells to 5-FU, Oxaliplatin (Oxa) or SN-38 treatment combined with or without α-Amanitin treatment. (FIG. 3E) Cell proliferation of POLR2A$^{neutral}$ and POLR2A$^{loss}$ xhCRC cells treated with ama-HEA125 (anti-EpCAM) antibody-drug conjugate at various concentrations.

(FIG. 4A) Growth curves of xenograft tumors derived from subcutaneously implanted HCT116 (1×10$^6$ cells) and SNU283 (2×10$^6$ cells) cells. Both cell lines express control or Dox-inducible POLR2A shRNAs. After initial establishment of tumors (100 mm$^3$), mice were treated with 1 μg ml$^{-1}$ of Dox in drinking water. n=5 mice per group. (FIGS. 4B and 4C) Tumor growth curves (FIG. 4B) of xenograft tumors derived from orthotopically implanted POLR2A$^{neutral}$ and POLR2A$^{loss}$ HCT116 cells (1×10$^6$ cells injected) expressing Dox-inducible control or POLR2A shRNA. After initial establishment of tumors, mice were treated with 1 μg ml$^{-1}$ Dox in drinking water. Tumor weights (FIG. 4C) were measured (n=5 mice per group). **p<0.01. (FIGS. 4D and 4E) Tumor growth curves of xenografted tumors derived from orthotopically implanted POLR2A$^{neutral}$ and POLR2A$^{loss}$ HCT116 (FIG. 4D; 1.0×10$^6$ cells injected) or xhCRC (FIG. 4E; 0.5×10$^6$ cells injected) cells that received dual intraperitoneal injections of anti-EpCAM antibody (3.6 mg kg$^{-1}$) or ama-HEA125 antibody-drug conjugate (3, 10, 30 and 90 μg kg$^{-1}$, corresponding to 0.12, 0.4, 1.2 and 3.6 mg IgG kg$^{-1}$). n=10 mice per group.

(FIG. 5A) Quantification of POLR2A expression in human colon normal, POLR2A-neutral or -loss tumor tissue samples. Error bars, s.d. (FIG. 5B) Protein levels of POLR2A and β-Actin in matched normal and CRC tissue samples.

(FIGS. 6A and 6B) Scatterplots of TP53 copy number versus protein expression (FIG. 6A) or mRNA expression (FIG. 6B) in colorectal tumors in TCGA database. The Pearson correlation coefficient (r) and p value are displayed. (FIG. 6C) Relative mRNA expression of TP53 in colorectal cancer cell lines (normalized to that in HCT116 cell line). Data are mean and s.d. of three independent experiments.

(FIG. 7A) Cell proliferation of POLR2A$^{neutral}$ and POLR2A$^{loss}$ cells treated with actinomycin D. (FIG. 7B) Knockdown efficiency of POLR2A-specific shRNAs in HCT116, SW480, SW837 and SNU283 cells. (FIG. 7C) Effect of POLR2A knockdown on the proliferation of four colorectal cancer cell lines. Cells expressing GFP and control or POLR2A-specific shRNAs were sorted and mixed with control GFP-negative cells (1:1) and the GFP positive cells were quantified at passage 2, 4 and 6. p<0.01, ns: not significant. (FIG. 7D) Protein levels of POLR2A and β-Actin in HCT116 and SNU283 cells expressing Dox-inducible POLR2A shRNAs (1.0 μg ml$^{-1}$ Dox). (FIG. 7E) Cell proliferation of HCT116 and SNU283 cells expressing Dox-inducible POLR2A shRNA in the presence of 300 ng ml$^{-1}$ Dox. p<0.01. (FIGS. 7F and 7G) Cell cycle profiles (FIG. 7F; top portion of each column is G2/M; middle portion of each column is S; bottom portion of each column is G0/G1) and apoptosis (FIG. 7G) of control or POLR2A shRNA-expressing HCT116 and SNU283 cells. ** p<0.01. Data are mean and s.d. of three independent experiments.

(FIG. 8A) Protein levels of POLR2A and β-Actin in SNU283 and SW837 cells expressing increasing amounts of exogenous POLR2A. (FIG. 8B) Crystal violet staining of SNU283 and SW837 cells treated with increasing doses of α-Amanitin after transfection with increasing amounts of POLR2A expression vector DNA.

FIGS. 9A-H. Mono-allelic knockout of POLR2A sensitizes HCT116 cells to POLR2A inhibition. (FIG. 9A) Schematic illustration of the Cas9/sgRNA-targeting sites in the POLR2A gene. Two sgRNA-targeting sequences are shown (the arrow indicates directionality; sequences are provided as SEQ ID NOs: 25-26) and the protospacer-adjacent motif (PAM) sequences are the last three nucleotides of each sequence. (FIG. 9B) Efficiency of the Cas9-mediated cleavage of POLR2A in HCT116 cells measured by the Surveyor assay. (FIG. 9C) Sequences of mutant POLR2A alleles in the cells of colonies 14 and 5 (sequences are provided as SEQ ID NOs: 27-30). (FIG. 9D) Protein levels of POLR2A and β-Actin in POLR2A$^{neutral}$ and POLR2A$^{loss}$ HCT116 cells. (FIG. 9E) Growth curves of POLR2A$^{neutral}$ and POLR2A$^{loss}$ HCT116 cells. (FIG. 9F) Relative proliferation of POLR2A$^{neutral}$ and POLR2A$^{loss}$ cells treated with actinomycin D. (FIG. 9G) Effect of POLR2A knockdown on the POLR2A$^{neutral}$ and POLR2A$^{loss}$ HCT116 cells. Experiments were performed as described in FIG. 7C. **p<0.01, ns: not significant. (FIG. 9H) Dox-induced partial suppression of POLR2A inhibited the growth of POLR2A$^{loss}$ HCT116 cells, but not of parental POLR2A$^{neutral}$ HCT116 cells. Data are mean and s.d. of three independent experiments.

(FIG. 10A) Schematic illustration of the Cas9/sgRNA-targeting sites in the TP53 gene. Two sgRNA-targeting sequences are shown (the arrow indicates directionality; sequences are provided as SEQ ID NOs: 31-32) and the PAM sequences are the last three nucleotides of each sequence. (FIG. 10B) Efficiency of the Cas9-mediated cleavage of TP53 in HCT116 cells measured by Surveyor assay. (FIG. 10C) Protein levels of POLR2A, p53 and β-Actin in a panel of isogenic HCT116 cells. (FIG. 10D) Growth curves of POLR2A$^{neutral}$ and POLR2A$^{loss}$ HCT116 cells. (FIGS. 10E and 10F) Crystal staining images (FIG. 10E) and cell survival curves (FIG. 10F) of POLR2A$^{neutral}$ and POLR2A$^{loss}$ HCT116 cells after α-Amanitin treatment. (FIG. 10G) Cell survival curves of POLR2A$^{neutral}$ and POLR2A$^{loss}$ HCT116 cells in response to the treatment of ama-HEA125.

(FIG. 11A) Quantification of POLR2A mRNA expression levels in subcutaneously xenografted HCT116 and SNU283 tumors expressing control or POLR2A shRNA (n=5 mice per group).  p<0.01. (FIG. 11B) Cells positive for Ki67 (cell proliferation) or cleaved caspase-3 (apoptosis) per field and POLR2A expression by immunohistochemical staining were quantified.  p<0.01. Data are mean and s.d. (FIG. 11C) Quantification of tumor sizes of xenograft tumors derived from subcutaneously implanted POLR2A$^{neutral}$ and POLR2A$^{loss}$ HCT116 cells ($1\times10^6$ cells injected). Both cell lines express control or Dox-inducible POLR2A shRNAs. After the initial establishment of tumors (100 mm$^3$), mice were treated with (0.5, 1, and 2 µg ml$^{-1}$) Dox in drinking water. n=5 mice per group. Data are mean and s.d.

(FIG. 12A) Western blots for POLR2A and β-Actin following transfection of control siRNA or POLR2A siRNAs (#1 and #2) in HCT116 cells. (FIG. 12B) Schematic illustration of orthotopic injection of HCT116 cells ($1\times10^6$ cells) followed by DOPC nanoliposome treatment intervals. (FIGS. 12C and 12D) Tumor growth curves of orthotopic xenograft tumors derived from POLR2A$^{neutral}$ and POLR2A$^{loss}$ HCT116 cells (FIG. 12C is siPol2-1; FIG. 12D is siPol2-2) that received intraperitoneal injections of control (1,000 µg kg$^{-1}$) or POLR2A siRNAs (125, 250, 500 and 1,000 µg kg$^{-1}$) twice weekly. n=10 mice per group. (FIGS. 12E and 12F) Representative protein levels of POLR2A and β-Actin in xenograft tumors following control or POLR2A siRNA treatment (FIG. 12E is siPol2-1; FIG. 12F is siPol2-2).

(FIGS. 13C AND 13D) Body weights (FIG. 13C) and liver enzymes (FIG. 13D) including alanine aminotransferase (ALT), aspartate aminotransferase (AST) and alkaline phosphatase in peripheral blood were recorded as described in Methods. Data shown are the means of five mice in each group.

(FIGS. 14A, 14C, and 14E) Protein levels of POLR2A and β-Actin in HCT116 (FIG. 14A), SW480 (FIG. 14C), or SW837 (FIG. 14E) cells. These cell lines are POLR2A-neutral, POLR2A-loss, or POLR2A-restored. (FIGS. 14B, 14D, and 14F) Tumor growth curves of orthotopic xenograft tumors derived from the corresponding cells as indicated. All of them received dual intraperitoneal injections of anti-EpCAM antibody (3.6 mg kg$^{-1}$) or ama-HEA125 antibody-drug conjugate (10 and 90 µg kg$^{-1}$, corresponding to 0.4 and 3.6 mg IgG kg$^{-1}$). n=10 mice per group.

DESCRIPTION OF ILLUSTRATIVE EMBODIMENTS

Figure 1A:
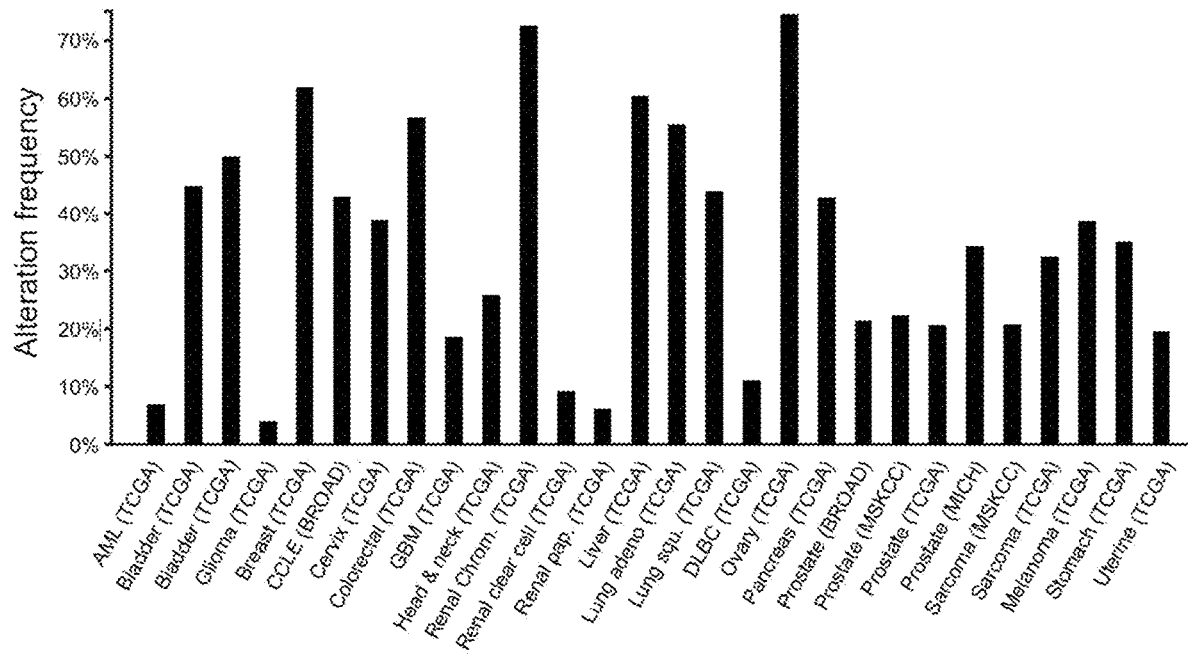
FIGS. 1A-H. Expression of POLR2A, but not TP53, is correlated with the gene copy number.

The studies provided herein demonstrate that genomic deletion of TP53 frequently encompasses neighbouring essential genes, rendering cancer cells with hemizygous TP53 deletion vulnerable to further suppression of such genes. POLR2A is identified as such an essential housekeeping gene that is virtually co-deleted with TP53 in many types of human cancer. It encodes the largest and catalytic subunit of RNA polymerase II complex, which is specifically inhibited by α-amanitin (Bensaude, 2011; Lindell et al., 1970). As such, instead of pharmacologic intervention of p53 or its regulators, the principle of collateral vulnerability to POLR2A inhibition provides a brand-new strategy for cancer therapy.

The present analysis of clinical samples and cancer cell lines in The Cancer Genome Atlas (TCGA) and Cancer Cell Line Encyclopaedia (CCLE) reveals that POLR2A expression levels are tightly correlated with its gene copy numbers in human colorectal tumors. Suppression of POLR2A with α-amanitin, small interfering RNAs, or short-hairpin RNAs, selectively inhibited proliferation, survival, and tumorigenic potential of colorectal cancer cells with hemizygous TP53 loss in a p53-independent manner. Moreover, the present preclinical studies with α-amanitin predict therapeutic efficacy of α-amanitin-based drugs or inhibitors against POLR2A for treating colorectal cancer and it should be applicable to many types of human cancers with hemizygous loss of TP53.

Previous clinical applications of α-amanitin have been limited due to its liver toxicity (Letschert et al., 2006). Free α-amanitin is toxic to liver because it is specifically bound by OATP1B3, a transporter exclusively expressed on the membrane of hepatocytes (Letschert et al., 2006). However, α-amanitin, when conjugated with specific antibodies, is no longer a substrate for OATP1B3 (Letschert et al., 2006; Moldenhauer et al., 2012; Faulstich and Fiume, 1985). Here, it is shown that low doses of an α-amanitin-antibody conjugate (e.g., α-Amanitin-conjugated anti-EpCAM (Epithelial Cell Adhesion Molecule) antibody) lead to tumor regression in murine models of human colorectal cancer with hemizygous deletion of POLR2A. Inhibiting POLR2A is a novel therapeutic approach for cancers harbouring such common genomic alterations.

I. CELL-TARGETING CONJUGATES

It may be desired to conjugate an α-amanitin molecule (or any amatoxin) to at least one cell-targeting agent to enhance the utility of α-amanitin and reduce liver toxicity. Such a conjugate may be termed an "immunotoxin." For example, in order to increase the efficacy and utility of α-amanitin as a therapeutic agent, it may be conjugated or covalently bound to a desired cell targeting moiety. Such a moiety may be any moiety with sufficient selectivity, specificity, or affinity for targeting a desired cell type by binding to an external receptor or binding site on said cell types, such as a cancer cell (U.S. Patent Publn. No. 2009/0304666). Examples of such moieties include, but are not limited to, antibodies or antigen-binding fragments thereof, antibody-like proteins, and aptamers. Examples of antigen-binding antibody fragments include without limitation: (i) the Fab fragment, consisting of VL, VH, CL and CH1 domains; (ii) the "Fd" fragment consisting of the VH and CH1 domains; (iii) the "Fv" fragment consisting of the VL and VH domains of a single antibody; (iv) the "dAb" fragment, which consists of a VH domain; (v) isolated CDR regions; (vi) F(ab')2 fragments, a bivalent fragment comprising two linked Fab fragments; (vii) single chain Fv molecules ("scFv"), wherein a VH domain and a VL domain are linked by a peptide linker that allows the two domains to associate to form a binding domain; (viii) bi-specific single chain Fv dimers (see U.S. Pat. No. 5,091,513) and (ix) diabodies, multivalent or multispecific fragments constructed by gene fusion (U.S. Patent Publn. No. 2005/0214860). Fv, scFv or diabody molecules may be stabilized by the incorporation of disulfide bridges linking the VH and VL domains. A cell targeting moiety may specifically bind to any tumor-associated antigen, such as, for example, CD19, CD20, CD30, CD33, CD52, EpCAM, carcinoembryonic antigen, alphafetoprotein, gpA33, Mucins, CA-125, MUC-1, CD56, EGFR, ERBB2, ERBB3, c-Met, IGF1R, EPHA3, TRAILR1, TRAILR2, RANKL, FAP, Tenascin, AKT, Her2/neu, Her3, epithelial tumor antigen, melanoma-associated antigen, mutated p53, mutated ras, Dectin-1, gp100, MART-1/MelanA, TRP-1 (gp75), Tyrosinase, TAG-72, CAIX, PSMA, Folate-binding protein, gangliosides (e.g., GD2, GD3, GM2), MAGE-1, MAGE-3, BAGE, GAGE-1, GAGE-2, N-acetylglucosaminyltransferase-V, p15, β-catenin, MUM-1, CDK4, HPV-E6, HPV-E7, ZFP161, Ubiquilin-1, HOX-B6, IFI27, YB-1, KIAA0136, Osteonectin, F-box only protein 21, ILF3, SSX-2, PSMA, NY-ESO-1, PRAME, mesothelin, VEGF, VEGFR, Integrin alphaVbeta3, Integrin alpha5beta1, or PLK1.

Several methods are known in the art for the attachment or conjugation of a cell targeting moiety (e.g., a tumor-associated antigen directed antibody) to a conjugate (e.g., α-amanitin) (see PCT Publn. WO2012/119787, which is incorporated herein by reference in its entirety). For example, an immunotoxin may employ a cleavable disulfide linker well known in the art. The toxin may be conjugated to the cell targeting moiety by treating the toxin to provide sulfhydryl groups and the cell targeting moiety to provide pyridyl disulfide residues. Other linkages that are commonly utilized and expected to be useful for conjugating a toxin to cell targeting moieties are imminothiolane/succinimidyl 4-(N-maleimidomethyl) cyclohexane-1-carboxylate and carbodiimide linkages. Many other linkages for conjugating proteins of varying lengths, stability, flexibility and chemical reactivity are well known in the art and in many cases are commercially available. Some examples of attachment methods involve the use of a disulfide exchange reaction; by forming a thioether bond; a metal chelate complex employing, for example, an organic chelating agent, such a diethylenetriaminepentaacetic acid anhydride (DTPA); ethylenetriaminetetraacetic acid; N-chloro-p-toluenesulfonamide; and/or tetrachloro-3-6α-diphenylglycouril-3 attached to the cell targeting moiety. Cell targeting moieties may also be reacted with an enzyme in the presence of a coupling agent such as glutaraldehyde or periodate. It is desirable that any α-amanitin-cell targeting moiety conjugate be stable upon extended exposure to serum. As such, α-amanitin may be conjugated to a lysine residue of a cell targeting moiety by way of a stable urea linker that is serum-stable but will release free α-amanitin inside of a targeted cell following lysosomal degradation of the cell targeting moiety.

II. TREATMENT OF DISEASE

Certain aspects of the present embodiments can be used to prevent or treat a disease or disorder associated with hemizygous loss of TP53 and associated loss of POLR2A. Functioning of POLR2A may be reduced by any suitable substances to treat a cancer harboring hemizygous loss of TP53 and/or POLR2A. Such exemplary substances can be any amatoxin, α-amanitin, or cell-targeting moieties conjugated to any amatoxin or α-amanitin.

A cancer harboring hemizygous loss of TP53 and/or POLR2A may not be homogenous with regard to the loss of TP53 and/or POLR2A. In various aspects, about 5%, 10%, 15%, 20%, 25%, 30%, 35%, 40%, 45%, 50%, 55%, 60%, 65%, 70%, 75%, 80%, 85%, 90%, 95%, or 100% of the cells that comprise the cancer may harbor a hemizygous loss of TP53 and/or POLR2A. Thus, in some aspects, about 5%, 10%, 15%, 20%, 25%, 30%, 35%, 40%, 45%, 50%, 55%, 60%, 65%, 70%, 75%, 80%, 85%, 90%, 95%, or 99% of the cells that comprise the cancer may comprise both copies of TP53 and/or POLR2A. In other aspects, various percentages of cells comprising the cancer may harbor a homozygous loss of TP53 and a hemizygous loss of POLR2A.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of an substance that inhibits the function POLR2A.

A "subject" refers to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

An α-amanitin conjugate may be administered to treat a cancer. Cancers for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); and chronic myeloblastic leukemia.

III. COMBINATION TREATMENTS

In certain embodiments, the compositions and methods of the present invention involve cell-targeting moieties conjugated to α-amanitin, in combination with a second or additional therapy. Such therapy can be applied in the treatment of any disease that is associated with hemizygous loss of TP53 and/or POLR2A. For example, the disease may be a cancer.

The methods and compositions including combination therapies enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both a cell-targeting moiety conjugated to α-amanitin and a second therapy. A tissue, tumor, or cell can be contacted with one or more compositions or pharmacological formulation(s) including one or more of the agents (i.e., an anti-cancer agent), or by contacting the tissue, tumor, and/or cell with two or more distinct compositions or formulations, wherein one composition provides 1) a cell-targeting moiety conjugated to α-amanitin; 2) an anti-cancer agent, or 3) both a cell-targeting moiety conjugated to α-amanitin and an anti-cancer agent. Also, it is contemplated that such a combination therapy can be used in conjunction with a chemotherapy, radiotherapy, surgical therapy, or immunotherapy.

The terms "contacted" and "exposed," when applied to a cell, are used herein to describe the process by which a therapeutic antibody and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

A cell-targeting moiety conjugated to α-amanitin may be administered before, during, after or in various combinations relative to an anti-cancer treatment. The administrations may be in intervals ranging from concurrently to minutes to days to weeks. In embodiments where the inhibitor of gene expression is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the cell-targeting moiety conjugated to α-amanitin and the anti-cancer therapy within about 12 to 24 or 72 h of each other and, more particularly, within about 6-12 h of each other. In some situations it may be desirable to extend the time period for treatment significantly where several days (2, 3, 4, 5, 6 or 7) to several weeks (1, 2, 3, 4, 5, 6, 7 or 8) lapse between respective administrations.

In certain embodiments, a course of treatment will last 1-90 days, or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below a cell-targeting moiety conjugated to α-amanitin therapy is "A" and an anti-cancer therapy is "B":

A/B/AB/A/BB/B/AA/A/BA/B/BB/A/AA/B/B/BB/A/B/B
B/B/B/A B/B/A/B A/A/B/B A/B/A/BA/B/B/AB/B/A/A
B/A/B/A B/A/A/B A/A/A/BB/A/A/AA/B/A/AA/A/B/A

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy.

In specific aspects, it is contemplated that a standard therapy will include chemotherapy, radiotherapy, immunotherapy, surgical therapy or gene therapy and may be employed in combination with the inhibitory antibody, anti-cancer therapy, or both the inhibitory antibody and the anti-cancer therapy, as described herein.

A. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK-polysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; carboplatin, procarbazine, plicomycin, gemcitabien, navelbine, farnesyl-protein transferees inhibitors, transplatinum, and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene; aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor and a HER2 expression inhibitor; vaccines such as gene therapy vaccines and pharmaceutically acceptable salts, acids or derivatives of any of the above.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287) and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

C. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

Another immunotherapy could also be used as part of a combined therapy with gene silencing therapy discussed above. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including cytokines, such as IL-2, IL-4, IL-12, GM-CSF, and gamma-IFN, chemokines, such as MIP-1, MCP-1, and IL-8, and growth factors, such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds can be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739,169; Hui and Hashimoto, 1998; Christodoulides et al., 1998), cytokine therapy, e.g., interferons α, β and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Hanibuchi et al., 1998; U.S. Pat. No. 5,824,311).

It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant. In adoptive immunotherapy, the patient's circulating lymphocytes, or tumor infiltrated lymphocytes, are isolated in vitro, activated by lymphokines, such as IL-2, or transduced with genes for tumor necrosis, and re-administered.

D. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that certain aspects of the present invention may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be used in combination with certain aspects of the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increase of intercellular signaling by elevating the number of GAP junctions would increase the anti-hyperproliferative effects on the neighboring hyperproliferative cell population. In other embodiments, cytostatic or differentiation agents can be used in combination with certain aspects of the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present invention to improve the treatment efficacy.

Hormonal therapy may also be used in conjunction with certain aspects of the present invention or in combination with any other cancer therapy previously described. The use of hormones may be employed in the treatment of certain cancers such as breast, prostate, ovarian, or cervical cancer to lower the level or block the effects of certain hormones, such as testosterone or estrogen. This treatment is often used in combination with at least one other cancer therapy as a treatment option or to reduce the risk of metastases.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Cell Culture, Antibodies, and Western Blot Analysis.

HCT116, SW480, SW837, HT29, DLD1, and HT29 cell lines were obtained from the American Type Culture Collection and cultured under standard conditions specified by the manufacturer. SNU283 and SNU1197 cell lines were obtained from the Korean Cell Line Bank and cultured in RMPI 1640 medium supplemented with 10% FBS and 2 mM L-Glutamine. Isolation, culture and maintenance of xenografted human primary CRC (xhCRC) cells were performed as previously described (Lu et al., 2013). Briefly, the patient-derived xenografts were harvested under sterile conditions and mechanically dissociated, followed by 30 min of incubation in collagenase II at 37° C. The specimen was filtered through a sterile 100-µm strainer. Red blood cells were eliminated with a hypo-osmotic red blood cell lysis buffer (eBioscience). Mouse cells in xenografted human CRC specimens were removed by negative selection using a mouse MHC class I molecule H-2K antibody followed by use of a magnetic bead purification kit (Miltenyi). Fibroblasts were removed by negative selection using a MACS magnetic bead separation kit (Miltenyi). The freshly isolated xhCRC cells were maintained on Collagen-1 coated culture plates (BD Biosciences) and cultured in MEM supplemented with 10% FBS, vitamins (1×), nonessential amino acids (1×), Pen-Strep (1×), sodium pyruvate (1×), and L-glutamine (1×). All medium supplements were purchased from Sigma.

Anti-POLR2A antibodies were purchased from Santa Cruz (#sc-47701) and Abcam (#ab140509). Anti-Ki67 antibody (#D3B5) and anti-cleaved Caspase-3 (Asp175, #5A1E) antibody were obtained from Cell Signalling. Anti-p53 (#sc-126), anti-β-actin (#sc-1616), HRP-anti-goat IgG (#sc-2020), HRP-anti-rabbit IgG (#sc-2054), and HRP-anti-mouse IgG (#sc-2055) antibodies were purchased from Santa Cruz. Cell lysate preparation, SDS-PAGE, and Western blotting were performed as previously described (Liu et al., 2012).

RNA Isolation and Quantitative PCR.

Total RNA was isolated using TRIzol reagent (Life Technologies) and then reverse-transcribed using iScript cDNA Synthesis Kit (Bio-Rad). The resulting cDNA was used for qPCR using iTaq Universal SYBR Green Supermix (Bio-Rad) with gene-specific primers and the results were normalized to β-actin as a control. In RT-PCR assays, the primer sequences for TP53 are: 5'-GAGGTTGGCTCTGACTG-TACC-3' (SEQ ID NO: 1) and 5'-TCCGTCCCAGTAGAT-TACCAC-3' (SEQ ID NO: 2), and for POLR2A are: 5'-TT-GTATCCGTACCCACAGCA-3' (SEQ ID NO: 3) and 5'-CATGATCAGCTCCCCATTCT-3' (SEQ ID NO: 4).

shRNA-Mediated Knockdown of POLR2A.

POLR2A-specific shRNA clones were obtained from the MD Anderson shRNA and ORFeome Core Facility (originally from Open Biosystems). Twelve shRNAs targeting POLR2A were screened, of which two shRNAs knocked down protein levels by at least 50% in all four colorectal cancer cell lines tested. The clone identification numbers and shRNA sequences are V3LHS_645674 (5'-TTAGCTTTGT-TCTTCCCGA-3' [SEQ ID NO: 5]) and V3LHS_64029 (5'-TGTTGTCCATCTCCTCCCC-3' [SEQ ID NO: 6]). The hairpin sequences in the GIPZ vector were cloned into the TRIPZ vector (Dharmacon) using a protocol provided by the manufacturer. The TRIPZ vector is a Dox-inducible system with a red fluorescent protein reporter.

Generation of Cells Stably Expressing Dox-Inducible shRNAs.

Recombinant lentiviral particles were produced from 293T cells. Briefly, 72 µg of shRNA-encoding vector DNA, 54 µg of Delta 8.9 vector DNA and 18 µg of VSVG-encoding vector DNA were transfected into 293T cells (plated in the 245-mm$^2$ dish) using X-tremeGENE (Roche). Supernatant containing virus particles was collected and filtered 72 h after transfection, concentrated by ultracentrifugation at 90,000 g, and resuspended in cell growth medium. To generate stable Dox-inducible cells, HCT116 and SNU283 cells were infected with shRNA-expressing viral particles at the multiplicity of infection (MOI) of 1. Viral solutions were added to cell culture medium containing 4 µg/mL polybrene. Cells were selected 48 h after infection by 2 µg/mL puromycin. Single colonies were cultured and propagated, and colonies bearing a single copy of lentiviral DNA insert were identified and analyzed for knockdown efficiency.

Competition Assay Using POLR2A shRNA.

Figure 6A:
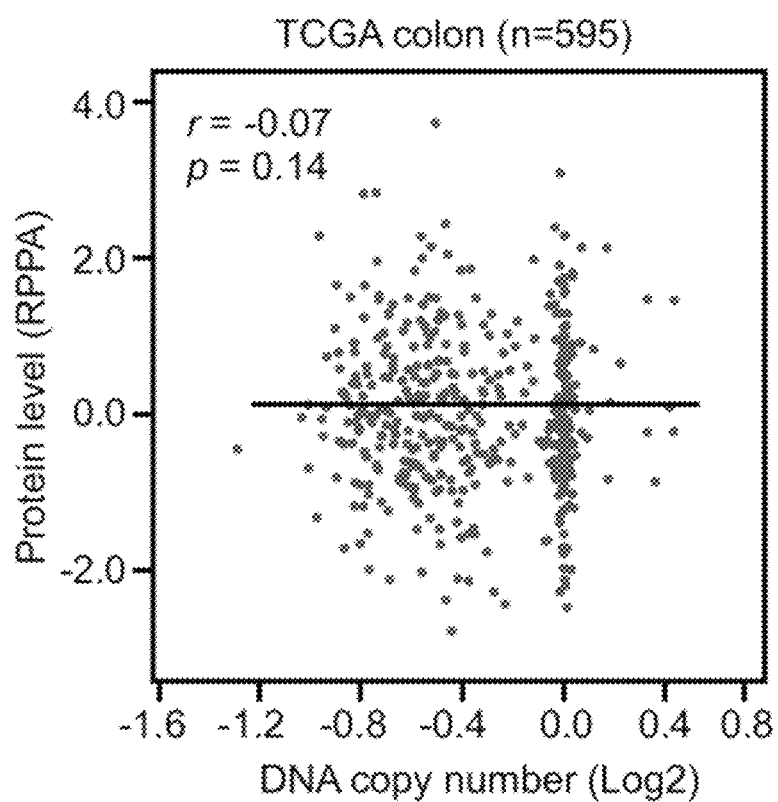
FIGS. 6A-C. Expression of TP53 is not associated with its gene copy number.
Figure 6B:
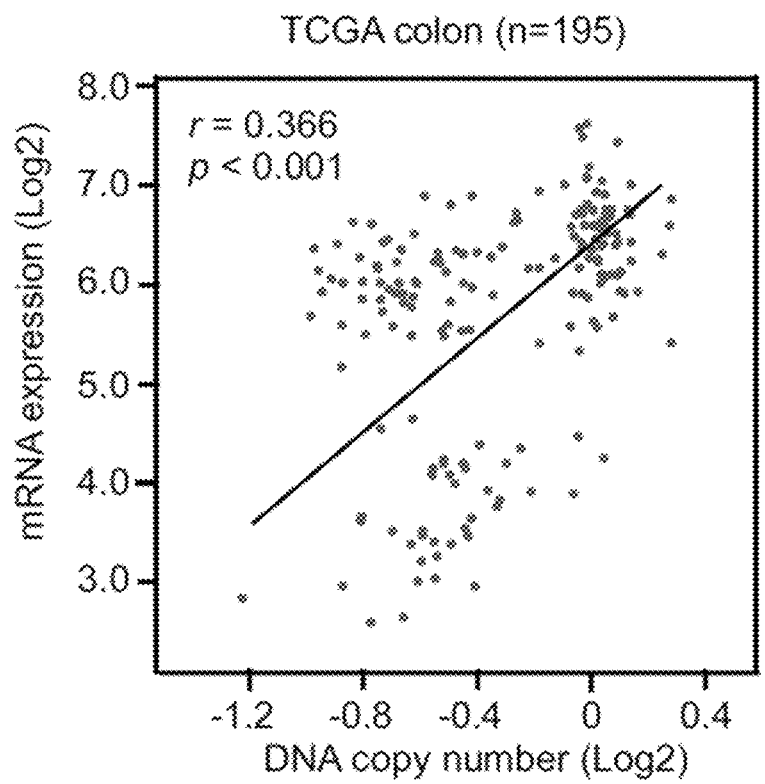
Figure 6C:
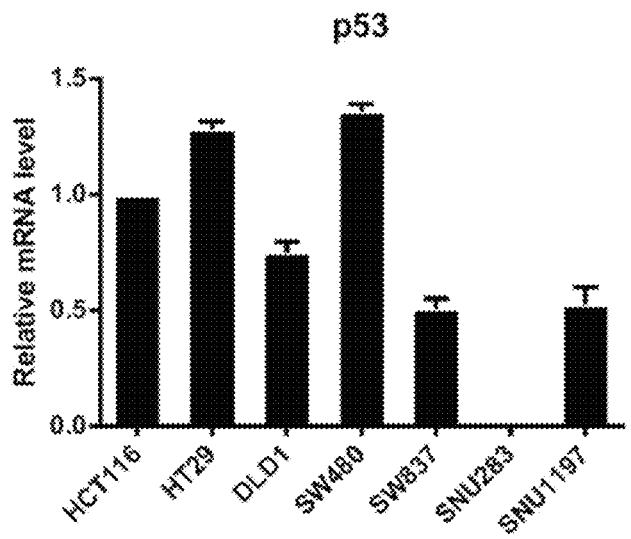

A single lentiviral copy expressing either shRNA-1 or shRNA-2 was sufficient to suppress POLR2A expression levels in all the four colorectal cell lines tested (FIG. 6A). Cancer cells were infected with control or POLR2A shRNA-expressing lentiviruses (pGIPZ backbone expressing GFP) at the MOI of 2. Two days after infection, GFP-positive cells were sorted using a BD FACSJazz™ cell sorter (BD Biosciences) at the MD Anderson Flow Cytometry and Cellular Imaging Core Facility. Next, GFP-positive cells were mixed with non-infected and GFP-negative cells at the ratio of 1:1 and cultured for six passages. The numbers of GFP-positive and total cells at each passage were analyzed and quantified by flow cytometry and the percentages of GFP-positive cells were calculated.

Generation of sgRNA-Expressing Vectors and Surveyor Assay.

Bicistronic expression vector expressing Cas9 and sgRNA was digested with BbsI and treated with alkaline phosphatase, and the linearized vector was gel purified for cloning sgRNA-encoding DNA (Cong et al., 2013). The pair of oligo DNA for each sgRNA targeting TP53 or POLR2A was annealed, phosphorylated, and ligated to the linearized vector. The sequences of oligo DNA are listed in Table 1. Surveyor assay was performed to test the genome editing efficacy as previously described (Ran et al., 2013; Guschin et al., 2010). Briefly, cells were seeded into six-well plates at a density of $2 \times 10^5$ cells per well. One day after initial seeding, cells were transfected with 2 µg of Cas9/sgRNA-expressing vector DNA and harvested 48 h after transfection. Genomic DNA was isolated and a 1 kb DNA fragment containing the sgRNA-targeting site was amplified by high-fidelity PCR and digested by T7 endonuclease I. Genomic DNA isolated from HCT116 cells transfected with control vector DNA was used as control. To allow complementary but mismatched strands to anneal, PCR products were incubated at 95° C. for 5 min, 95° C. to 85° C. at the rate of $-2°$ C. $s^{-1}$ and 85° C. to 25° C. at the rate of $-0.1°$ C. $s^{-1}$. T7 endonuclease I was added and samples were incubated at 37° C. for 60 min to digest the annealed PCR products at the mismatch sites. T7 endonuclease I-digested PCR products were analyzed by agarose gel electrophoresis. Oligonucleotide sequences used for PCR amplification are listed in Table 1. The PCR products from positive clones were ligated to pGEM-T Easy Vector (Promega) and further confirmed by DNA sequencing.

reagent (Roche) according to the manufacturer's instructions. All experiments were performed in triplicate.

Apoptosis and Cell Cycle Analysis.

The HCT116 and SNU283 cell lines were treated with or without α-Amanitin for 2 d or doxycycline for 4 d at indicated concentrations and stained with annexin V-PE and 7-AAD (Biovision). Apoptosis was analyzed by flow cytometry using a Guava EasyCyte Flow Cytometer (Millipore) according to the manufacturer's protocol. Both pre-apoptotic (annexin V-positive and 7-AAD-negative) and apoptotic (annexin V-positive and 7-AAD-positive) cells were included in the analyzes. For cell cycle analysis, cells were fixed in 75% ethanol at $-20°$ C. overnight. The cells were washed with cold PBS, treated with 100 µg of RNase A (Qiagen), and stained with 50 µg of propidium iodide (Roche). Cell cycle profiles were analyzed by flow cytometry using the Guava EasyCyte Flow Cytometer (Millipore).

Fluorescence In Situ Hybridization (FISH).

FISH analysis was performed using Fluorescein-labelled POLR2A (red) and control centromere (Chr 17, green) probes from Empire Genomics. Hybridization and detection were performed according to the manufacturer's protocols. The slides were counterstained with DAPI, and the images

TABLE 1

Sequence of oligonucleotides for sgRNAs and Surveyor assays.

| Name | Genomic target | Sequence | SEQ ID NO: | Assay |
|---|---|---|---|---|
| Pol-sp1F | POLR2A | caccgCGGCCTCCCTCAGTCGTCTC | 7 | sgRNA |
| Pol-sp1R | POLR2A | aaacGAGACGACTGAGGGAGGCCGC | 8 | sgRNA |
| Pol-sp2F | POLR2A | caccGGCCGCTGCCAAACATGTGC | 9 | sgRNA |
| Pol-sp2R | POLR2A | aaacGCACATGTTTGGCAGCGGCC | 10 | sgRNA |
| Pol-gDNAF | POLR2A | AAAATCTCCATCTGGACACGAAAGG | 11 | Surveyor |
| Pol-gDNAR | POLR2A | AGCGCAAAACTTTCATTGTCTTCAC | 12 | Surveyor |
| p53-spF1F | TP53 | caccgCCATTGTTCAATATCGTCCG | 13 | sgRNA |
| p53-spR1R | TP53 | aaacCGGACGATATTGAACAATGGC | 14 | sgRNA |
| p53-spF2F | TP53 | caccGGGCAGCTACGGTTTCCGTC | 15 | sgRNA |
| p53-spR2R | TP53 | aaacGACGGAAACCGTAGCTGCCC | 16 | sgRNA |
| p53-gDNAF | TP53 | GAGGAGCCGCAGTCAGATCCTA | 17 | Surveyor |
| p53-gDNAR | TP53 | GATACGGCCAGGCATTGAAGTC | 18 | Surveyor |

Cell Proliferation and Survival Assay.

Equal numbers of cells were plated in 12-well plates in triplicate. Cells were fixed with 10% methanol and stained with 0.1% crystal violet (dissolved in 10% methanol) at indicated times. After staining, wells were washed three times with PBS and destained with acetic acid. The absorbance of the crystal violet solution was measured at 590 nm. For cell survival assay, cells were seeded at a concentration of 1,000 cells per well in 96-well plates and treated with indicated concentrations of α-Amanitin or actinomycin D 24 hours later. Cell viability was quantified using WST-1 were captured using a Nikon E800 microscope equipped with a cooled-charge coupled device (CCD) camera. To determine hemizygous loss of the POLR2A gene, 100 individual nuclei were analyzed for each case. The interphase nuclei were captured and processed using the Quantitative Image Processing System (Applied Imaging).

Patient Samples.

Matched normal and colorectal tumor tissue samples from patients were obtained from the MD Anderson Cancer Center (MDACC) through appropriate informed consents after approval by the institutional review board (IRB#

PA11-0767). To determine the expression levels of POLR2A protein, tissue samples (20-40 mg) were placed in tubes containing ceramic beads and were homogenized using a Precellys 24 homogenizer device (Bertin Technologies). The lysates were spun-down twice (15 min, 16,000 g) and the supernatant was collected.

Genomic DNA Isolation and Copy Number Validation.

Total genomic DNA was extracted from human tissue specimens and cell lines using DNeasy Blood & Tissue Kit (Qiagen) according to the manufacturer's purification instructions. All the DNA samples were stored at −20° C. The copy number variations for POLR2A were determined using TaqMan probes (Hs02023849_cn and Hs01252684_cn) and standard TaqMan PCR kit on an Applied Biosystems 7900HT Sequence Detection System. And the reference gene TERT was simultaneously quantified in the same tube for each DNA sample.

Conjugation of α-Amanitin to Anti-EpCAM Antibody (HEA125).

Antibody-drug conjugate ama-HEA125 was constructed by coupling of α-Amanitin to lysine residues of HEA125 antibody by a stable linker structure. HEA125 binds to EpCAM-expressing cells with high affinity ($K_D$ of approximately $2.2 \times 10^{-9}$ M) and high specificity. HEA125 was purified by affinity chromatography using a protein A-Sepharose CL-4B column (GE Healthcare). α-Amanitin was attached to immunoglobulin molecules by a plasma stable urea linkage intended to release free α-Amanitin inside the tumor cell after lysosomal degradation of the antibody moiety. The drug-antibody ratio (DAR) of the α-Amanitin:IgG molecule was 4:1. Biochemical characteristics of ama-HEA125 were evaluated by high performance liquid chromatography (HPLC) using a PlatinBlue HPLC system (Knauer). In addition, HEA125 and ama-HEA125 were analyzed by reducing SDS-PAGE and Coomassie staining according to common procedures. Verification of drug-loading was done by anti-amanitin immunoblotting analysis of 30 ng HEA125 and ama-HEA125 using standard techniques.

Liposomal Nanoparticle Preparation.

siRNAs for in vivo delivery were encapsulated into DOPC (1,2-dioleoyl-sn-glycero-3-phosphatidylcholine). DOPC and siRNA were mixed in the presence of excess tertiary butanol at a ratio of 1:10 (w/w) siRNA/DOPC. Tween 20 was added to the mixture in a ratio of 1:19 Tween 20:siRNA/DOPC. The mixture was vortexed, frozen in an acetone/dry ice bath, and lyophilized. Prior to in vivo administration, this preparation was hydrated with PBS at room temperature at a concentration of 150-1000 µg siRNA/kg per injection (each mouse received 200 µL of DOPC:siRNA:PBS solution by the intraperitoneal route).

Xenograft Tumor Studies.

Four- to six-week-old female NOD/SCID mice were purchased from Jackson Laboratories and housed under pathogen-free conditions. All studies were approved and supervised by the Institutional Animal Care and Use Committee of MD Anderson Cancer Center. When used in a power calculation, the present sample size predetermination experiments indicated that 5 mice per group can identify the expected effect of POLR2A on tumor size and weight ($p<0.05$) with 90% power. Animals were randomly divided to different groups. Dox-inducible HCT116 ($1 \times 10^6$) and SNU283 ($2 \times 10^6$) cells in 50 µl growth medium (mixed with Matrigel at 1:1) were injected subcutaneously into the flank using a 100-µl Hamilton microliter syringe. Tumor size was measured every five days using a caliper, and tumor volume was calculated using the standard formula: $0.5 \times L \times W^2$, where L is the longest diameter and W is the shortest diameter. For orthotopic mouse model, the SCID mice were anaesthetized and the skin was incised to expose cecum. Dox-inducible HCT116 cells ($1 \times 10^6$) expressing luciferase were injected into the cecal wall using a 100-µl Hamilton microliter syringe, and then the incision was closed using wound clips. Tumors were monitored by the IVIS system after luciferin injection for 15 min. After initial establishment of tumor (100 mm³ for subcutaneous implants and $2 \times 10^8$ photons/second, total flux for orthotopic implants), mice were treated with 1 µg ml$^{-1}$ doxycycline in drinking water for 3 to 4 weeks. The doxycycline water was changed every other day.

For xenograft tumor studies using DOPC-encapsulated siRNAs, isogenic pairs of HCT116 ($1 \times 10^6$) cells were transplanted into the cecal wall using a 100-µl Hamilton microliter syringe. Ten days following cell injection, mice were randomly divided and assigned to receive either control siRNA-DOPC or POLR2A siRNA-DOPC. The siRNA sequences are as follows: control siRNA (5'-UUCUC-CGAACGUGUCACGU-3' [SEQ ID NO: 19] and 5'-ACGUGACACGUUCGGAGAA-3' [SEQ ID NO: 20]); POL2 siRNA-1 (5'-CCAACAUGCUGACAGAUAU-3' [SEQ ID NO: 21] and 5'-AUAUCUGUCAGCAUGUUGG-3' [SEQ ID NO: 22]); POL2 siRNA-2 (5'-CCAAGAAGCG-GCUCACACA-3' [SEQ ID NO: 23] and 5'-UGU-GUGAGCCGCUUCUUGG-3' [SEQ ID NO: 24]). A dose of 150 to 1000 µg siRNA/kg mouse was administrated intraperitoneally at twice weekly intervals. This range of concentrations ensures efficient delivery and knockdown of target genes, as previously described (Pecot et al., 2014).

For xenograft tumor studies using α-Amanitin-HEA125 antibody-drug conjugate (ADC), isogenic pairs of HCT116 ($1 \times 10^6$), xhCRC ($0.5 \times 10^6$), SW480 ($1 \times 10^6$) or SW837 ($2 \times 10^6$) cells were transplanted into the cecal wall using a 100-µl Hamilton microliter syringe. Mice bearing 10-day-old tumors were randomized to five groups (n=10 mice/group) and received two intraperitoneal doses (1 week apart) of the following: 1) control unconjugated HEA125 mAb at a dose of 3.6 mg kg$^{-1}$ of body weight; 2) Ama-HEA125 at a dose of 90 µg kg$^{-1}$ in terms of α-Amanitin (corresponding to 3.6 mg kg$^{-1}$ of IgG); 3) Ama-HEA125, 30 µg kg$^{-1}$ in terms of α-Amanitin (corresponding to 1.2 mg kg$^{-1}$ of IgG); 4) Ama-HE125, 10 µg kg$^{-1}$ in terms of α-Amanitin (corresponding to 0.4 mg kg$^{-1}$ of IgG); and 5) Ama-HEA125, 3 µg kg$^{-1}$ in terms of α-Amanitin (corresponding to 0.12 mg kg$^{-1}$ of IgG). Tumors were monitored by the IVIS live imaging system twice a week after luciferin injection for 15 min. Body weights were recorded every four days. Blood was obtained by retro-orbital bleeding after anesthesia on day 21 and levels of blood liver enzymes (AST: aspartate amino transferase, ALT: amino alanine transferase and alkaline phosphatase) were determined at the Clinical Pathology, Veterinary Medicine and Surgery Core of MD Anderson Cancer Center.

Mice were euthanized when they met the institutional euthanasia criteria for tumor size and overall health condition. Tumors were removed, photographed and weighed. The freshly dissected tumor tissues were fixed in 10% buffered formalin overnight, washed with PBS, transferred to 70% ethanol, embedded in paraffin, sectioned and stained with haematoxylin and eosin. The investigators were blinded to the group allocation during the experiment and when assessing the outcome.

Immunohistochemistry and Human Colon Tissue Microarray.

Colon cancer tissue microarray (BC051110a) was purchased from Biomax, including 110 colon tumor samples and 10 normal colon tissue samples. Samples were deparaffinized and rehydrated. Antigen was retrieved using 0.01 M sodium-citrate buffer (pH 6.0) at a sub-boiling temperature for 10 min after boiling in a microwave oven. To block endogenous peroxidase activity, the sections were incubated with 3% hydrogen peroxide for 10 min. After 1 h of pre-incubation in 5% normal goat serum to prevent nonspecific staining, the samples were incubated with antibody against POLR2A (#sc-47701, Santa Cruz), Ki67, (#D3B5, Cell Signaling), or cleaved Caspase-3 (#5A1E, Cell Signaling) at 4° C. overnight. The sections were incubated with a biotinylated secondary antibody (4Plus Biotinylated anti-mouse or anti-rabbit IgG, BioCARE) and then incubated with avidin-biotin peroxidase complex solution and developed using a DAB (diaminobenzidine) Substrate Kit (#550880, BD Biosciences) according to the manufacturer's protocol. Counterstaining color was carried out using Harris modified haematoxylin. All immunostained slides were scanned on the Automate Cellular Image System III (ACIS III) for quantification by digital image analysis.

Bioinformatic Analysis.

The correlation between gene copy number and the corresponding gene expression was analyzed using data obtained from CCLE (on the world wide web at broadinstitute.org/ccle) and TCGA (on the world wide web at cbioportal.org/public-portal/) as previously described (Nijhawan et al., 2012). Enrichment of Pearson correlation coefficients was determined by permuting gene names. To determine whether a deleted gene functions as a housekeeping gene, its expression profiles in tumor and normal tissues as well as its general functions from literature were first analyzed. Second, gene conservation across species and lethality of the gene knockout were checked by searching available databases of model organisms (Saccharomyces Genome Database, WormBase, FlyBase, and Mouse Genome Informatics). Third, the proximity of the potential target gene to the TP53 gene was checked and its co-deletion with TP53 in human cancers was analyzed. Finally, cancer cell lines with the deletion of TP53 and the target gene were identified to test the present hypothesis.

Statistical Analysis.

Each experiment was repeated three times or more. Unless otherwise noted, data are presented as mean and s.d. or s.e.m., and Student's t-test (unpaired, two-tailed) was used to compare two groups of independent samples. In an unpaired t-test, equal variance was assumed and no samples were excluded from the analysis. Statistical methods used for TCGA data analysis are described above. $p<0.05$ was considered statistically significant.

Figure 1B:
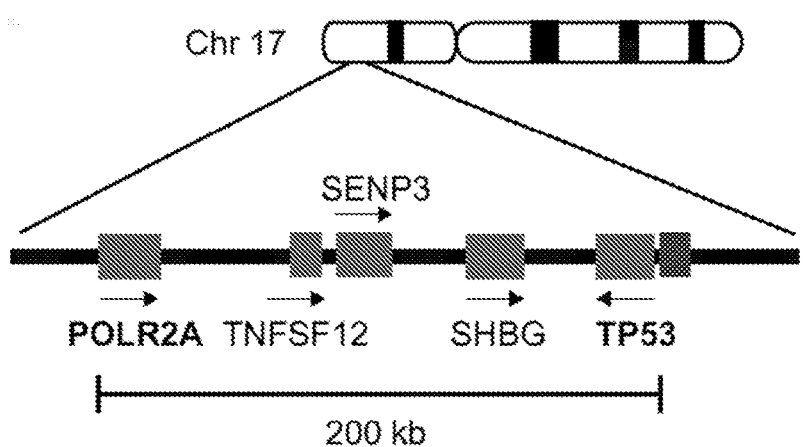
Figure 1C:
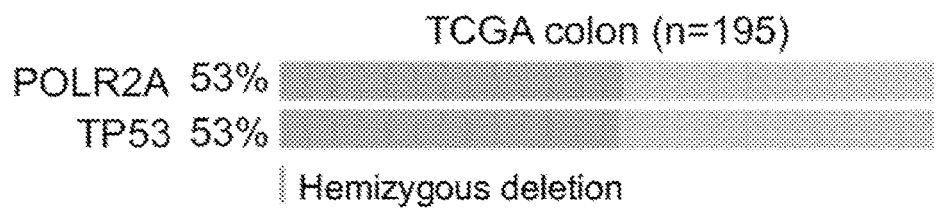

Example 1—Expression of POLR2A, but not TP53, is Correlated with Gene Copy Number Genomic deletion of a tumor suppressor gene often encompasses multiple neighboring genes that may not contribute to cancer development, but are essential for cell proliferation and survival (Negrini et al., 2010). This partial loss of such housekeeping genes has been postulated to render cancer cells highly vulnerable to further inhibition of those genes (Nijhawan et al., 2012). Analysis of TCGA revealed that hemizygous deletion of the TP53 gene occurs frequently in a wide array of human cancers (FIG. 1A). POLR2A was identified as a housekeeping gene in the proximity of TP53 (residing ~200 kilobases away in human genome) that is essential for cell survival (FIG. 1B). Concomitant deletion of POLR2A occurs in virtually all the human colorectal tumors harbouring hemizygous deletion of TP53 (FIG. 1C).

Figure 1D:
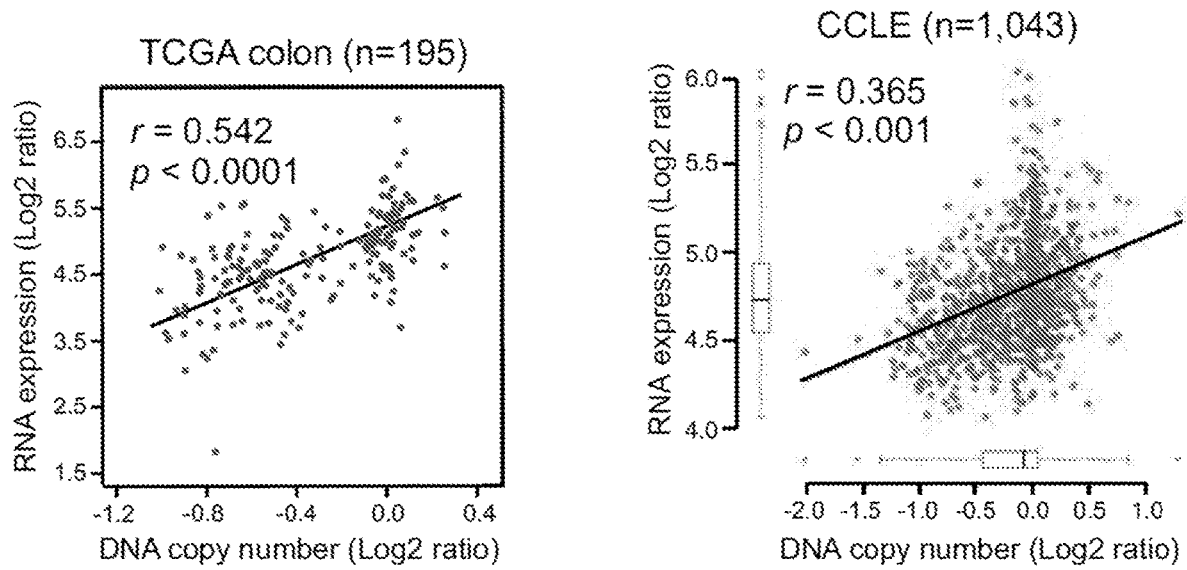
Figure 1E:
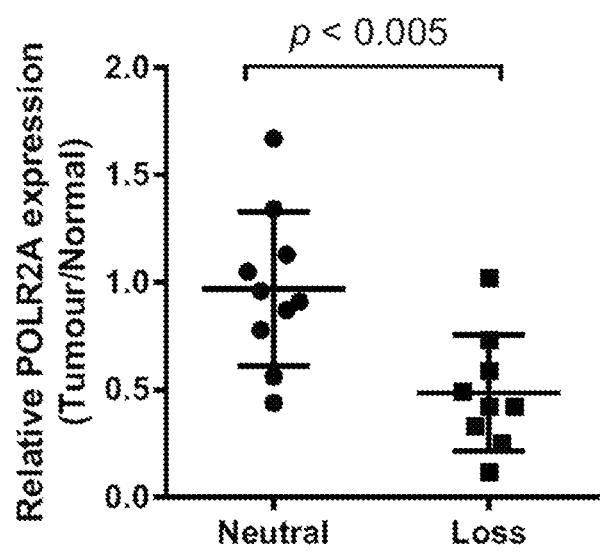
Figure 1F:
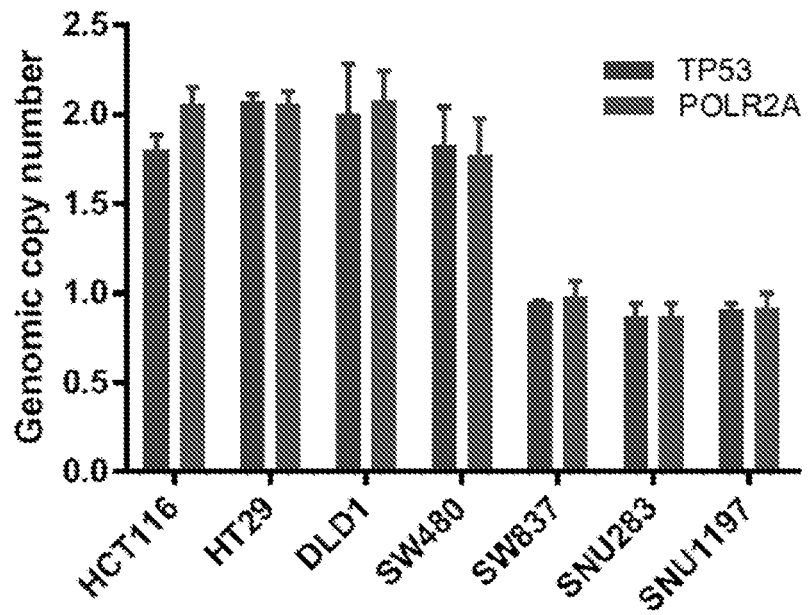
Figure 1G:
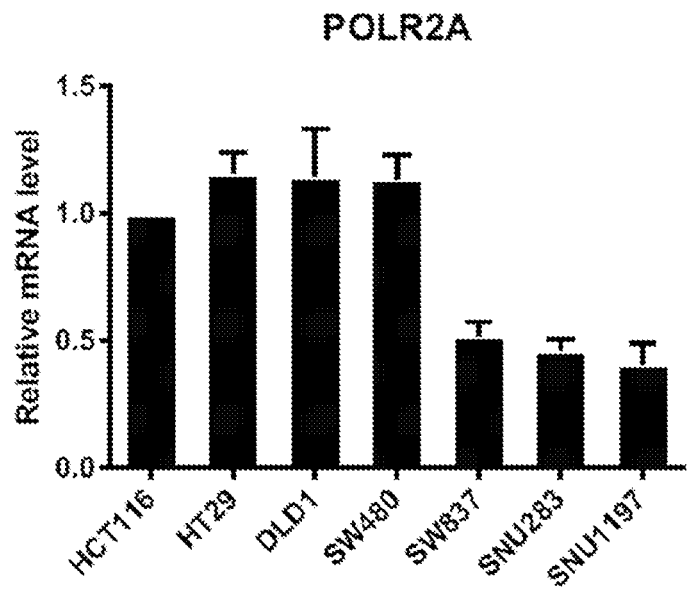
Figure 1H:
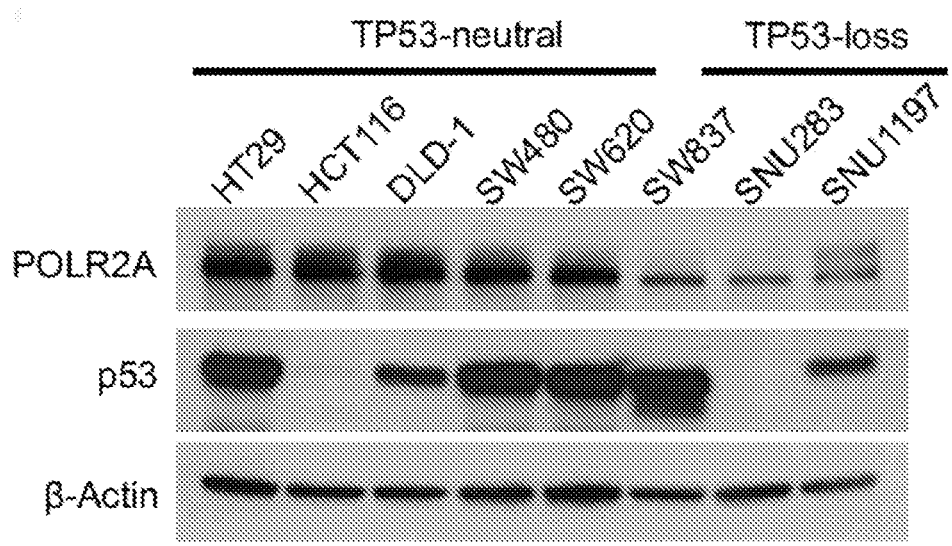
Figure 5A:
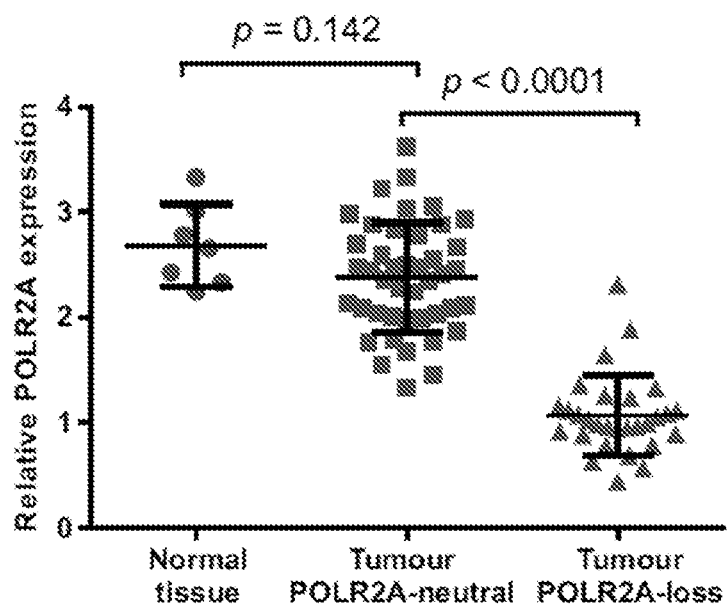
FIGS. 5A-B. Expression of POLR2A correlates with its gene copy number in human colon tumors. Double-color FISH analysis was performed using a probe for chromosome 17 centromere and locus-specific probe for POLR2A on a human colon tissue microarray. Hemizygous loss of the POLR2A gene was determined and the results are shown in Table 2.
Figure 5B:
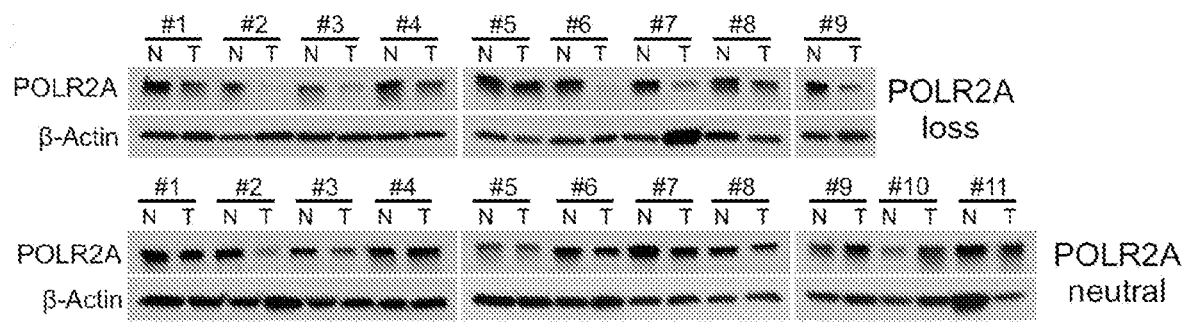

Among the twelve subunits in human RNA polymerase II complex, POLR2A encodes the largest subunit that is indispensable for the polymerase activity in mRNA synthesis (Shalem et al., 2014). Inhibiting POLR2A with a specific inhibitor, α-Amanitin, causes extensive cell death, and furthermore, homozygous deletion of POLR2A is lethal in human cells (Lindell et al., 1970; Shalem et al., 2014). It was found that 104 (53%) out of 195 colorectal cancer (CRC) cases bear partial loss of the 17p13 region, resulting in concomitant deletion of TP53 and POLR2A (FIG. 1C). However, no homozygous deletion of POLR2A was observed, consistent with the notion that POLR2A is essential for cell survival. Analysis of TCGA and CCLE databases revealed that expression of POLR2A is tightly correlated with its gene copy number (FIG. 1D). This positive correlation was also validated in twenty pairs of matched normal and CRC tissue samples and human CRC tissue microarray (FIGS. 1E, 5A, and 5B and Table 2). The copy numbers of POLR2A were determined in a set of colorectal cancer cells (FIG. 1F) and found that all the three POLR2A$^{loss}$ (hemizygous loss of POLR2A) cell lines expressed POLR2A proteins at significantly lower levels than POLR2A$^{neutral}$ cell lines (FIGS. 1G and 1H). Unlike POLR2A, p53 levels are determined by a complexity of post-transcriptional and post-translational events (Toledo and Wahl, 2006). Despite a correlation between TP53 copy number and mRNA expression, p53 protein levels are not associated with the gene copy numbers in colorectal tumors and cell lines (FIGS. 6A-6C and 1H).

TABLE 2

Hemizygous loss of POLR2A in a human colon cancer microarray (#BC051110a, Biomax) was determined by FISH assay

| ID | Sex | Age | Organ | Pathology | Grade | Stage | TNM | Type | Hemi-loss |
|---|---|---|---|---|---|---|---|---|---|
| A1 | F | 42 | Colon | Adenocarcinoma | 1 | IIB | T4N0M0 | Malignant | No |
| A3 | M | 70 | Colon | Adenocarcinoma | 1 | IIA | T3N0M0 | Malignant | No |
| A4 | F | 50 | Colon | Adenocarcinoma | 1 | IIIC | T4N2M0 | Malignant | Yes |
| A5 | F | 53 | Colon | Adenocarcinoma | 2 | IIB | T4N0M0 | Malignant | Yes |
| A6 | M | 34 | Colon | Adenocarcinoma | 1 | IIB | T4N0M0 | Malignant | Yes |
| A7 | M | 72 | Colon | Adenocarcinoma | 1 | I | T2N0M0 | Malignant | Yes |
| B1 | M | 71 | Colon | Adenocarcinoma | 1 | IIA | T3N0M0 | Malignant | No |
| B11 | F | 65 | Colon | Mucinous adencarcinoma | 1 | IIA | T3N0M0 | Malignant | No |

TABLE 2-continued

Hemizygous loss of POLR2A in a human colon cancer microarray (#BC051110a, Biomax) was determined by FISH assay

| ID | Sex | Age | Organ | Pathlogy | Grade | Stage | TNM | Type | Hemi-loss |
|---|---|---|---|---|---|---|---|---|---|
| B12 | M | 61 | Colon | Adenocarcinoma (tumoral necrosis) | 1 | IIA | T3N0M0 | Malignant | No |
| B2 | M | 60 | Colon | Adenocarcinoma | 1 | IIA | T3N0M0 | Malignant | No |
| B3 | F | 30 | Colon | Adenocarcinoma | 1 | IIIC | T3N2M0 | Malignant | Yes |
| B5 | F | 49 | Colon | Adenocarcinoma | 1 | IIIB | T4N1M0 | Malignant | Yes |
| B7 | M | 44 | Colon | Mucinous adencarcinoma | 1 | IIB | T4N0M0 | Malignant | No |
| B9 | M | 86 | Colon | Adenocarcinoma | 1 | IIIB | T4N1M0 | Malignant | No |
| C1 | F | 59 | Colon | Mucinous adenocarcinoma | 2 | IIIB | T3N1M0 | Malignant | Yes |
| C10 | M | 64 | Colon | Mucinous adenocarcinoma | 1 | IIB | T4N0M0 | Malignant | No |
| C11 | F | 52 | Colon | Adenocarcinoma | 2 | IIA | T3N0M0 | Malignant | No |
| C2 | M | 32 | Colon | Mucinous adenocarcinoma | 3 | IIA | T3N0M0 | Malignant | No |
| C3 | M | 58 | Colon | Mucinous adenocarcinoma | 1 | IV | T4N1M1 | Malignant | No |
| C5 | F | 63 | Colon | Adenocarcinoma | 1 | IIB | T4N0M0 | Malignant | Yes |
| C6 | F | 40 | Colon | Adenocarcinoma | 1 | IIIB | T3N1M0 | Malignant | No |
| C7 | M | 71 | Colon | Adenocarcinoma (sparse) | — | IIIC | T4N2M0 | Malignant | No |
| D1 | F | 70 | Colon | Adenocarcinoma | 1 | IIB | T4N0M0 | Malignant | Yes |
| D10 | M | 73 | Colon | Adenocarcinoma (sparse) | — | IIIB | T4N1M0 | Malignant | Yes |
| D11 | M | 75 | Colon | Adenocarcinoma | 2 | IIA | T3N0M0 | Malignant | No |
| D12 | M | 37 | Colon | Adenocarcinoma | 2 | IIIB | T4N1M0 | Malignant | No |
| D3 | M | 75 | Colon | Adenocarcinoma | 2 | IIB | T4N0M0 | Malignant | No |
| D4 | F | 51 | Colon | Adenocarcinoma (sparse) | — | IIB | T4N0M0 | Malignant | No |
| D5 | M | 60 | Colon | Adenocarcinoma | 2 | IIB | T4N0M0 | Malignant | No |
| D6 | F | 41 | Colon | Adenocarcinoma | 2 | IIB | T4N0M0 | Malignant | Yes |
| D7 | F | 60 | Colon | Adenocarcinoma | 2 | IIB | T4N0M0 | Malignant | No |
| D8 | F | 48 | Colon | Adenocarcinoma | 2 | IIA | T3N0M0 | Malignant | Yes |
| D9 | M | 66 | Colon | Mucinous adenocarcinoma | 2 | IIA | T3N0M0 | Malignant | Yes |
| E1 | F | 44 | Colon | Adenocarcinoma | 1 | IIA | T3N0M0 | Malignant | No |
| E10 | M | 74 | Colon | Adenocarcinoma | 2 | IIA | T3N0M0 | Malignant | No |
| E11 | M | 69 | Colon | Adenocarcinoma | 2 | IIIC | T4N2M0 | Malignant | No |
| E12 | M | 66 | Colon | Adenocarcinoma | 2 | IIA | T3N0M0 | Malignant | No |
| E2 | M | 35 | Colon | Adenocarcinoma | 1 | IIIB | T4N1M0 | Malignant | No |
| E4 | M | 70 | Colon | Adenocarcinoma | 1 | IIA | T3N0M0 | Malignant | Yes |
| E7 | M | 28 | Colon | Adenocarcinoma | 3 | IIB | T4N0M0 | Malignant | Yes |
| E9 | M | 58 | Colon | Adenocarcinoma (smooth muscle tissue) | — | IIB | T4N0M0 | Malignant | Yes |
| F11 | M | 43 | Colon | Adenocarcinoma | 2 | IIIB | T3N1M0 | Malignant | No |
| F12 | M | 50 | Colon | Adenocarcinoma | 2 | IV | T2N1M1 | Malignant | No |
| F2 | M | 76 | Colon | Mucinous adenocarcinoma | 2 | IIA | T3N0M0 | Malignant | Yes |
| F4 | F | 50 | Colon | Adenocarcinoma (sparse) | — | IIB | T4N0M0 | Malignant | Yes |
| F5 | F | 60 | Colon | Adenocarcinoma (colonic issue) | — | IIIB | T3N1M0 | Malignant | No |
| F6 | F | 49 | Colon | Mucinous adenocarcinoma | 3 | IV | T4N1M1 | Malignant | Yes |
| F8 | F | 80 | Colon | Adenocarcinoma | 2 | IIA | T3N0M0 | Malignant | Yes |
| F9 | F | 70 | Colon | Adenocarcinoma | 2 | IIIC | T3N2M0 | Malignant | No |
| G10 | M | 44 | Colon | Adenocarcinoma | 3 | IIB | T4N0M0 | Malignant | No |
| G11 | M | 31 | Colon | Adenocarcinoma | 2 | IIB | T4N0M0 | Malignant | Yes |
| G12 | M | 82 | Colon | Adenocarcinoma | 2 | IIA | T3N0M0 | Malignant | Yes |
| G2 | M | 66 | Colon | Adenocarcinoma | 1 | IIA | T3N0M0 | Malignant | Yes |
| G3 | M | 79 | Colon | Adenocarcinoma | 1 | IIA | T3N0M0 | Malignant | No |
| G5 | F | 56 | Colon | Adenocarcinoma (smooth muscle tissue) | — | IIA | T3N0M0 | Malignant | No |
| G6 | F | 73 | Colon | Adenocarcinoma | 2 | IIIC | T4N2M0 | Malignant | Yes |
| G7 | M | 77 | Colon | Adenocarcinoma | 2 | IIA | T3N0M0 | Malignant | No |
| G9 | M | 48 | Colon | Adenocarcinoma | 3 | IIA | T3N0M0 | Malignant | Yes |
| H10 | M | 58 | Colon | Adenocarcinoma | 3 | IIIB | T3N1M0 | Malignant | No |
| H11 | M | 33 | Colon | Adenocarcinoma | 3 | IIA | T3N0M0 | Malignant | No |
| H5 | M | 62 | Colon | Adenocarcinoma | 3 | IV | T4N0M1 | Malignant | No |
| H6 | M | 38 | Colon | Adenocarcinoma | 2 | IIIB | T4N1M0 | Malignant | No |
| H8 | M | 70 | Colon | Mucinous adenocarcinoma | 2 | IIB | T4N0M0 | Malignant | Yes |

TABLE 2-continued

Hemizygous loss of POLR2A in a human colon cancer microarray (#BC051110a, Biomax) was determined by FISH assay

| ID | Sex | Age | Organ | Pathlogy | Grade | Stage | TNM | Type | Hemi-loss |
|---|---|---|---|---|---|---|---|---|---|
| I1 | M | 68 | Colon | Adenocarcinoma | 3 | IV | T4N0M1 | Malignant | No |
| I10 | F | 53 | Colon | Mucinous adenocarcinoma | 3 | IIB | T4N0M0 | Malignant | No |
| I11 | M | 49 | Colon | Mucinous adenocarcinoma | 3 | IIIB | T4N1M0 | Malignant | No |
| I2 | M | 54 | Colon | Mucinous adenocarcinoma | 3 | IV | T3N1M1 | Malignant | No |
| I4 | M | 56 | Colon | Adenocarcinoma (tumoral necrosis) | — | IIA | T3N0M0 | Malignant | No |
| I5 | M | 45 | Colon | Mucinous adenocarcinoma | 3 | IIA | T3N0M0 | Malignant | Yes |
| I6 | M | 68 | Colon | Adenocarcinoma | 3 | III | T3N1M0 | Malignant | No |
| I7 | M | 36 | Colon | Adenocarcinoma | 3 | IIB | T4N0M0 | Malignant | Yes |
| J1 | M | 75 | Colon | Adenocarcinoma | 3 | IIB | T4N0M0 | Malignant | Yes |
| J10 | M | 45 | Colon | Normal colonic tissue | — | — | — | Normal | No |
| J3 | M | 35 | Colon | Normal colonic tissue | — | — | — | Normal | No |
| J4 | M | 25 | Colon | Normal colonic tissue | — | — | — | Normal | No |
| J5 | M | 35 | Colon | Normal colonic tissue | — | — | — | Normal | No |
| J6 | M | 30 | Colon | Normal colonic tissue | — | — | — | Normal | No |
| J8 | M | 40 | Colon | Normal colonic tissue | — | — | — | Normal | No |
| J9 | M | 28 | Colon | Normal colonic tissue | — | — | — | Normal | No |

Example 2—POLR2A$^{loss}$ Cells are Highly Sensitive to POLR2A Inhibition

Figure 2A:
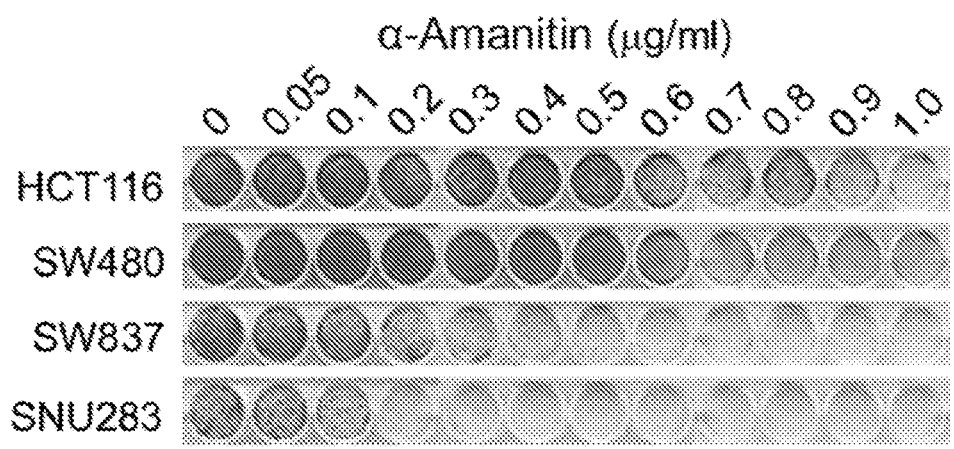
FIGS. 2A-J. POLR2A$^{loss}$ cells are highly sensitive to the POLR2A inhibition.
Figure 2B:
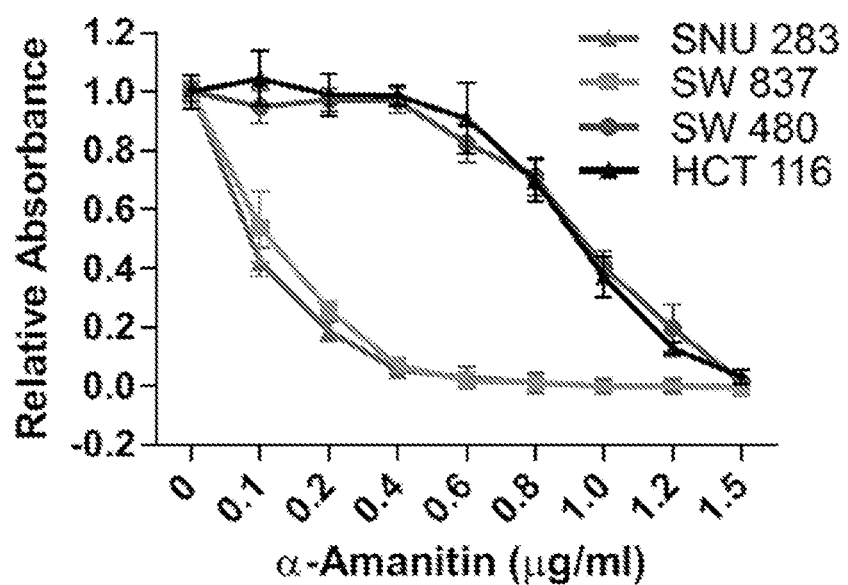
Figure 2C:
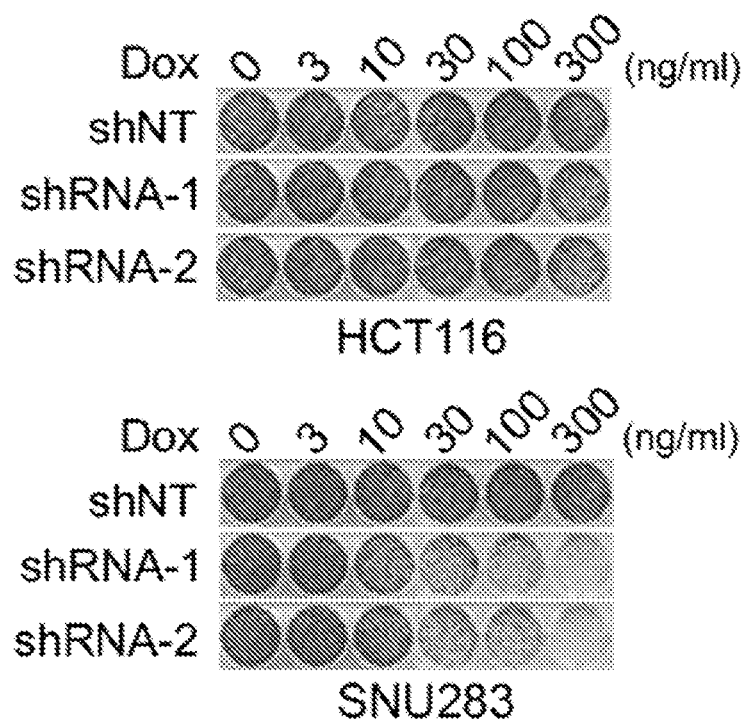
Figure 2D:
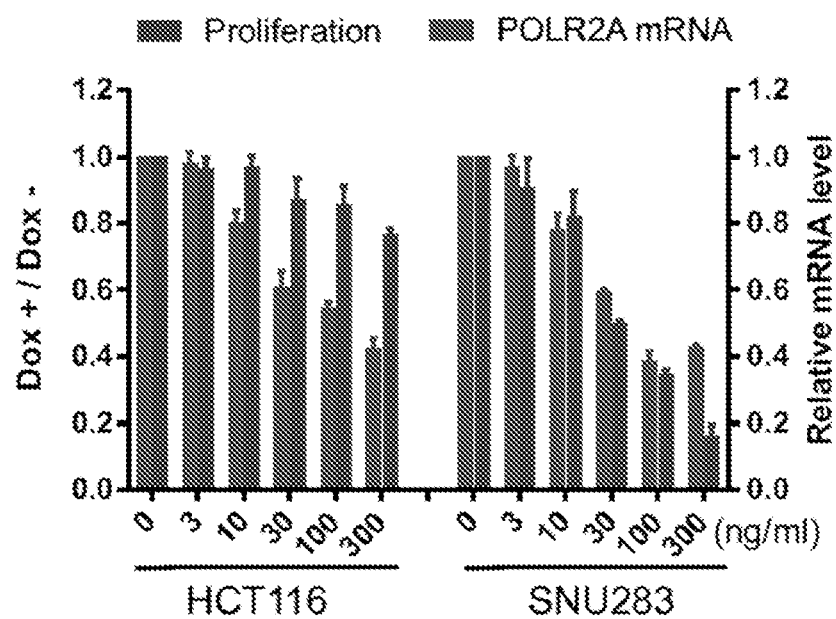
Figure 2E:
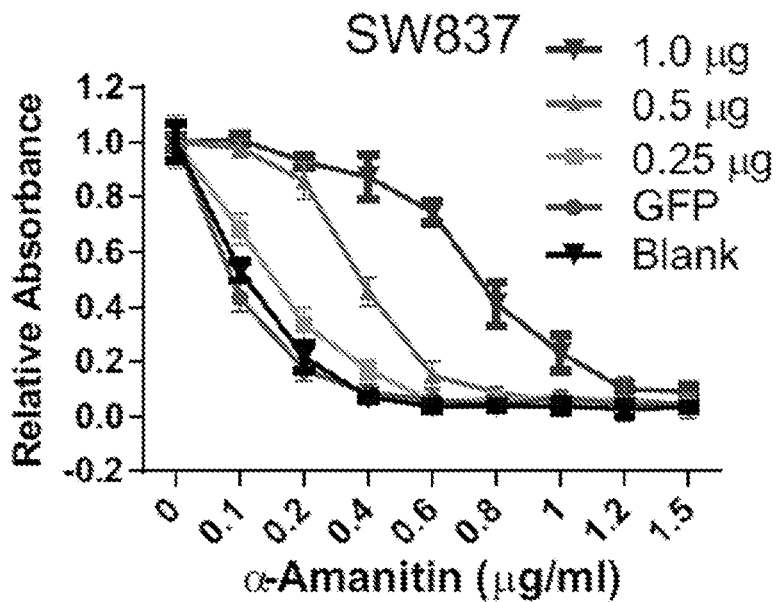
Figure 2F:
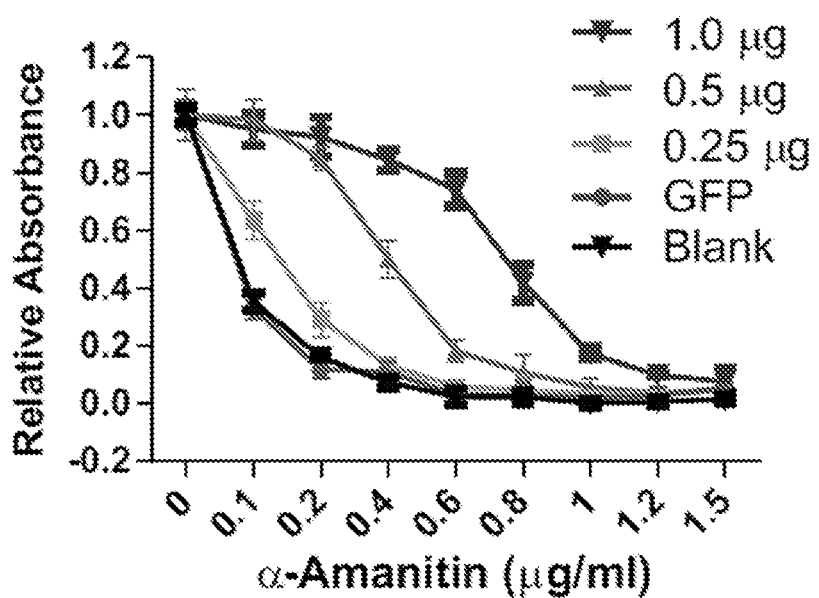
Figure 7A:
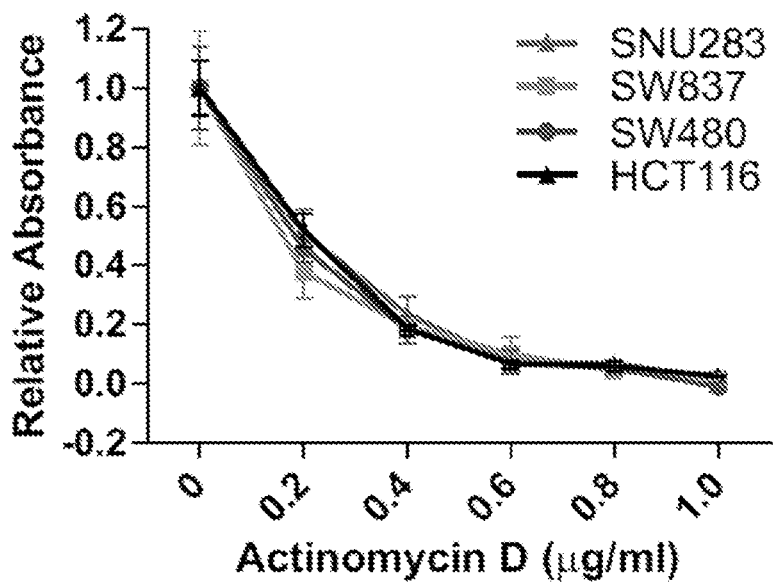
FIGS. 7A-G. POLR2A$^{loss}$ cells are highly sensitive to POLR2A inhibition.
Figure 7B:
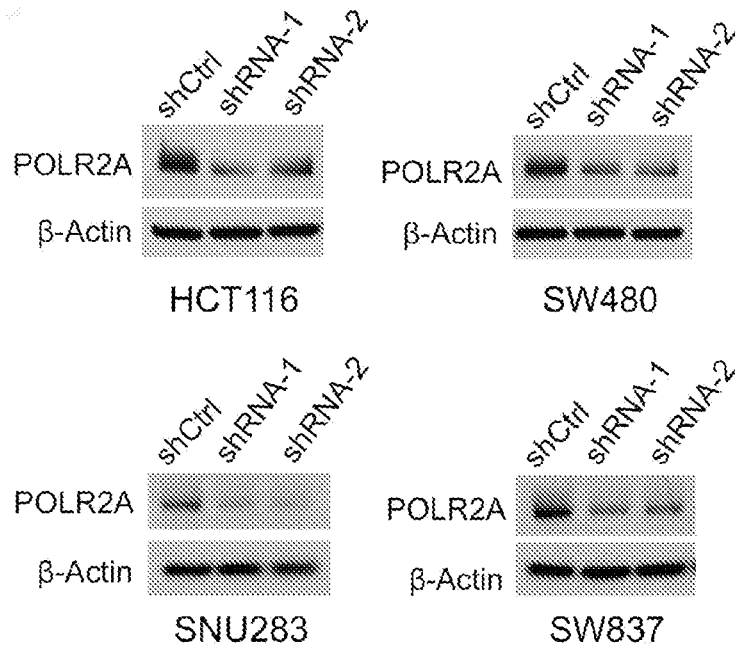
Figure 7C:
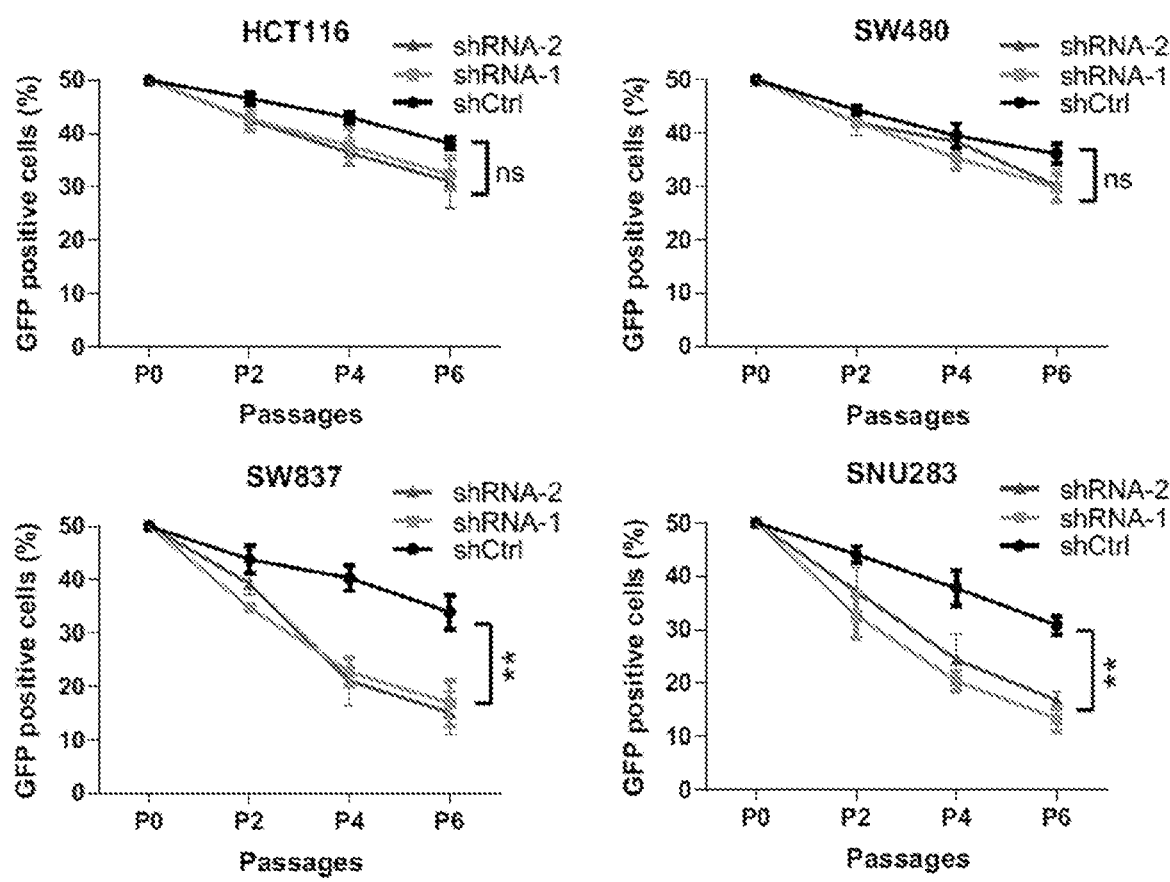
Figure 7D:
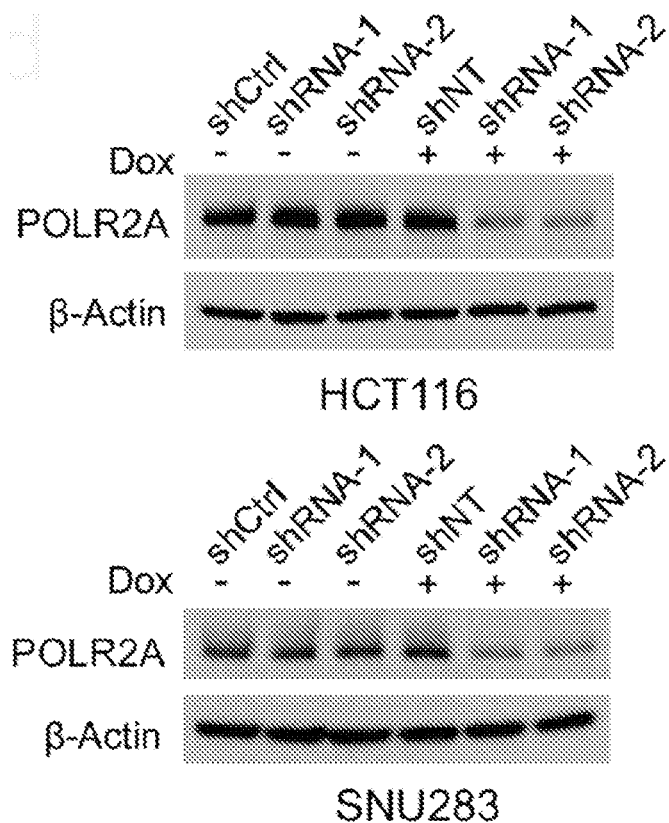
Figure 7E:
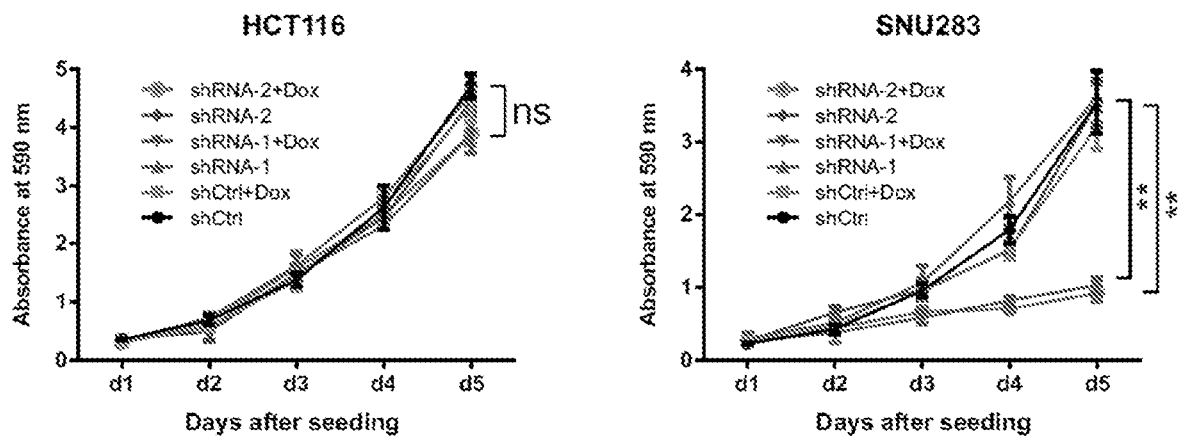
Figure 7F:
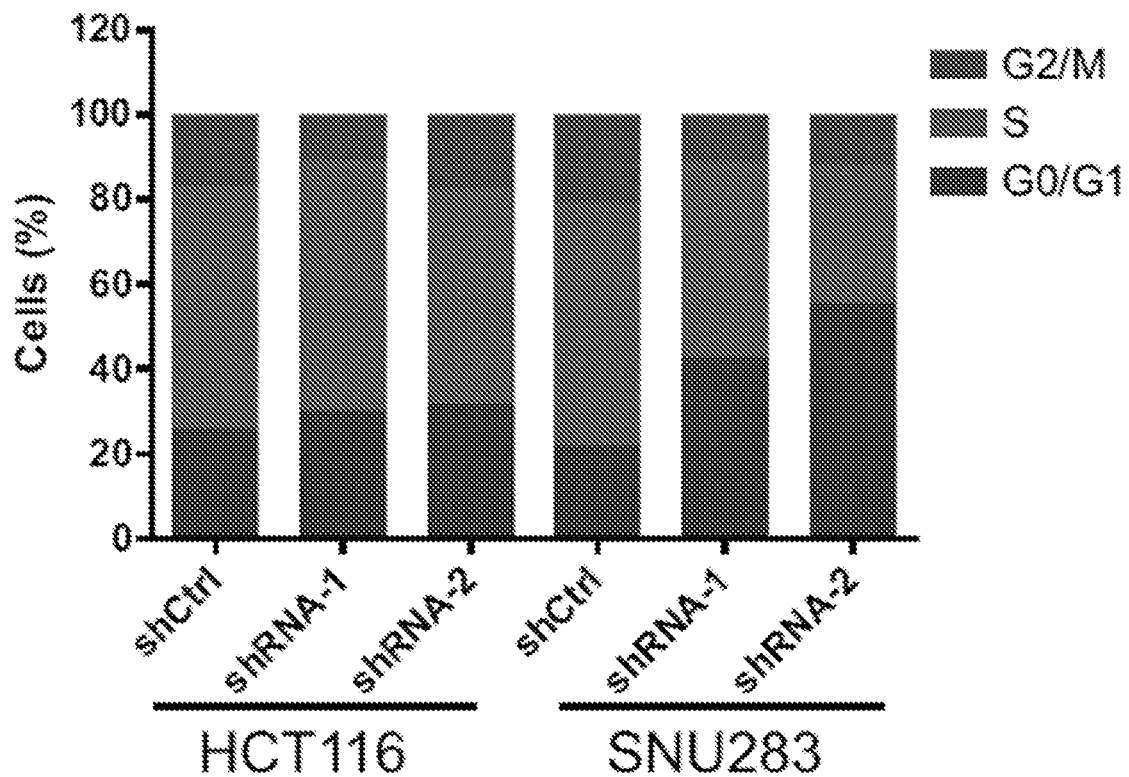
Figure 7G:
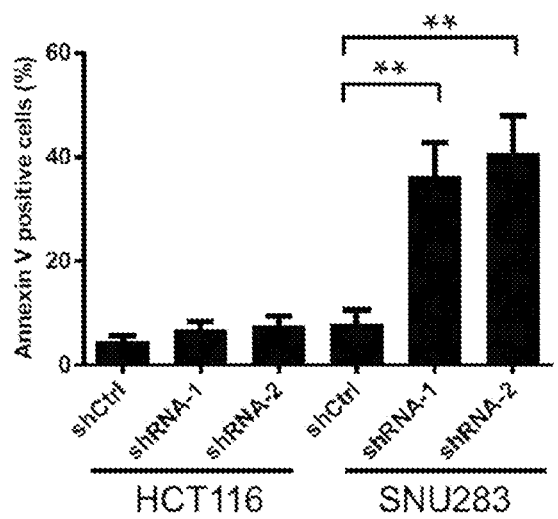
Figure 8A:
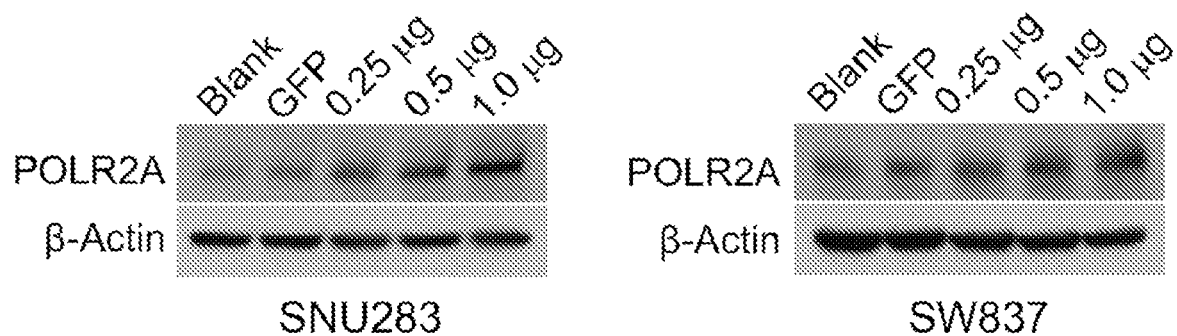
FIGS. 8A-B. Ectopic expression of POLR2A restores the resistance of POLR2A$^{loss}$ cells to α-Amanitin treatment.
Figure 8B:
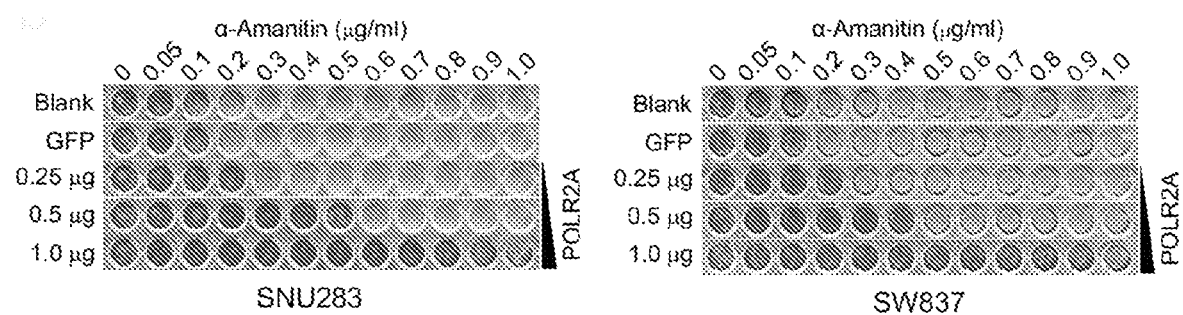

To assess the sensitivity of cells with or without TP53/POLR2A hemizygous loss to POLR2A inhibition, a panel of POLR2A$^{neutral}$ (HCT116, SW480) and POLR2A$^{loss}$ (SW837, SNU283) cells were treated with α-Amanitin. Treatment of α-Amanitin at high concentrations (≥1 μg ml$^{-1}$) drastically inhibited cell growth and caused complete cell death in all four cell lines. However, at concentrations from 0 to 1.0 μg ml$^{-1}$, α-Amanitin inhibition had significantly higher levels of cell-killing effect on the POLR2A$^{loss}$ cells than on the control POLR2A$^{neutral}$ cells (FIGS. 2A and 2B). The half-maximum inhibitory concentration (IC$_{50}$) was ~1.0 μg ml$^{-1}$ for the POLR2A$^{neutral}$ cells, which was 10-fold greater than that of the POLR2A$^{loss}$ cells. By contrast, the POLR2A$^{loss}$ cells did not show any greater sensitivity to the treatment of actinomycin D, a nonspecific transcription inhibitor (FIG. 7A). Next, the vulnerability of POLR2A$^{loss}$ cells was evaluated using direct competition assay. Cell proliferation rates were compared between control cells and GFP-positive cells expressing control or POLR2A-specific shRNA. Two independent shRNAs knocked down POLR2A expression by 50%-70% in all the tested cell lines (FIG. 7B). After culturing for six passages, the POLR2A$^{neutral}$ cells (HCT116, SW480) stably expressing POLR2A shRNAs only had modestly reduced proliferation, in comparison with that of the corresponding cells expressing control shRNAs (FIG. 7C). However, silencing POLR2A in the POLR2A$^{loss}$ cells (SNU283, SW837) led to markedly reduced proliferation, suggesting that hemizygous loss of POLR2A renders cancer cells more prone to further POLR2A inhibition. HCT116 and SNU283 cell lines stably expressing doxycycline (Dox)-inducible POLR2A shRNAs were generated (FIG. 7D). Despite significant knockdown of POLR2A, HCT116 cells continued to proliferate, whereas SNU283 cells exhibited severe G1 cell cycle arrest and apoptosis (FIGS. 2C, 2D, and 7E-7G). Approximately 50% of decrease in POLR2A expression (with the addition of 30-100 ng ml$^{-1}$ of Dox) remarkably reduced the proliferation of SNU283 cells, but only had a modest effect on HCT116 cells (FIG. 2D). Next, rescue experiments were performed in the POLR2A$^{loss}$ SNU283 and SW837 cell lines. Gradual re-expression of exogenous POLR2A in both cell lines restored their resistance to α-Amanitin up to a level comparable to that of the POLR2A$^{neutral}$ HCT116 and SW480 cells (FIGS. 2E, 2F, and 8A-8B).

Figure 2G:
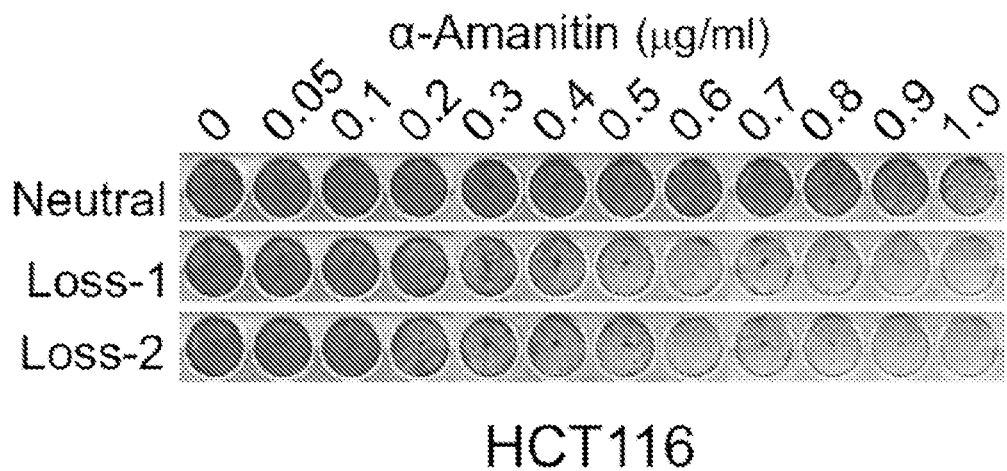
Figure 2H:
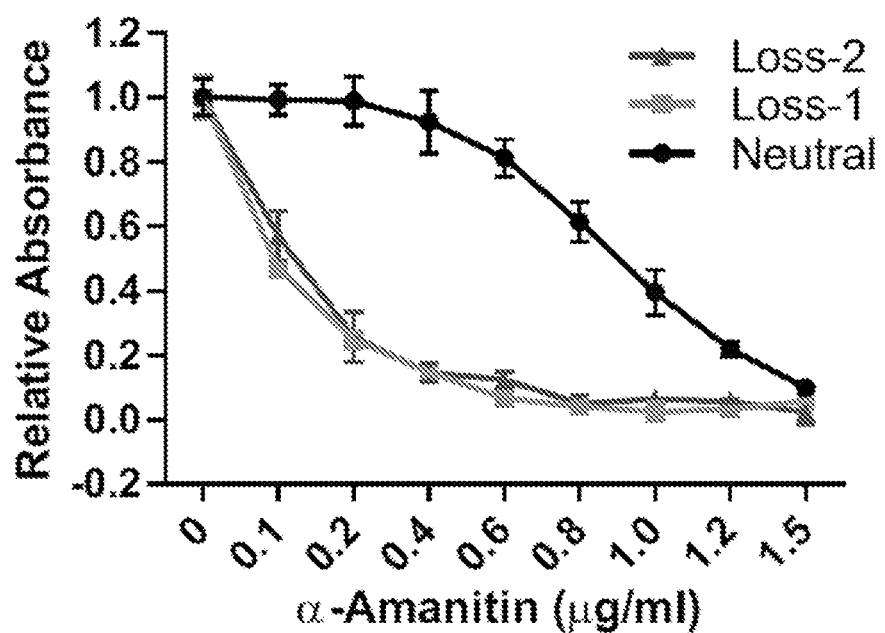
Figure 2I:
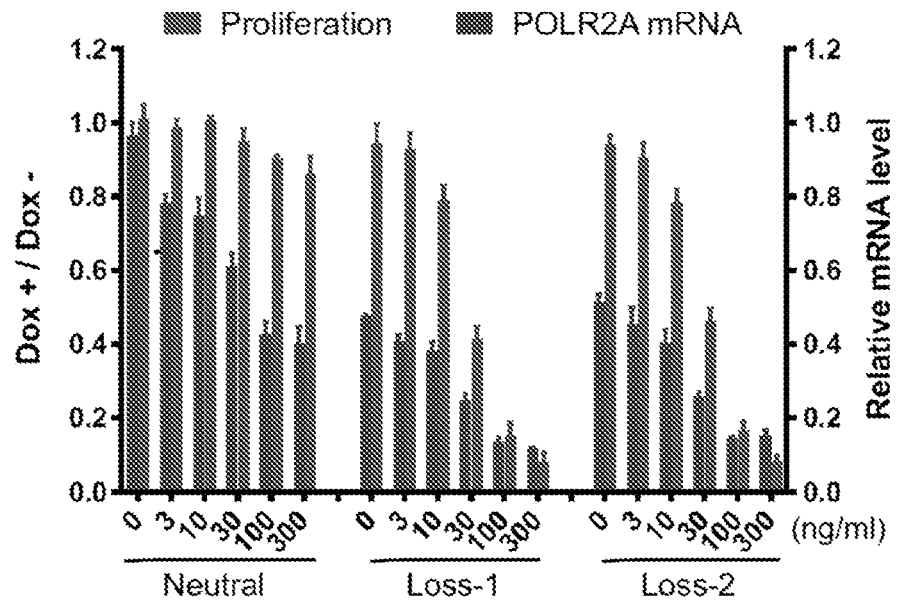
Figure 2J:
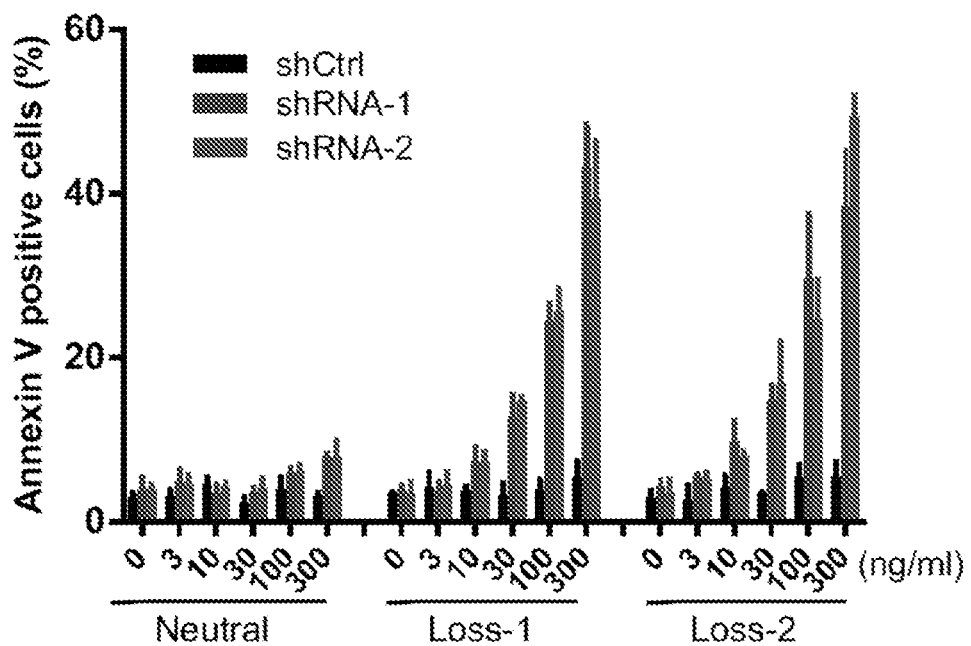
Figure 9D:
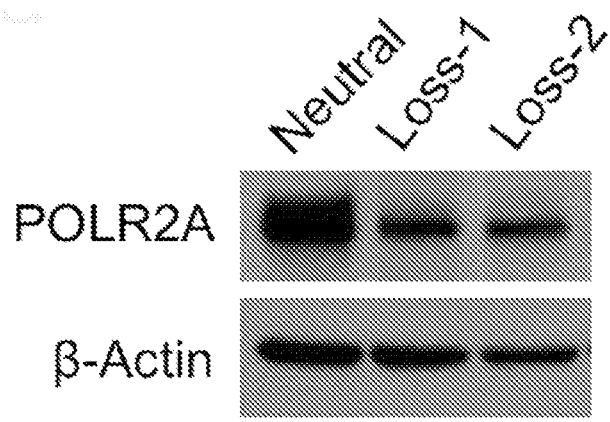
Figure 9E:
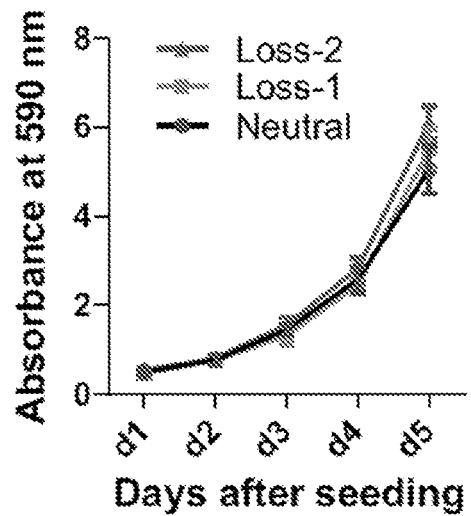
Figure 9F:
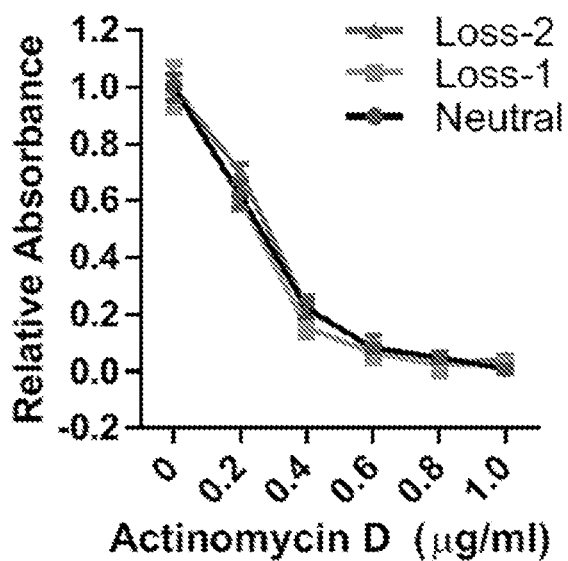
Figure 9G:
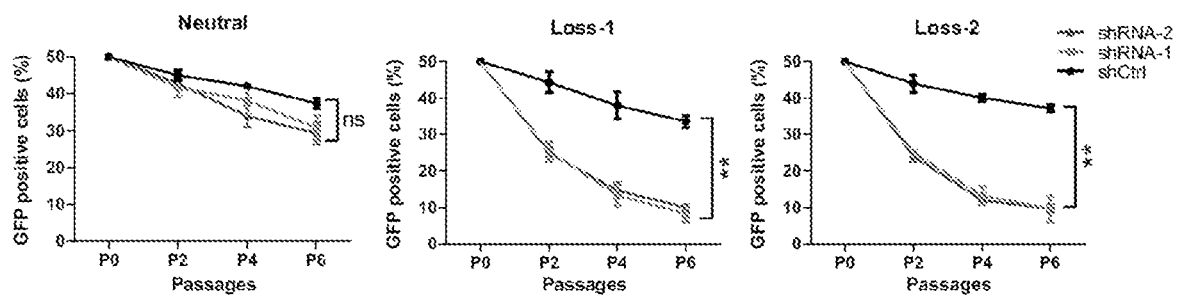
Figure 9H:
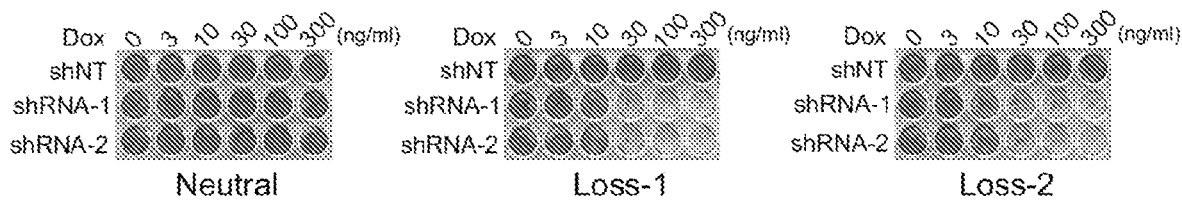

To exclude the effects of various genetic backgrounds across cell lines, the CRISPR (clustered regularly interspaced short palindromic repeat)/Cas9 system was employed to generate an isogenic HCT116 cell line with hemizygous loss of POLR2A (Wang et al., 2014; Wang et al., 2013). Two single-guide RNAs (sgRNAs) were designed to target the second exon of the POLR2A gene (FIG. 9A). Both of them efficiently targeted and disrupted the POLR2A gene, as shown in the Surveyor analysis (FIG. 9B). Single colonies of HCT116 cells bearing mono-allelic deletion of POLR2A were selected and verified by DNA sequencing (FIG. 9C). Small deletion in the targeted region led to open reading frame shift, producing only a short stretch of the N-terminal peptide without all functional domains of POLR2A. As a result, POLR2A expression was significantly reduced in the POLR2A$^{loss}$ cells (FIG. 9D). The POLR2A$^{loss}$ and POLR2A$^{neutral}$ HCT116 cells exhibited similar proliferation rates (FIG. 9E), indicating that one allele of POLR2A is sufficient to maintain cell proliferation and survival. However, hemizygous deletion of POLR2A dramatically sensitized HCT116 cells to α-Amanitin treatment with an IC$_{50}$ of ~0.1 μg ml$^{-1}$, which is 8-fold lower than that of parental HCT116 cells (FIGS. 2G and 2H). As a control, no substantial difference on their sensitivity to actinomycin D was observed (FIG. 9F). Result of direct competition assays demonstrated that knockdown of POLR2A resulted in markedly reduced proliferation in the POLR2A$^{loss}$ cells, but not in the isogenic POLR2A$^{neutral}$ cells (FIG. 9G). POLR2A$^{loss}$ and POLR2A$^{neutral}$ HCT116 cells expressing Dox-inducible POLR2A shRNA were also generated. Increased concentrations of Dox gradually reduced POLR2A expression. While a low-dose of Dox (100 ng ml$^{-1}$) was sufficient to remarkably kill the POLR2A$^{loss}$ cells, high doses of Dox only had minimal effects on the POLR2A$^{neutral}$ cells (FIGS. 2I, 2J, and 9H).

Example 3—the Sensitivity of POLR2A$^{loss}$ Cells to POLR2A Inhibition is Independent of p53

Figure 3A:
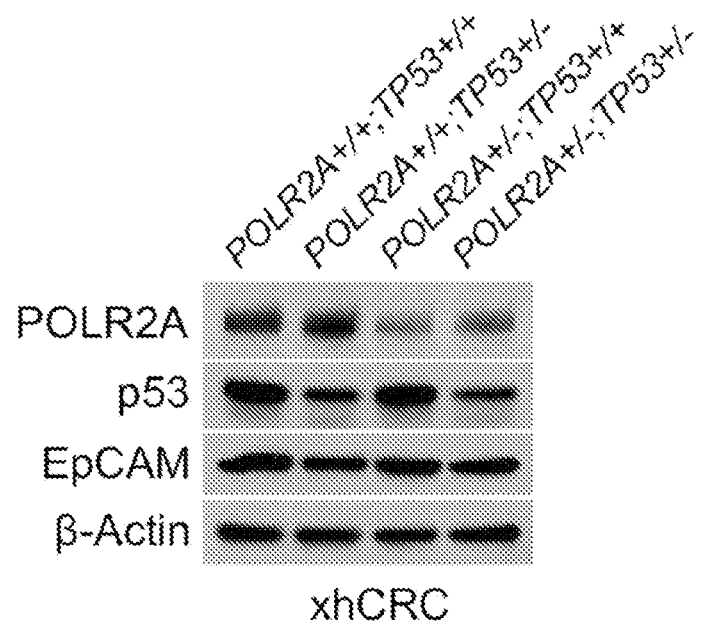
FIGS. 3A-E. The sensitivity of POLR2A$^{loss}$ cells to POLR2A inhibition is independent of p53.
Figure 3B:
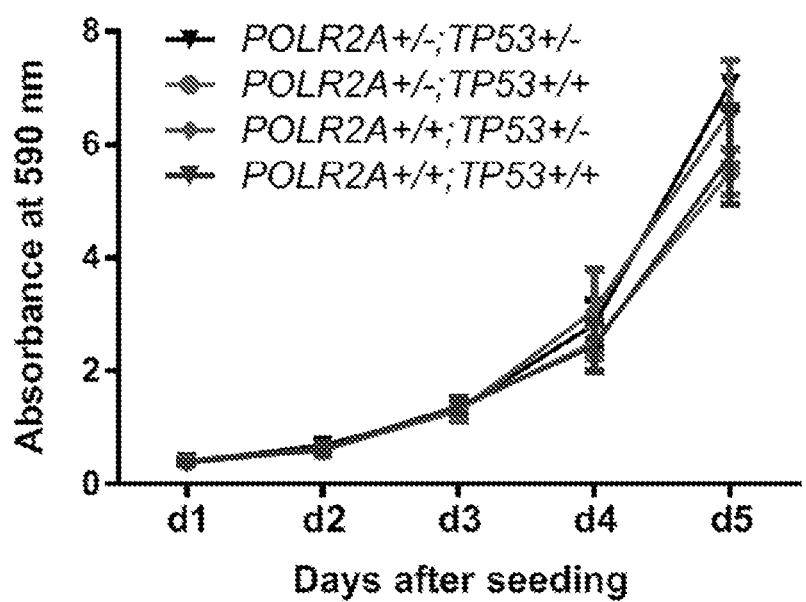
Figure 3C:
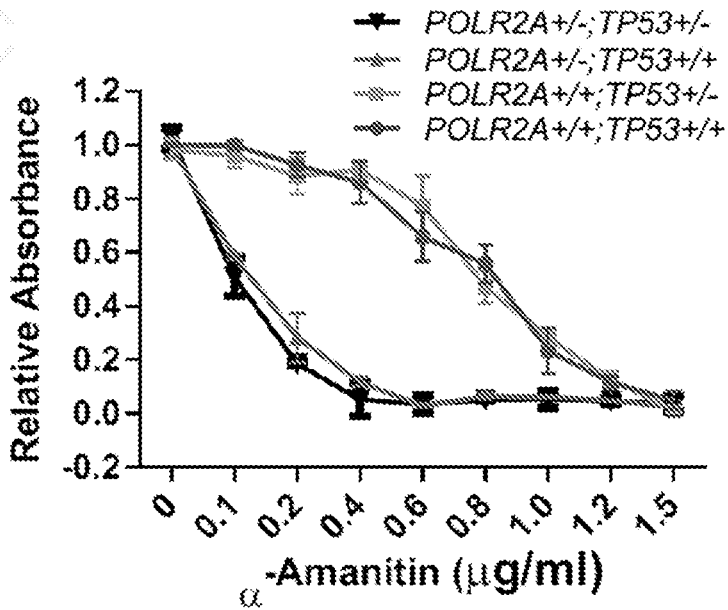
Figure 3D:
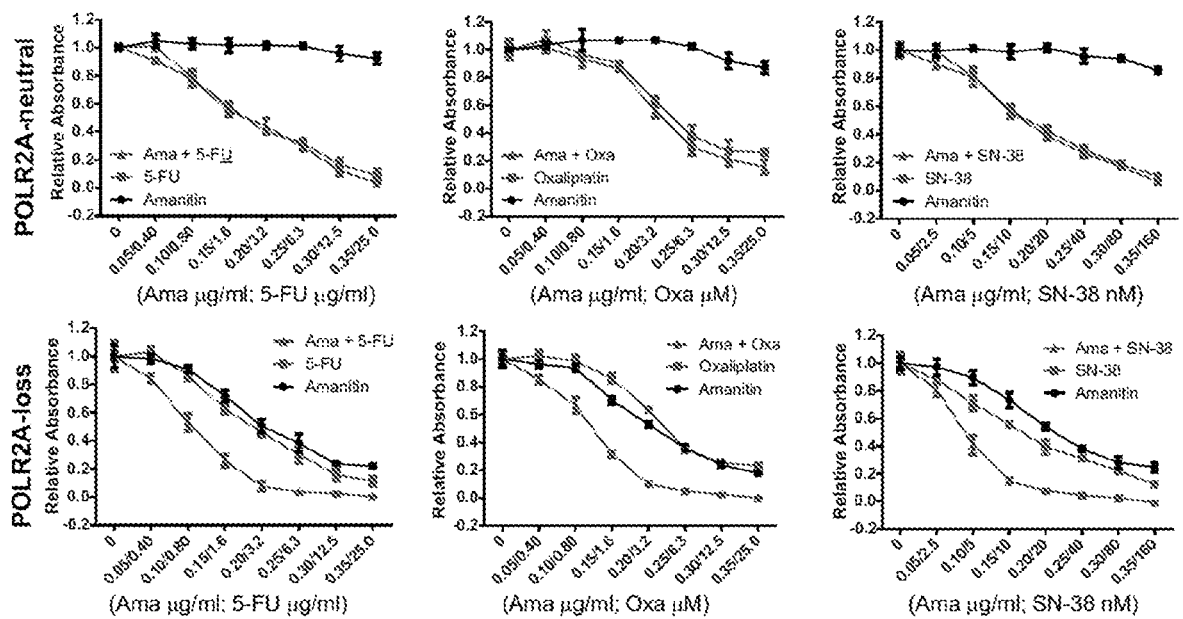

Blockage of RNA polymerase may lead to p53 accumulation and activation (Derheimer et al., 2007). To examine the effects of p53 on cell response to POLR2A inhibition, the concomitant deletion of TP53 and POLR2A was recapitulated in HCT116 and xhCRC cell lines (FIGS. 3A and 10A-10C). The xhCRC cell line (TP53+/+; POLR2A+/+) was established from a freshly isolated xenografted human colorectal tumor, which demonstrated enhanced tumorigenicity in vivo (Lu et al., 2013). Except for slightly increased cell proliferation, no significant changes in their sensitivity to α-Amanitin were observed in both xhCRC and HCT116 cells with hemizygous deletion of TP53. By contrast, hemizygous loss of POLR2A markedly sensitized these cells to α-Amanitin treatment regardless of their TP53 status (FIGS. 3B, 3C, and 10D-10F). The RNA polymerase II is in charge of mRNA synthesis, an essential function for any type of cells including therapy-resistant tumor cells. The drug sensitivity of POLR2A$^{neutral}$ and POLR2A$^{loss}$ cells to three major chemotherapy drugs for colorectal cancer (5-fluorouracil (5-FU), oxaliplatin, and SN-38) was examined. Inhibition of POLR2A by α-Amanitin significantly enhanced cell-killing effects of all three drugs in the POLR2A$^{loss}$ xhCRC cells, but had no notable effects on the POLR2A$^{neutral}$ cells (FIG. 3D), suggesting therapeutic vulnerability of POLR2A$^{loss}$ colorectal tumors in cancer therapy. Free α-Amanitin is toxic to liver because it is specifically bound by OATP1B3, a transporter exclusively expressed on the membrane of hepatocytes (Letschert et al., 2006). However, α-Amanitin, when conjugated with specific antibodies, is no longer a substrate for OATP1B3 (Letschert et al., 2006; Moldenhauer et al., 2012; Faulstich and Fiume, 1985). This strategy overcomes the toxicity of α-Amanitin for clinical applications. α-Amanitin conjugated to a monoclonal antibody (HEA125) against EpCAM (ama-HEA125), a cancer antigen overexpressed in the majority of adenocarcinomas (Moldenhauer et al., 2012; Went et al., 2004), was used. The ama-HEA125 conjugate selectively killed the POLR2A$^{loss}$ xhCRC and HCT116 cancer cells in a p53-independent manner and reduced the effective doses of α-Amanitin by at least 10,000-fold (IC$_{50}$~0.01 ng ml$^{-1}$) in vitro (FIGS. 3E and 10G).

Figure 4A:
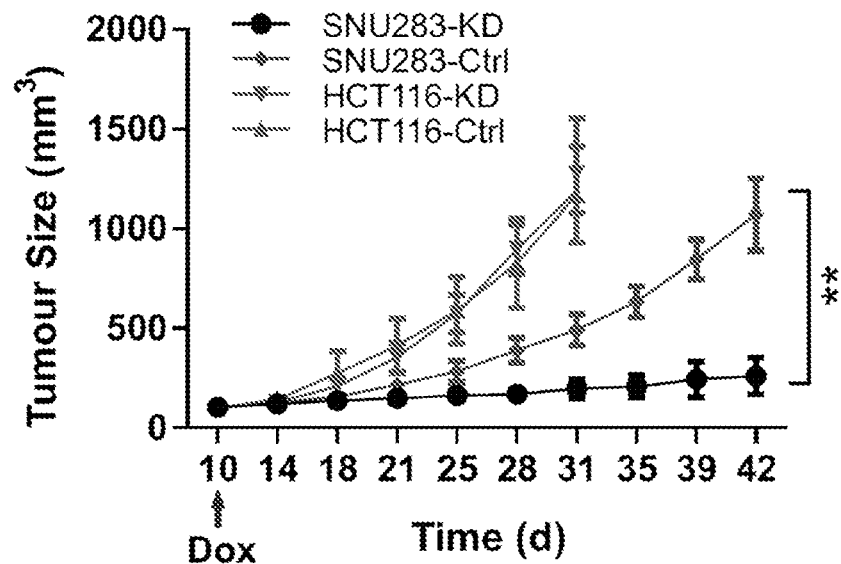
FIGS. 4A-E. Suppression of POLR2A selectively inhibits the POLR2A$^{loss}$ tumor growth.
Figure 4B:
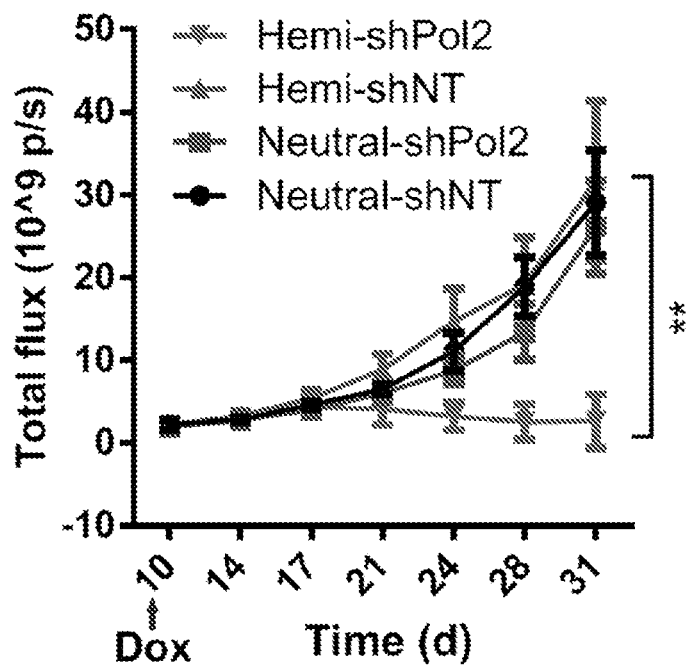
Figure 4C:
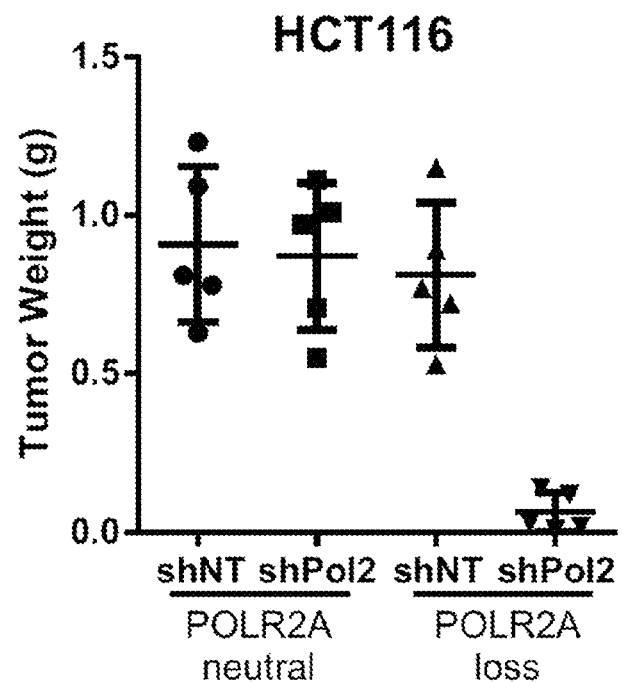
Figure 11A:
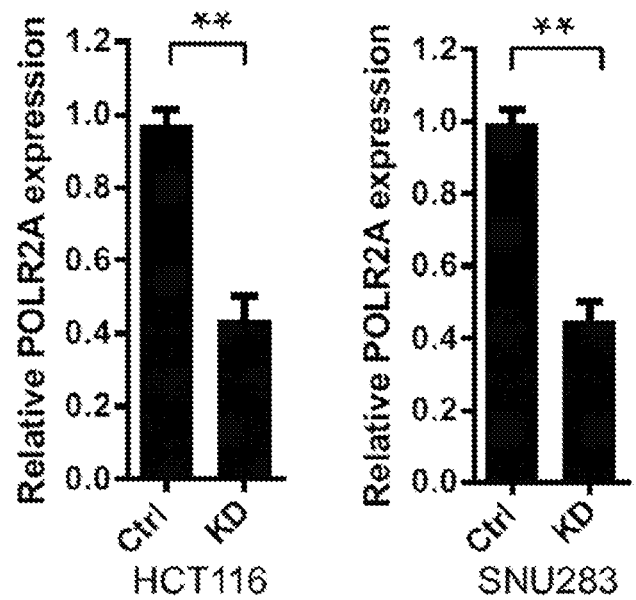
FIGS. 11A-C. Dose-dependent suppression of POLR2A inhibits tumorigenesis in POLR2A$^{loss}$, but not POLR2A$^{neutral}$ tumors.
Figure 11B:
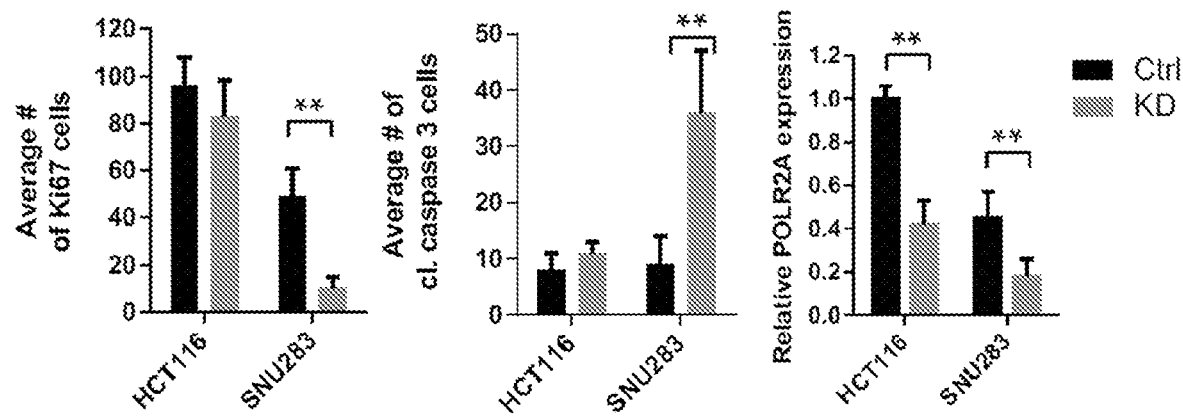
Figure 11C:
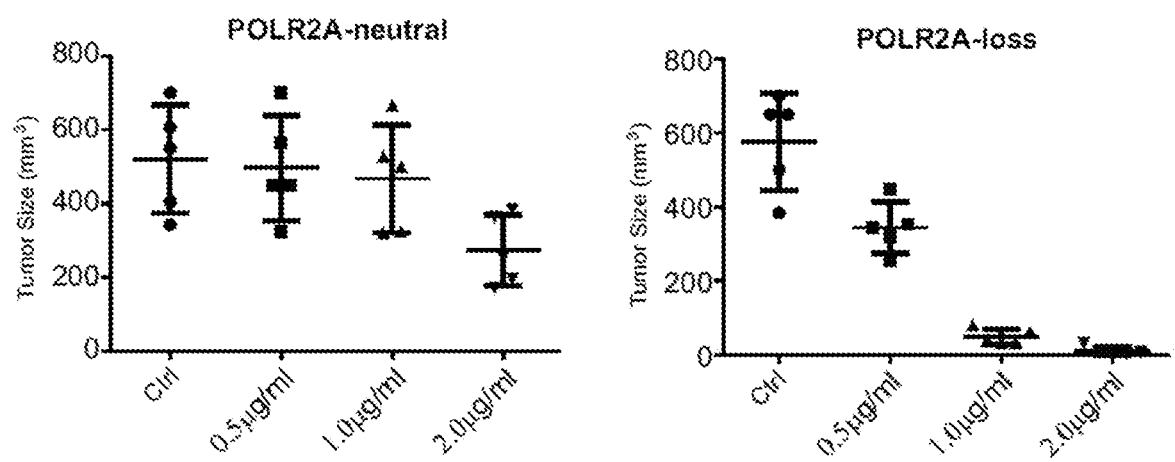
Figure 12A:
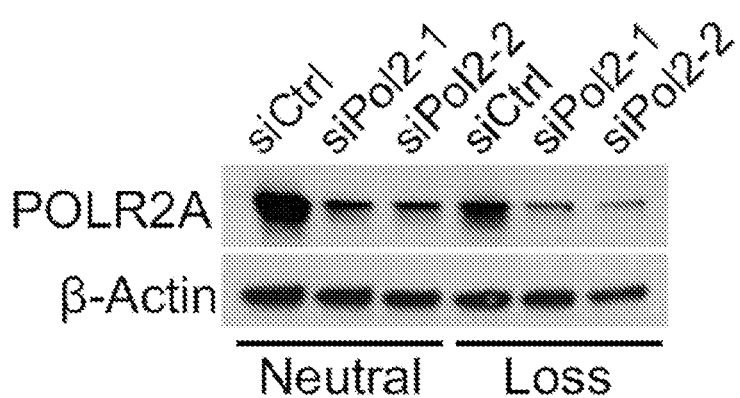
FIGS. 12A-F. Suppression of POLR2A with DOPC-encapsulated POLR2A siRNA inhibits the growth of POLR2A$^{loss}$ tumors.
Figure 12B:
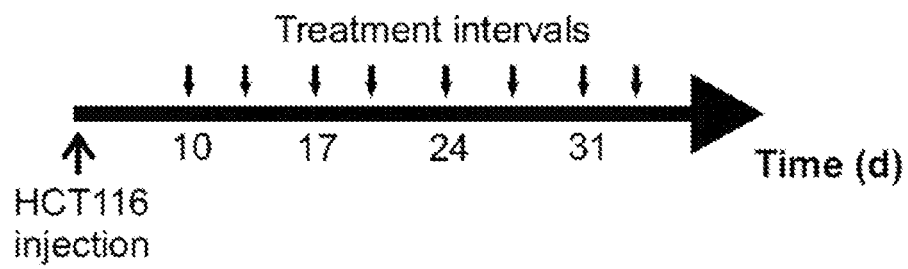
Figure 12C:
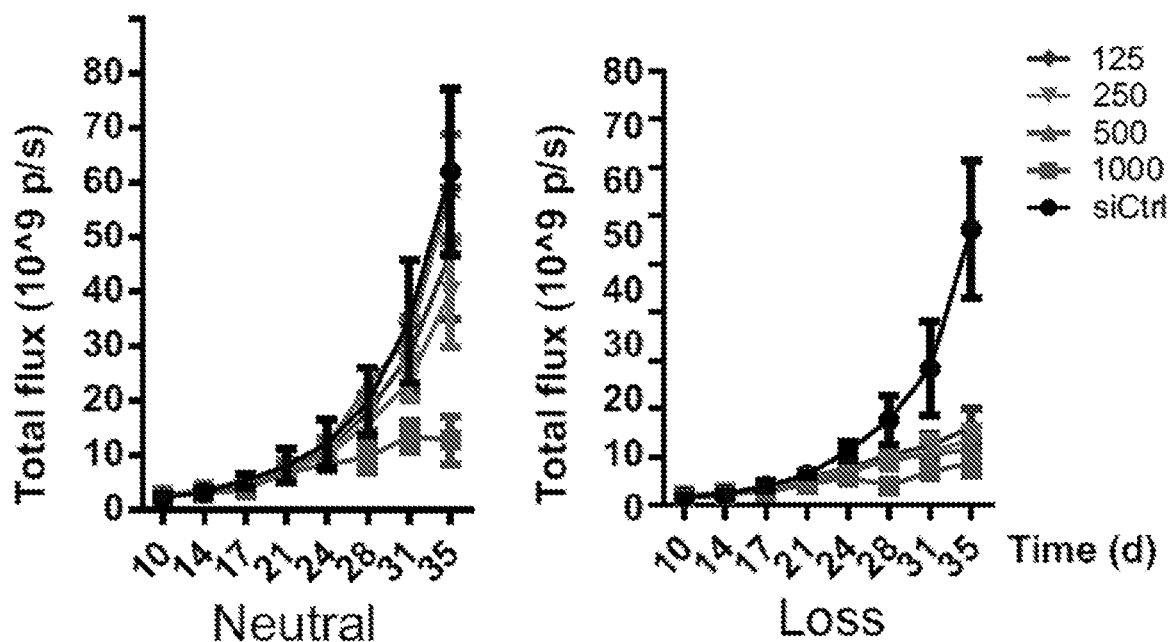
Figure 12D:
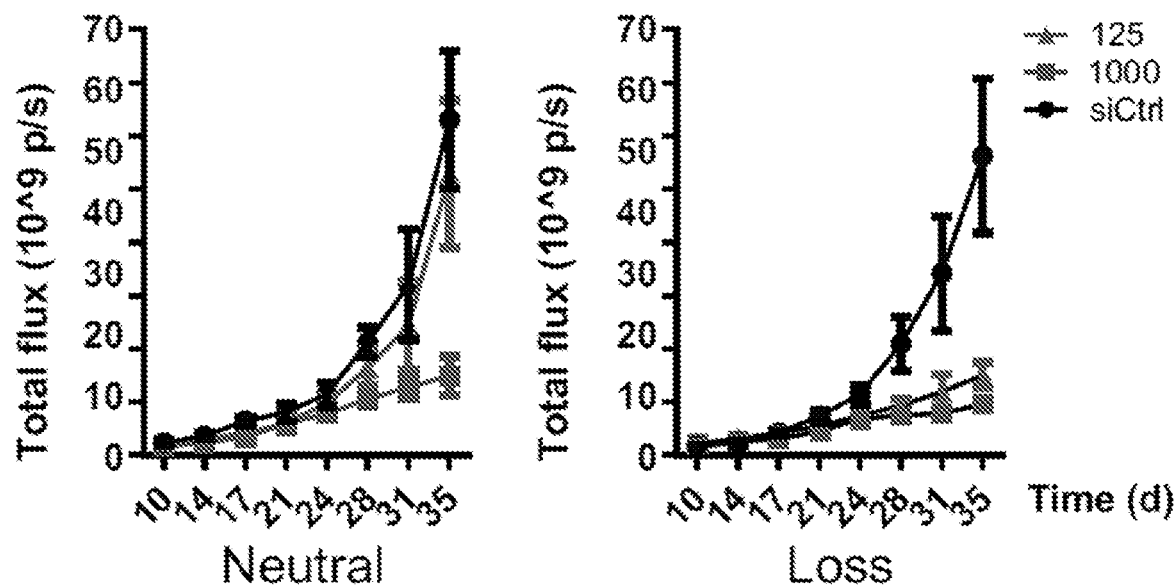
Figure 12E:
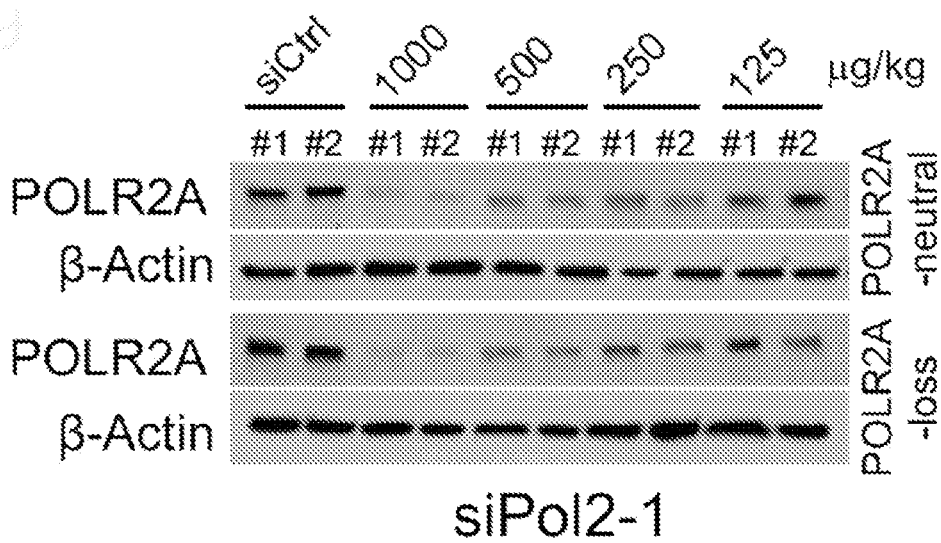
Figure 12F:
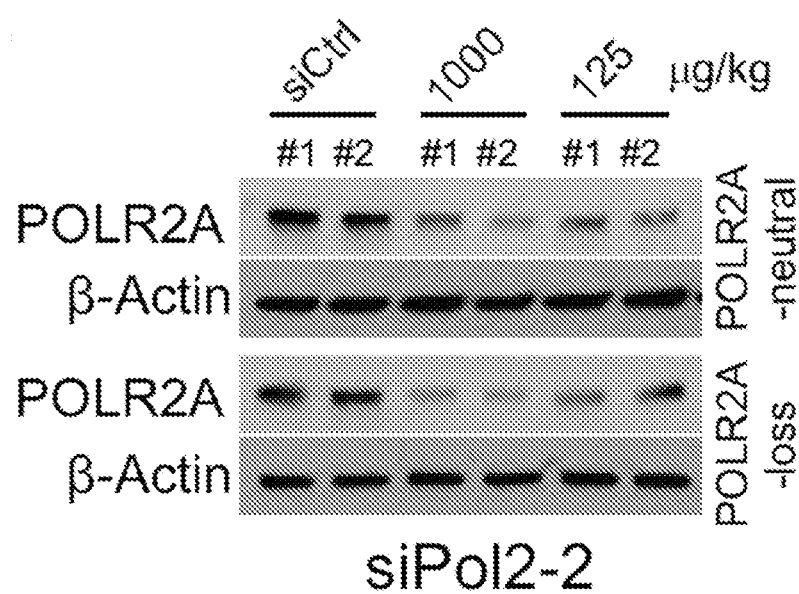

Example 4—Suppression of POLR2A Selectively Inhibits POLR2A$^{loss}$ Tumor Growth To test the anti-tumor effect of POLR2A inhibition in vivo, HCT116 and SNU283 cells expressing Dox-inducible POLR2A shRNA were injected subcutaneously into immunocompromised SCID BALB/c mice. Following initial tumor establishment, administration of Dox in drinking water suppressed POLR2A expression and consequently inhibited the growth of SNU283-derived tumors (FIG. 4A). However, no substantial differences were observed between control and POLR2A-knockdown HCT116-derived tumors. Histopathologic analyzes demonstrated that POLR2A-knockdown (Dox: 1.0 μg ml$^{-1}$) SNU283 tumors had significantly reduced cell proliferation (Ki67 staining), but more apoptotic cells (cleaved caspase-3 staining), as compared with the corresponding control tumors (FIGS. 11A-11B). By contrast, no significant changes were observed in the control or POLR2A-knockdown HCT116 tumors. However, heterozygous deletion of POLR2A sensitized POLR2A+/− HCT116-derived tumors to the suppression of Dox-inducible POLR2A shRNA (FIG. 11C). Next, an orthotopic tumor model was employed to test the effect of POLR2A inhibition. POLR2A$^{neutral}$ and POLR2A$^{loss}$ HCT116 cells were injected into the cecal wall of SCID mice. Once orthotopic tumors were established, mice were administrated Dox (1.0 μg ml$^{-1}$) in the drinking water. In vivo bioluminescent imaging of tumors demonstrated that Dox-induced POLR2A inhibition led to a significant decrease in tumor growth kinetics in the POLR2A$^{loss}$ tumors, but not in the control POLR2A$^{neutral}$ tumors (FIGS. 4B-C). After 3-week treatment of Dox, gross tumors were visible in the POLR2A$^{neutral}$ tumor group, whereas significantly reduced tumor growth or no visible tumor was observed in the POLR2A$^{loss}$ group. To further test the efficacy of POLR2A silencing in vivo, a nanoliposomal delivery platform, DOPC (1,2-dioleoyl-sn-glycero-3-phosphatidylcholine), was used for systemic delivery of POLR2A siRNAs (Pecot et al., 2014). Two specific POLR2A siRNAs had greater than 80% knockdown of POLR2A protein in isogenic HCT116 cell lines (FIG. 12A). Ten days following orthotopic injection of 1.0×10$^6$ isogenic HCT116 cells, mice were randomly assigned to the treatment groups (n=10 mice/group). Twice-weekly treatment of siRNAs incorporated into DOPC nanoliposomes was commenced (FIG. 12B). Following four weeks of systemic therapy, compared with control siRNA-DOPC treatment, mice in the 125 μg kg$^{-1}$ of POLR2A siRNA-DOPC treatment groups had pronounced growth reduction of POLR2A$^{loss}$ tumors, while POLR2A$^{neutral}$ tumors only had significant growth inhibition at the dose of 1,000 μg kg$^{-1}$ of POLR2A siRNA-DOPC (FIGS. 12C-F).

Figure 3E:
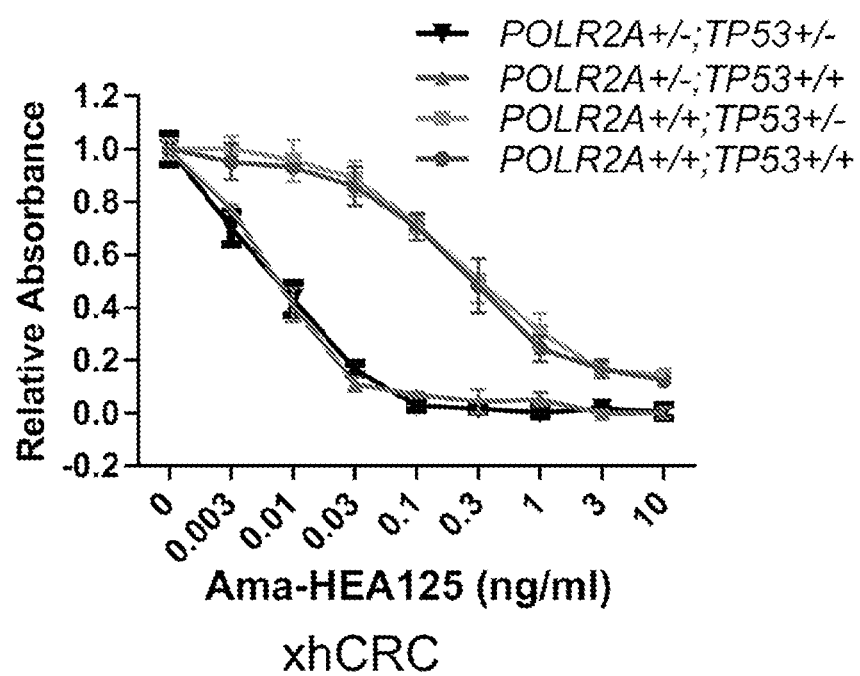
Figure 4D:
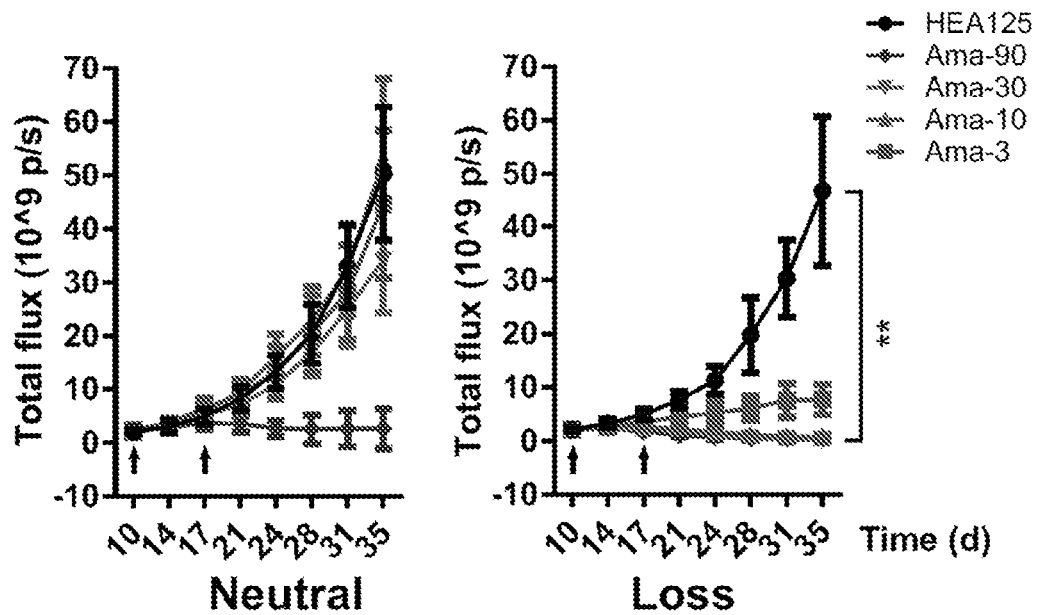
Figure 4E:
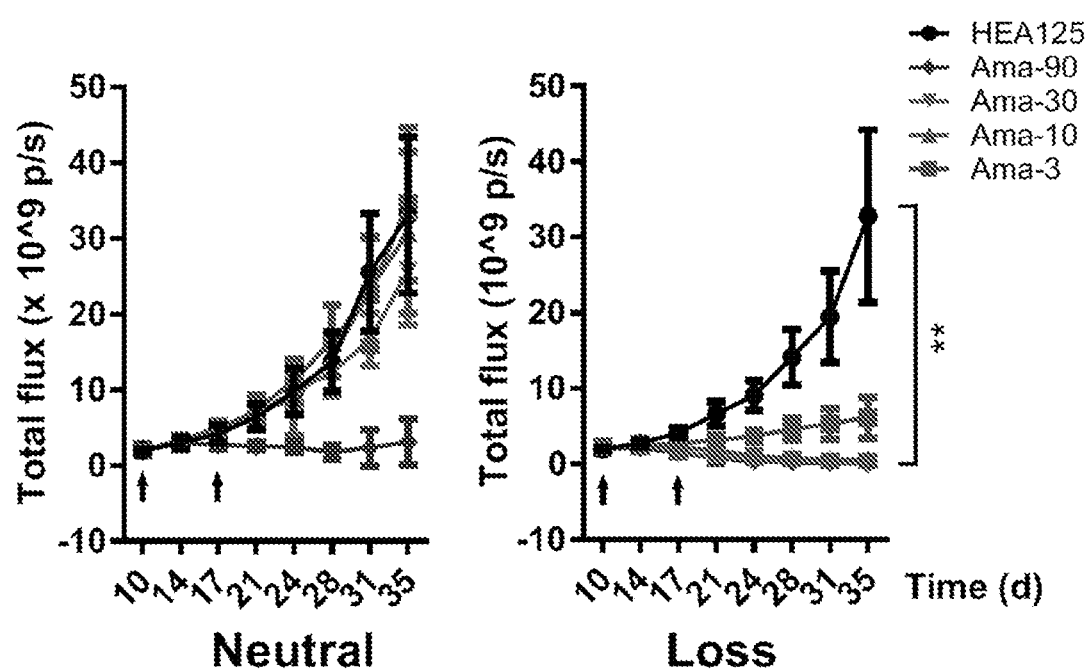
Figure 10A:
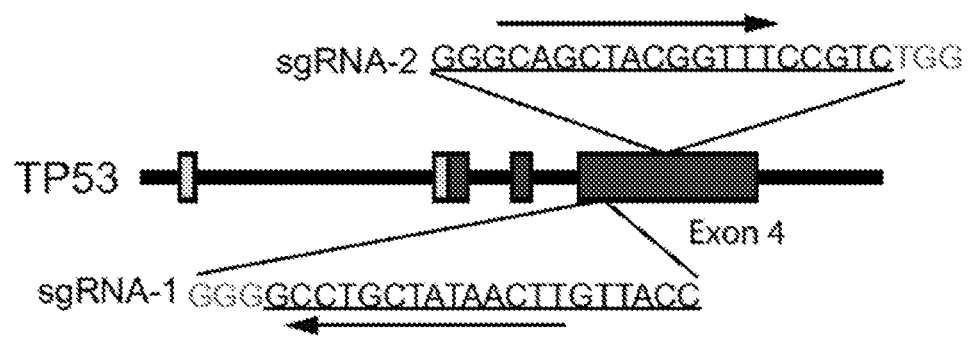
FIGS. 10A-G. Sensitivity of POLR2A$^{loss}$ cells to POLR2A inhibition is independent of p53.
Figure 10B:
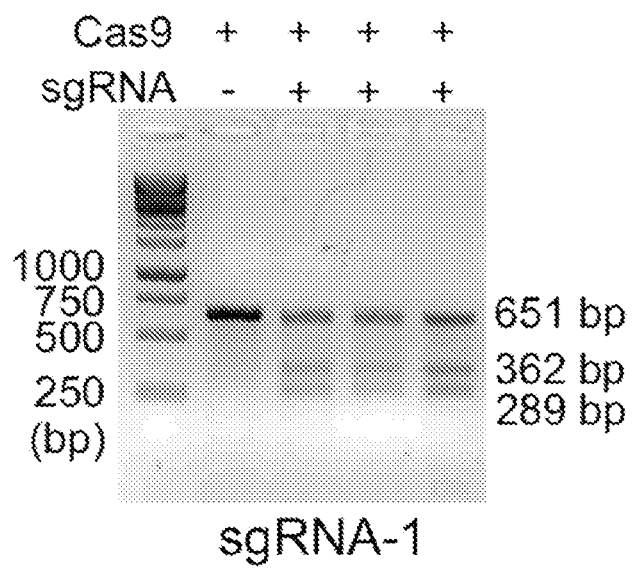
Figure 10C:
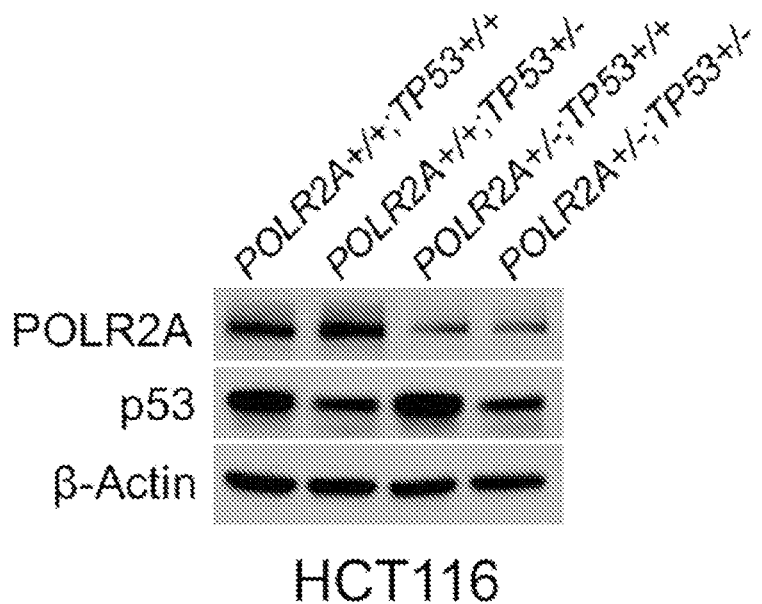
Figure 10D:
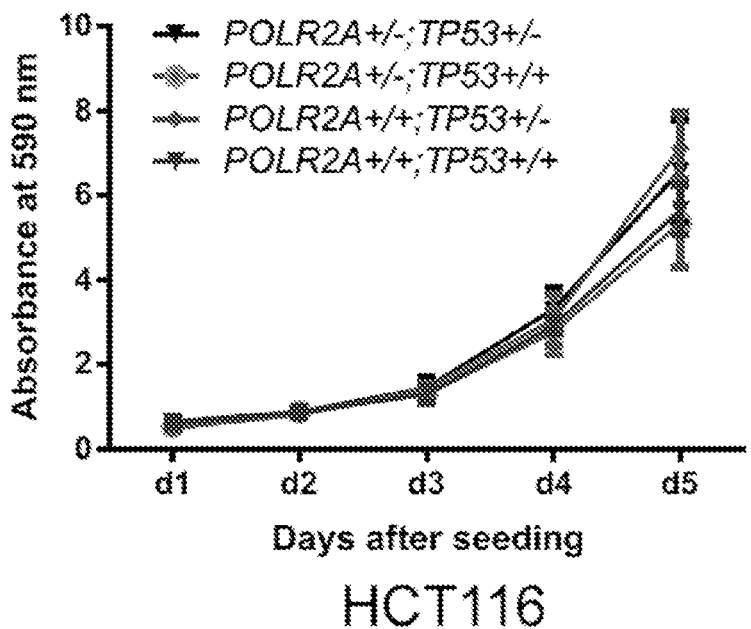
Figure 10E:
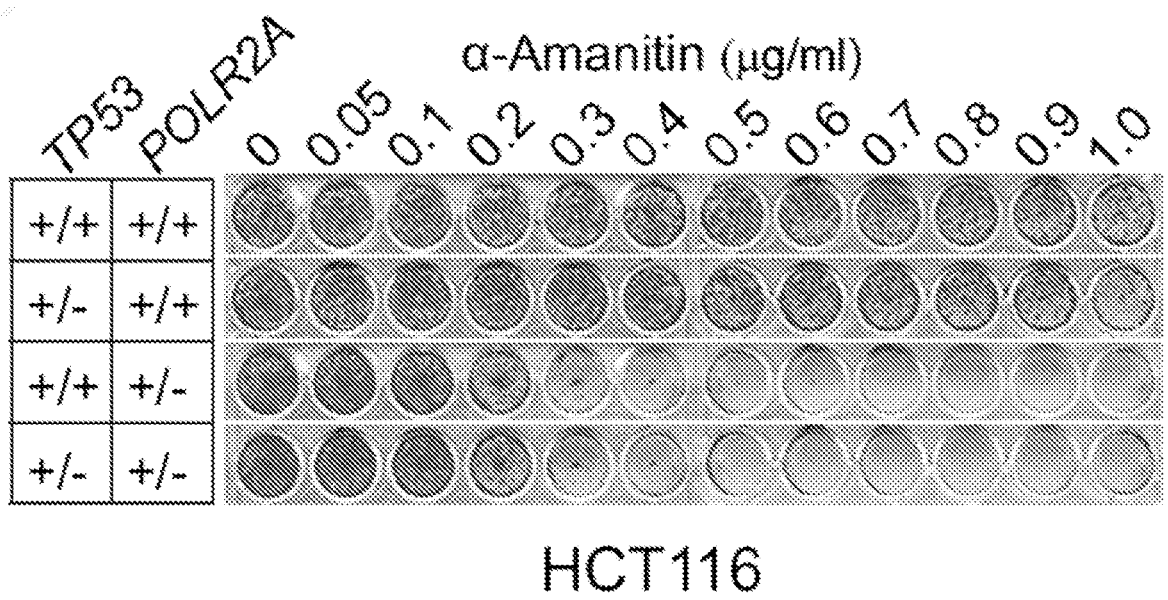
Figure 10F:
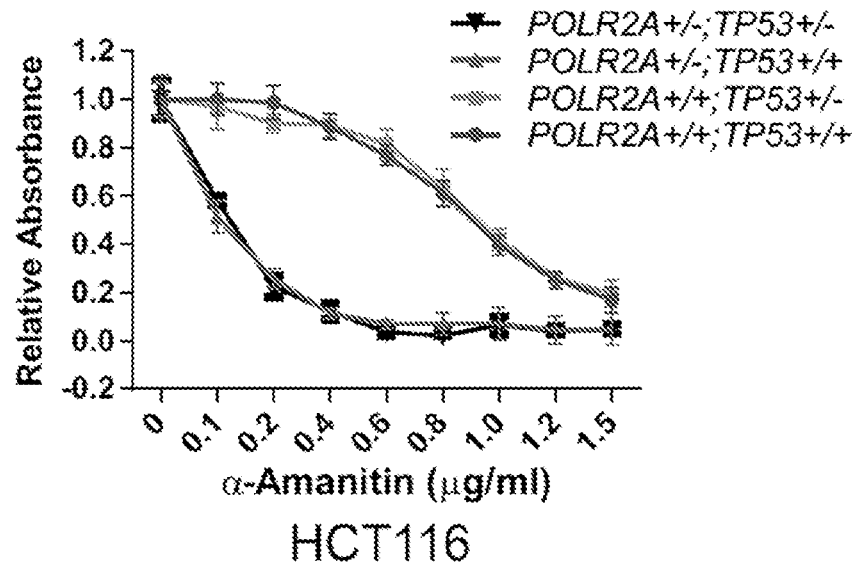
Figure 10G:
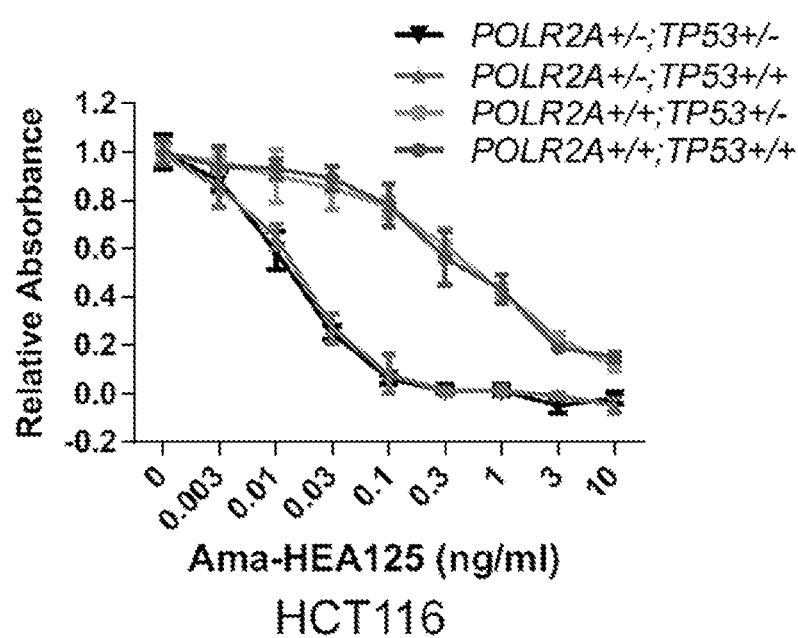
Figure 13A:
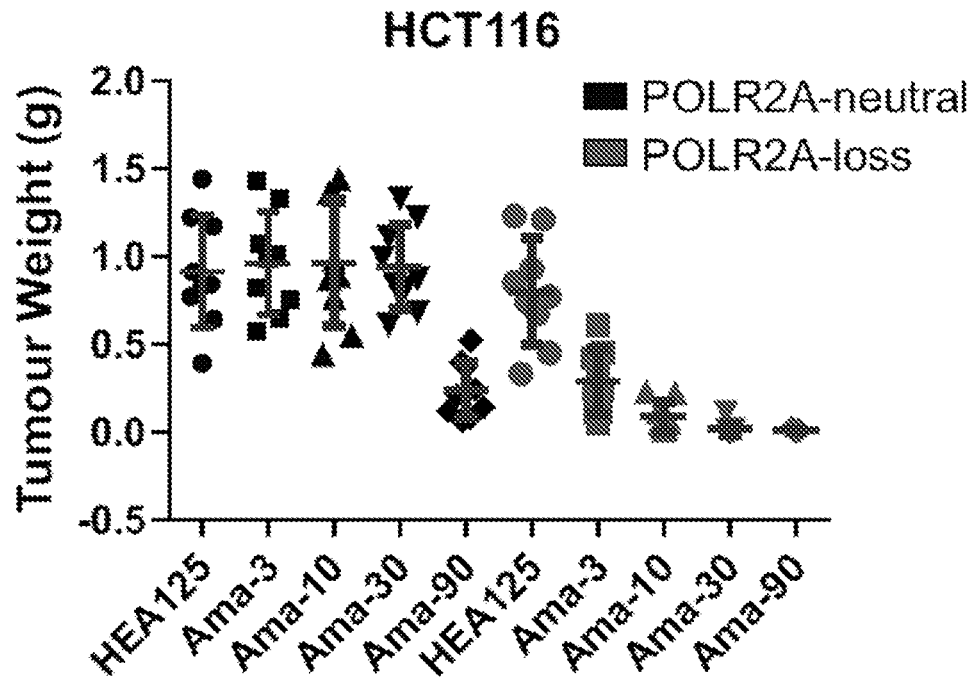
FIGS. 13A-D Suppression of POLR2A selectively inhibits the POLR2A$^{loss}$ tumor growth (FIGS. 13A AND 13B) Tumor weights of orthotopically implanted HCT116 (FIG. 13A) and xhCRC (FIG. 13B) tumors were measured (n=10 mice per group).
Figure 13B:
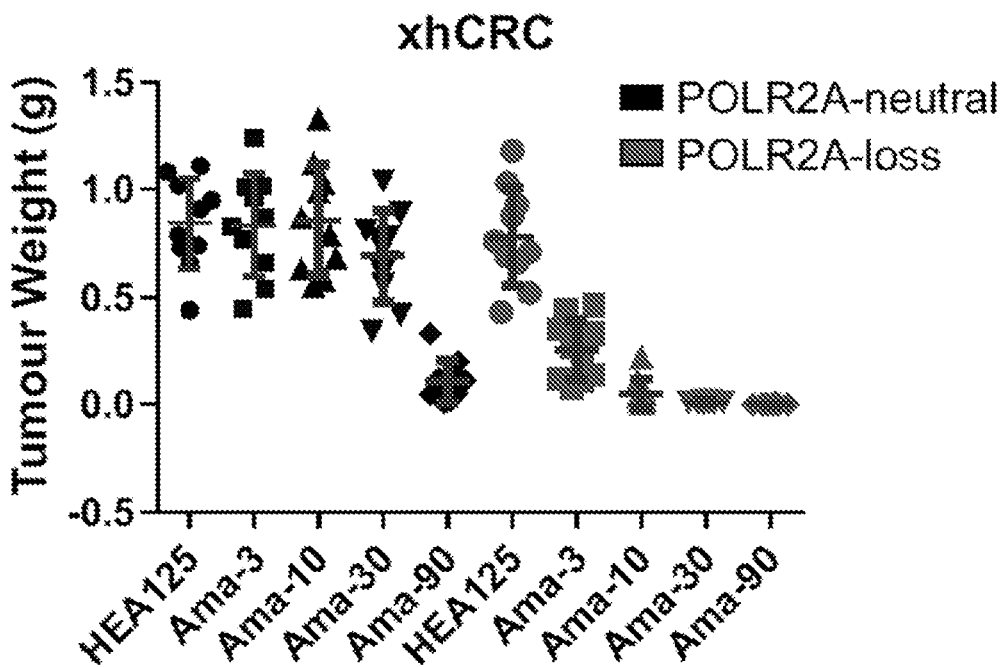
Figure 13C:
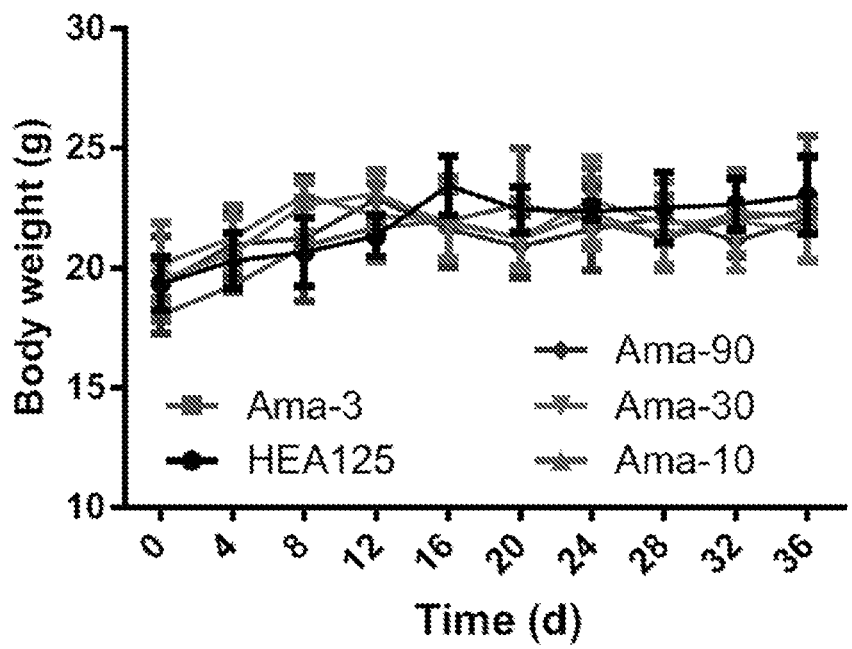
Figure 13D:
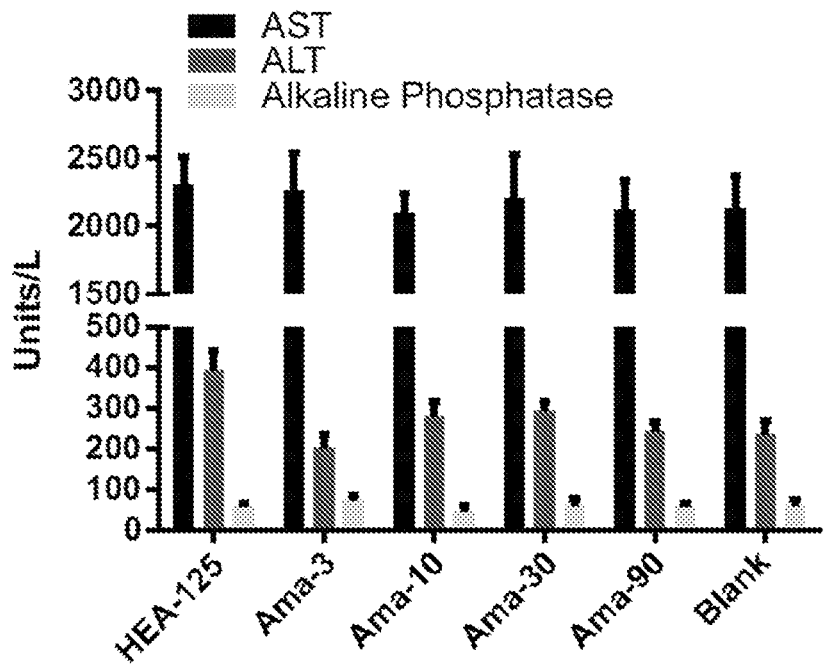
Figure 14A:
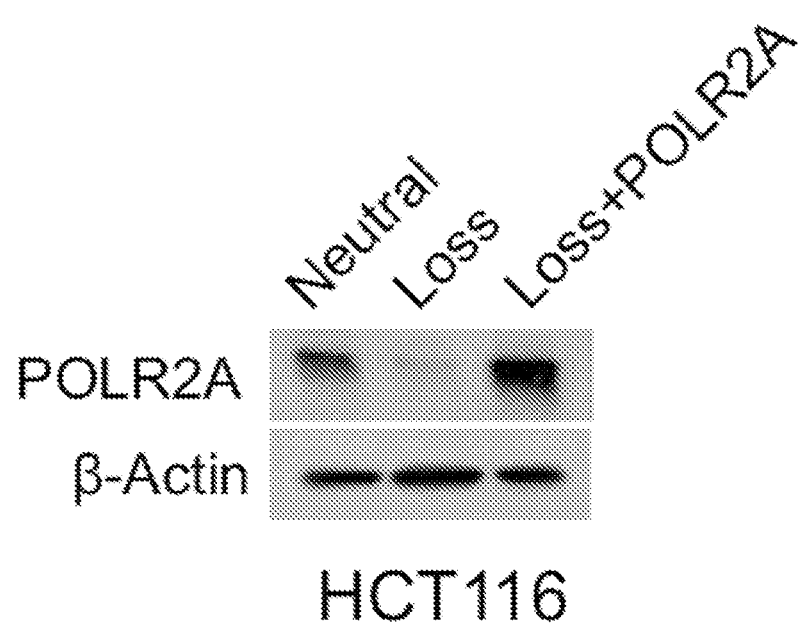
FIGS. 14A-F. Suppression of POLR2A by ama-HEA125 inhibits the growth of POLR2A$^{loss}$ tumors.
Figure 14B:
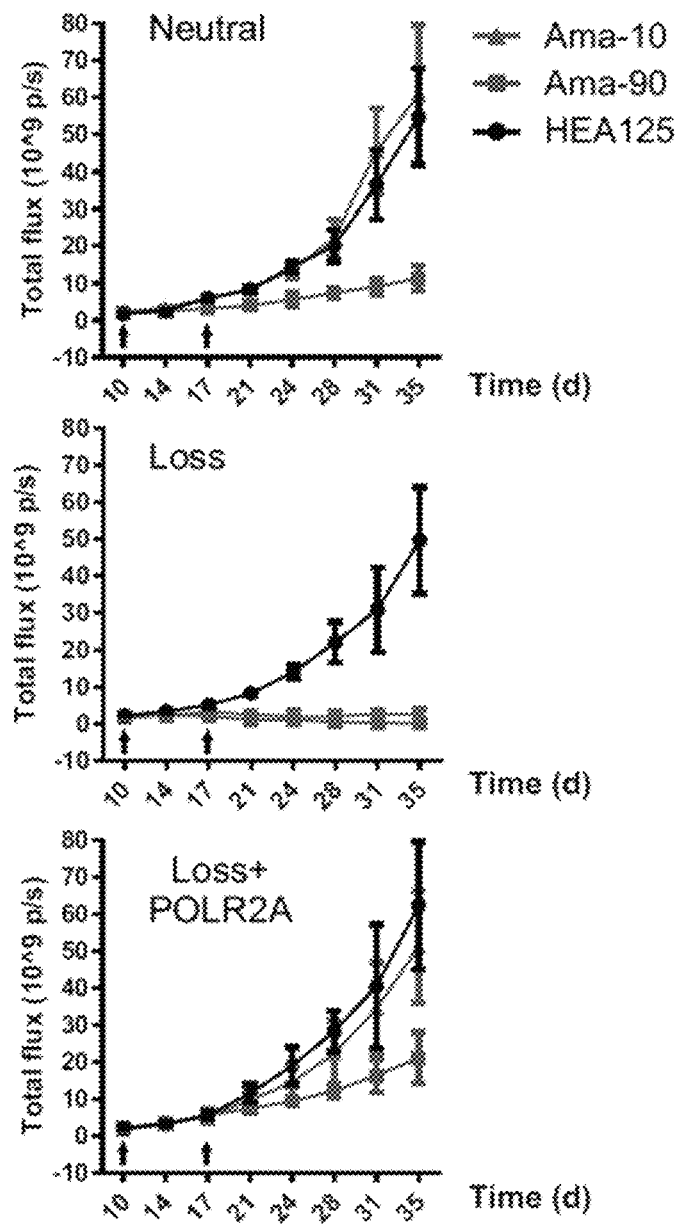
Figure 14C:
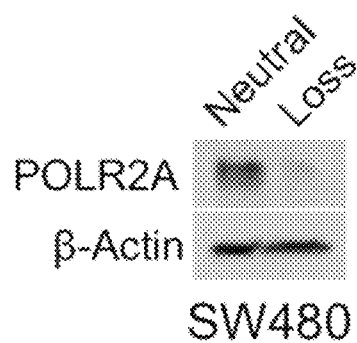
Figure 14D:
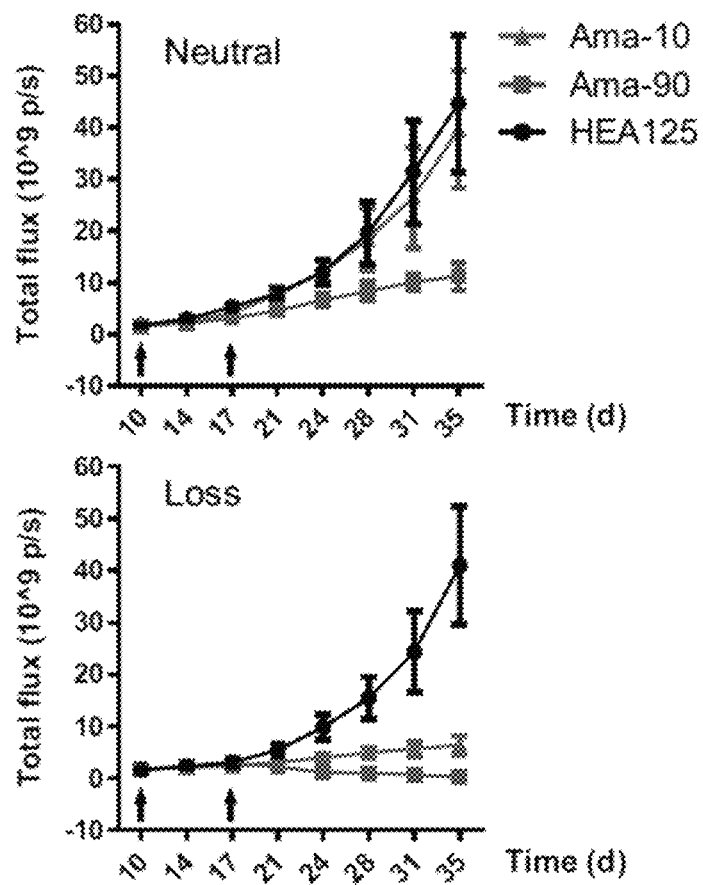
Figure 14E:
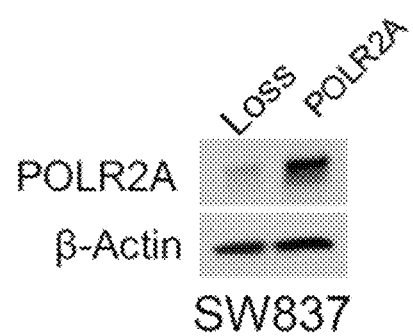
Figure 14F:
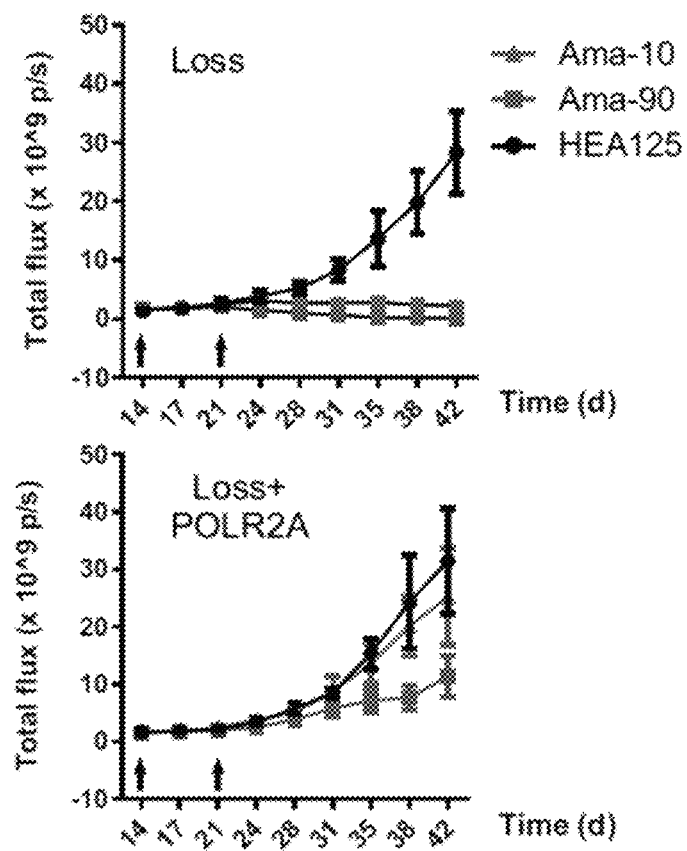

The ama-HEA125 conjugate exhibited a high level of selectivity on the POLR2A$^{loss}$ cancer cells in vitro (FIGS. 3E and 10G). Next, the anti-tumor activity of ama-HEA125 in orthotopic tumor models established by isogenic pairs of TP53/POLR2A$^{neutral}$ and TP53/POLR2A$^{loss}$ xhCRC and HCT116 cells was investigated (FIGS. 4D-4E and 13A-13B). In a dose escalation experiment, ama-HEA125 was administered to the tumor-bearing mice as dual intraperitoneal injections at the dose of 3, 10, 30, or 90 μg with respect to α-Amanitin per kg of mouse body weight (n=10 mice per group). Control mice received unconjugated HEA125 mAb (n=10 mice). In the mice bearing POLR2A$^{loss}$ tumors, control HEA125-treated mice showed continuous tumor growth within 25 days after antibody injection. The treatment of ama-HEA125 showed strong inhibition on tumor growth even at the lowest dose of 3 μg kg$^{-1}$. All the POLR2A$^{loss}$ tumors responded to the ama-HEA125 treatment, and tumor volume regressed dramatically (FIGS. 4D-4E). Complete tumor regression was observed in 10 of 10 (90 μg kg$^{-1}$), 8 of 10 (30 μg kg$^{-1}$), and 6 of 10 (10 μg kg$^{-1}$) mice bearing POLR2A$^{loss}$ HCT116 tumors 25 days after the first administration of ama-HEA125 (FIG. 4D). By contrast, significant tumor inhibition was observed in the mice bearing POLR2A$^{neutral}$ tumors only at the highest dose of 90 μg kg$^{-1}$, but not at the doses of 3-30 μg kg$^{-1}$. Similar results were observed in the mice bearing xhCRC-derived tumors (FIG. 4E). Consistent with previous studies (Moldenhauer et al., 2012), treatment of ama-HEA125 at the tested doses had no notable toxicity in vivo. Analysis of body weights and blood liver enzymes did not reveal any substantial differences between the ama-HEA125-treated group and the control HEA125-treated group (FIGS. 13C and 13D), suggesting negligible systemic toxicity of the ama-HEA125 conjugate. In addition, the anti-tumor activity of ama-HEA125 was further tested in orthotopic tumors derived from the POLR2A$^{neutral}$ SW480 cells and the POLR2A$^{loss}$ SW837 cells (FIGS. 14A-14F). Treatment of ama-HEA125 at a dose of 10 µg kg$^{-1}$ was sufficient to inhibit tumor growth in all the POLR2A$^{loss}$ tumors, while POLR2A$^{neutral}$ (SW480) or POLR2A-reintroduced (SW837 expressing exogenous POLR2A) POLR2A$^{loss}$ tumors were only significantly inhibited by ama-HEA125 at the dose of 90 µg kg$^{-1}$.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,870,287
U.S. Pat. No. 5,091,513
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,846,945
U.S. Patent Publn. No. 2005/0214860
U.S. Patent Publn. No. 2009/0304666
PCT Publn. No. WO2012/119787
Austin-Ward and Villaseca, *Revista Medica de Chile*, 126(7):838-845, 1998.
Bensaude, "Inhibiting eukaryotic transcription: Which compound to choose? How to evaluate its activity?" *Transcription*, 2(3):103, 2011.
Bukowski et al., *Clinical Cancer Res.*, 4(10):2337-2347, 1998.
Chene, "Inhibiting the p53-MDM2 interaction: an important target for cancer therapy," *Nat. Rev. Cancer*, 3(2): 102, 2003.
Cheok et al., "Translating p53 into the clinic," *Nat. Rev. Clin. Oncol.*, 8(1):25, 2011.
Christodoulides et al., *Microbiology*, 144(Pt 11):3027-3037, 1998.
Cong et al., "Multiplex genome engineering using CRISPR/Cas systems," *Science*, 339:819-823, 2013.
Davidson et al., *J. Immunother.*, 21(5):389-398, 1998.
Derheimer et al., "RPA and ATR link transcriptional stress to p53," *Proc. Natl. Acad. Sci. USA*, 104(31):12778, 2007.
Faulstich and Fiume, "Protein conjugates of fungal toxins," *Methods Enzymol.*, 112:225, 1985.
Goldstein et al., "Understanding wild-type and mutant p53 activities in human cancer: new landmarks on the way to targeted therapies," *Cancer Gene Ther.*, 18(1):2, 2011.
Guschin et al., "A rapid and general assay for monitoring endogenous gene modification," *Methods Mol. Biol.*, 649: 247-256, 2010.
Hanibuchi et al., *Int. J. Cancer*, 78(4):480-485, 1998.
Haupt and Haupt, "Manipulation of the tumor suppressor p53 for potentiating cancer therapy," *Semin. Cancer Biol.*, 14(4):244, 2004.
Hellstrand et al., *Acta Oncologica*, 37(4):347-353, 1998.
Hui and Hashimoto, *Infection Immun.*, 66(11):5329-5336, 1998.
Lane et al., "p53-based cancer therapy," *Cold Spring Harb. Perspect. Biol.*, 2(9):a001222, 2010.
Letschert et al., "Molecular characterization and inhibition of amanitin uptake into human hepatocytes," *Toxicol. Sci.*, 91(1):140, 2006.
Lindell et al., "Specific inhibition of nuclear RNA polymerase II by alpha-amanitin," *Science*, 170(3956):447, 1970.
Liu et al., "Kaposi's sarcoma-associated herpesvirus-encoded microRNA miR-K12-11 attenuates transforming growth factor beta signaling through suppression of SMAD5," *Journal of Virology*, 86:1372-1381, 2012.
Lu et al., "Endothelial cells promote the colorectal cancer stem cell phenotype through a soluble form of Jagged-1," *Cancer Cell*, 23(2):171, 2013.
Moldenhauer et al., "Therapeutic potential of amanitin-conjugated anti-epithelial cell adhesion molecule monoclonal antibody against pancreatic carcinoma," *J. Natl. Cancer Inst.*, 104(8):622, 2012.
Negrini et al., "Genomic instability—an evolving hallmark of cancer," *Nat. Rev. Mol. Cell Biol.*, 11(3):220, 2010.
Nijhawan et al., "Cancer vulnerabilities unveiled by genomic loss," *Cell*, 150(4):842-854, 2012.
Pecot et al., "Therapeutic Silencing of KRAS Using Systemically Delivered siRNAs," *Mol. Cancer Ther.*, 13(12): 2876-2885, 2014.
Petitjean et al., "Impact of mutant p53 functional properties on TP53 mutation patterns and tumor phenotype: lessons from recent developments in the IARC TP53 database," *Hum. Mutat.*, 28(6):622, 2007.
Qin et al., *Proc. Natl. Acad. Sci. USA*, 95(24):14411-14416, 1998.
Ran et al., "Genome engineering using the CRISPR-Cas9 system," *Nature Protocols*, 8:2281-2308, 2013.
Shalem et al., "Genome-scale CRISPR-Cas9 knockout screening in human cells," *Science*, 343(6166):84, 2014.
Toledo and Wahl, "Regulating the p53 pathway: in vitro hypotheses, in vivo veritas," *Nat. Rev. Cancer*, 6(12):909, 2006.
Vazquez et al., "The genetics of the p53 pathway, apoptosis and cancer therapy," *Nat. Rev. Drug Discov.*, 7(12):979, 2008.
Wade et al., "MDM2, MDMX and p53 in oncogenesis and cancer therapy," *Nat. Rev. Cancer*, 13(2):83, 2013.
Wang et al., "Genetic screens in human cells using the CRISPR-Cas9 system," *Science*, 343(6166):80, 2014.
Wang et al., "One-step generation of mice carrying mutations in multiple genes by CRISPR/Cas-mediated genome engineering," *Cell*, 153(4):910, 2013.
Went et al., "Frequent EpCam protein expression in human carcinomas," *Hum. Pathol.*, 35(1):122, 2004.

What is claimed is:

1. A method of treating a patient having cancer comprising:
   (a) selecting a patient determined to have cancer cells comprising (i) a hemizygous loss of the TP53 gene; (ii) a hemizygous loss of the POLR2A gene; or (iii) a decreased level of expression of a POLR2A gene product relative to a reference level; and
   (b) administering a therapeutically effective amount of POLR2A inhibitor to the patient, wherein the POLR2A inhibitor comprises an amatoxin, and wherein the amatoxin is conjugated to an antibody that specifically binds to a tumor-associated antigen.

2. The method of claim 1, wherein the amatoxin is alpha-amanitin.

3. The method of claim 1, wherein the POLR2A gene product is an mRNA.

4. The method of claim 1, wherein the POLR2A gene product is a protein.

5. The method of claim 1, wherein the reference expression level is an expression level in non-cancerous cells.

6. The method of claim 1, wherein the cancer cells have been determined to exhibit a hemizygous loss of the TP53 gene.

7. The method of claim 1, wherein the cancer cells have been determine to exhibit a hemizygous loss of the POLR2A gene.

8. The method of claim 1, wherein the patient has cancer cells that exhibit a decreased level of expression of a POLR2A gene product relative to a reference expression level.

9. The method of claim 1, wherein the cancer cells are lung cancer, brain cancer, breast cancer, liver cancer, ovarian cancer, colorectal cancer, prostate cancer, or pancreatic cancer cells.

10. The method of claim 1, wherein the cancer cells are metastatic, recurrent, or multi-drug resistant.

11. The method of claim 1, further comprising administering at least a second anticancer therapeutic.

12. The method of claim 11, wherein the second anticancer therapeutic is a chemotherapeutic agent.

13. The method of claim 12, wherein the chemotherapeutic agent is 5-fluorouracil, oxaliplatin, or SN-38.

14. The method of claim 1, wherein the patient is a human.

15. The method of claim 1, wherein the patient is a non-human mammal.

16. The method of claim 1, wherein the patient has previously undergone at least one round of anti-cancer therapy.

* * * * *

SEQUENCE LISTING

<160> NUMBER OF SEQ ID NOS: 32

<210> SEQ ID NO 1
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 1
gaggttggct ctgactgtac c                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 2
tccgtcccag tagattacca c                                              21

<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3
ttgtatccgt acccacagca                                                20

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4
catgatcagc tccccattct                                                20

<210> SEQ ID NO 5
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 5
ttagctttgt tcttcccga                                                 19

<210> SEQ ID NO 6
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 6
tgttgtccat ctcctcccc                                                 19

<210> SEQ ID NO 7
<211> LENGTH: 25
<212> TYPE: DNA
<213> ORGANISM: Artificial Sequence

```
<220> FEATURE:
<223> OTHER INFORMATION: Synthetic polynucleotide

<400> SEQUENCE: 7
caccgcggcc tccctcagtc gtctc                                               25

<210> SEQ ID NO 8
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 8
aaacgagacg actgagggag gccgc                                               25

<210> SEQ ID NO 9
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 9
caccggccgc tgccaaacat gtgc                                                24

<210> SEQ ID NO 10
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 10
aaacgcacat gtttggcagc ggcc                                                24

<210> SEQ ID NO 11
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 11
aaaatctcca tctggacacg aaagg                                               25

<210> SEQ ID NO 12
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 12
agcgcaaaac tttcattgtc ttcac                                               25

<210> SEQ ID NO 13
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 13
caccgccatt gttcaatatc gtccg                                               25
```

<210> SEQ ID NO 14
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 14
aaaccggacg atattgaaca atggc                                  25

<210> SEQ ID NO 15
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 15
caccgggcag ctacggtttc cgtc                                   24

<210> SEQ ID NO 16
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 16
aaacgacgga aaccgtagct gccc                                   24

<210> SEQ ID NO 17
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 17
gaggagccgc agtcagatcc ta                                     22

<210> SEQ ID NO 18
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 18
gatacggcca ggcattgaag tc                                     22

<210> SEQ ID NO 19
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 19
uucuccgaac gugucacgu                                         19

<210> SEQ ID NO 20
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 20
acgugacacg uucggagaa                                          19

<210> SEQ ID NO 21
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 21
ccaacaugcu gacagauau                                          19

<210> SEQ ID NO 22
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 22
auaucuguca gcauguugg                                          19

<210> SEQ ID NO 23
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 23
ccaagaagcg gcucacaca                                          19

<210> SEQ ID NO 24
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 24
ugugugagcc gcuucuugg                                          19

<210> SEQ ID NO 25
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 25
ctggccgctg ccaaacatgt gcagg                                   25

<210> SEQ ID NO 26
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 26
gcggcctccc tcagtcgtct ctgg                                    24

<210> SEQ ID NO 27

```
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 27
ggggcggcct ccctcagtcg tctctgggta tttgatgcc                              39

<210> SEQ ID NO 28
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 28
ggggcggcct ccctcagtcc tctgggtatt tgatgcc                                37

<210> SEQ ID NO 29
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 29
ggactggccg ctgccaaaca tgtgcaggta agtgctgg                               38

<210> SEQ ID NO 30
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 30
ggactggccg ctgccaaaact gctgg                                            25

<210> SEQ ID NO 31
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 31
gggcagctac ggtttccgtc tgg                                               23

<210> SEQ ID NO 32
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 32
ccattgttca atatcgtccg ggg                                               23
```